US010184113B2

(12) United States Patent
Lee et al.

(10) Patent No.: US 10,184,113 B2
(45) Date of Patent: Jan. 22, 2019

(54) EX VIVO HUMAN MULTIPLE MYELOMA CANCER NICHE AND ITS USE AS A MODEL FOR PERSONALIZED TREATMENT OF MULTIPLE MYELOMA

(71) Applicants: Hackensack University Medical Center, Hackensack, NJ (US); The Trustees of The Stevens Institute of Technology, Hoboken, NJ (US)

(72) Inventors: Woo Lee, Ridgewood, NJ (US); Jenny Zilberberg, Yardley, PA (US); David Samuel Siegel, West Orange, NJ (US); Peter Tolias, Westfield, NJ (US); Hongjun Wang, Milburn, NJ (US); Wenting Zhang, Jersey City, NJ (US)

(73) Assignees: Hackensack University Medical Center, Hackensack, NJ (US); The Trustees of The Stevens Institute of Technology, Hoboken, NJ (US)

( * ) Notice: Subject to any disclaimer, the term of this patent is extended or adjusted under 35 U.S.C. 154(b) by 0 days.

(21) Appl. No.: 14/973,329

(22) Filed: Dec. 17, 2015

(65) Prior Publication Data
US 2016/0137986 A1 May 19, 2016

Related U.S. Application Data

(62) Division of application No. 13/827,170, filed on Mar. 14, 2013, now Pat. No. 9,267,938.

(51) Int. Cl.
*C12M 3/06* (2006.01)
*C12N 5/09* (2010.01)
(Continued)

(52) U.S. Cl.
CPC ........... *C12N 5/0694* (2013.01); *C12M 23/16* (2013.01); *G01N 33/5091* (2013.01);
(Continued)

(58) Field of Classification Search
CPC ... C12N 5/0694; C12M 23/16; G01N 33/574; G01N 33/5091; G01N 2800/7028; G01N 2510/00; G01N 2800/52; G01N 2500/10
See application file for complete search history.

(56) References Cited

U.S. PATENT DOCUMENTS 6,048,498 A 4/2000 Kennedy
6,090,251 A 7/2000 Sundberg et al.
(Continued)

OTHER PUBLICATIONS

Kirshner et al. A unique three-dimensional model for evaluating the impact of therapy on multiple myeloma. Blood (2008), v1127(7), p. 2935-2945.*
(Continued)

*Primary Examiner* — Sean C. Barron
(74) *Attorney, Agent, or Firm* — McCarter & English, LLP; Beverly W. Lubit

(57) ABSTRACT

The described invention provides an ex vivo dynamic multiple myeloma (MM) cancer niche contained in a microfluidic device. The dynamic MM cancer niche includes (a) a three-dimensional tissue construct containing a dynamic ex vivo bone marrow (BM) niche, which contains a mineralized bone-like tissue containing viable osteoblasts self-organized into cohesive multiple cell layers and an extracellular matrix secreted by the viable adherent osteoblasts; and a microenvironment dynamically perfused by nutrients and dissolved gas molecules; and (b) human myeloma cells seeded from a biospecimen composition comprising mononuclear cells and the multiple myeloma cells. The human myeloma cells are in contact with osteoblasts of the BM niche, and the viability of the human myeloma cells is maintained by the MM cancer niche.

22 Claims, 10 Drawing Sheets

(51) Int. Cl.
*G01N 33/50* (2006.01)
*G01N 33/574* (2006.01)
(52) U.S. Cl.
CPC ....... *G01N 33/574* (2013.01); *G01N 2500/10* (2013.01); *G01N 2510/00* (2013.01); *G01N 2800/52* (2013.01); *G01N 2800/7028* (2013.01)

(56) References Cited

U.S. PATENT DOCUMENTS

| | | | |
|---|---|---|---|
| 7,374,906 B2 | 5/2008 | Kirk et al. | |
| 7,858,044 B2* | 12/2010 | Coassin | B01L 3/50851 422/553 |
| 8,389,294 B2 | 3/2013 | Beebe et al. | |
| 9,267,938 B2 | 2/2016 | Lee et al. | |
| 2007/0166816 A1 | 7/2007 | Campbell et al. | |
| 2009/0117653 A1* | 5/2009 | Kirshner | C12N 5/0693 435/378 |
| 2011/0086382 A1 | 4/2011 | Marx et al. | |
| 2013/0143230 A1 | 6/2013 | Tolias et al. | |

OTHER PUBLICATIONS

Munaka et al. A Microfluidic Device to Mimic the Bone Marrow Microenvironment: Real-Time Observation of the Leukemic Cell Behavior. 15th International Conference on Minaturized Systems for Chemistry and Life Sciences (2011), p. 1475-1477.*
"Basic Microfluidic Concepts" (2011). Internet Article, 6 pages.*
Barille et al. Myeloma Cells Upregulate Interleukin-6 Secretion in Osteoblastic Cells Through Cell-to-Cell Contact But Downregulate Osteocalcin. Blood (2004), v86(8), p. 3151-3159.*
Matsumoto et al. TGF-β-related mechanisms of bone destruction in multiple myeloma. Bone (2011), v48, p. 129-134.*
Jiang, W.G., et al. "Hepatocyte growth factor/scatter factor, a cytokine playing multiple and converse roles." Histol Histopathol. Apr. 1997; 12(2): 537-55.
Karadag, A., et al. "Human myeloma cells promote the production of interleukin 6 by primary human osteoblasts." Br J Haematol. Feb. 2000; 108(2): 383-90.
Kelsoe, G. "Life and death in germinal centers (redux)." Immunity. Feb. 1996; 4(2): 107-11.
Kerkela, R., et al. "Cardiotoxicity of the cancer therapeutic agent imatinib mesylate." Nat Med. Aug. 2006; 12(8): 908-16.
Kirshner et al. (2008). Aunique three-dimensional model for evaluating the impact of therapy on multiple myeloma. Blood, v1127(7), p. 2935-2945.
Kirshner, J., et al. "A unique three-dimensional model for evaluating the impact of therapy on multiple myeloma." Blood. Oct. 1, 2008; 112(7): 2935-45.
Kirshner, J., et al. "In a patient with biclonal Waldenstrom macroglobulinemia only one clone expands in three-dimensional includes culture and includes putative cancer stem cells." Leuk Lymphoma. Feb. 2011; 52(2): 285-9.
Kolf, C.M., et al. "Mesenchymal stromal cells. Biology of adult mesenchymal stem cells: regulation of niche, self-renewal and differentiation." Arthritis Res Ther. 2007; 9(1): 204.
Komine, A., et al. "Establishment of adipose-derived mesenchymal stem cell lines from a p53-knockout mouse." Biochem Biophys Res Commun. Oct. 5, 2012; 426(4): 468-74.
Korsmeyer, S.J., et al. "Immunoglobulin gene rearrangement and cell surface antigen expression in acute lymphocytic leukemias of T cell and B cell precursor origins." J Clin Invest. Feb. 1983; 71(2): 301-13.
Krishnan, V., et al. "Regulation of bone mass by Wnt signaling." J Clin Invest. May 2006; 116(5): 1202-9.
Kuehl, W.M., et al. "Molecular pathogenesis of multiple myeloma and its premalignant precursor." J Clin Invest. Oct. 2012; 122(10): 3456-63.

Kumar, S., et al. "Expression of VEGF and its receptors by myeloma cells." Leukemia. Oct. 2003; 17(10): 2025-31.
Kumar, S., et al. "Prognostic value of bone marrow angiogenesis in patients with multiple myeloma undergoing high-dose therapy." Bone Marrow Transplant. Aug. 2004; 34(3): 235-9.
Kuppers, R., et al. "Hodgkin disease: Hodgkin and Reed-Sternberg cells picked from histological sections show clonal immunoglobulin gene rearrangements and appear to be derived from B cells at various stages of development." Proc Natl Acad Sci USA.Nov. 8, 1994; 91(23): 10962-6.
Kyle, R.A. "The American Society of Hematology: a success at age 50; blood banking and sodium citrate." Blood. Apr. 15, 2008; 111(8): 4417-8.
Kyle, R.A., et al. "Multiple myeloma." Blood. Mar. 15, 2008; 111(6): 2962.72.
Lanzavecchia, A. "Antigen-specific interaction between T and B cells." Nature. Apr. 11-17, 1985; 314(6011): 537-9.
Lebien, T.W., et al. "B lymphocytes: how they develop and function." Blood. Sep. 1, 2008; 112(5): 1570-80.
Lee et al. (epub 2011). Microfluidic 3D bone tissue model for high-throughput evaluation of wound-healing and infection-preventing biomaterials. Biomaterials, v33, p. 999-1006.
Lee, H.J., et al."Changes in surface markers of human mesenchymal stem cells during the chondrogenic diffferentiation and dedifferentiation processes in vitro." Arthritis Rheum. Aug. 2009; 60(8): 2325-32.
Lee, J.H., et al. "Microfluidic 3D bone tissue model for high-throughput evaluation of wound-healing and infection-preventing biomaterials." Biomaterials. Feb. 2012; 33(4): 999-1006.
Lentzsch, S., et al. "Pathophysiology of multiple myeloma bone disease." Hematol Oncol Clin North Am. Dec. 2007; 21 (6): 1035-49.
Liu, G., et al. "Canonical Wnts function as potent regulators of osteogenesis by human mesenchymal stem cells." J Cell Biol. Apr. 6, 2009; 185(1): 67-75.
Love, J.C., et al. "Fabrication of three-dimensional microfluidic systems by soft lithography." MRS Bulletin. 2991 Jul; 523-527.
Majumdar, M.K., et al. "Human marrow-derived mesenchymal stem cells (MSCs) express hematopoietic cytokines and support long-term hematopoiesis when differentiated toward stromal and osteogenic lineages." J Hematother Stem Cell Res. Dec. 2000; 9(6):841-8.
Manochakian et al (2007). Clinical Impact of Bortezomib in Front-line Regimens for Patients with Multiple Myeloma. The Oncologist, v12, p. 978-990.
Marom, R., et al. "Characterization of adhesion and differentiation markers of osteogenic marrow stromal cells." J Cell Physiol. Jan. 2005; 202(1): 41-8.
Massignani, M., et al. "Enhanced fluorescence imaging of live cells by effective cytosolic delivery of probes." PLoS One. May 3, 2010; 5(5): e10459.
McHeyzer-Williams, L.J., et al. "Antigen-specific memory B cell development." Annu Rev Immunol. 2005; 23: 487-513.
Menu, E. et al. "Myeloma cells (5TMM) and their interactions with the marrow microenvironment." Blood Cells Mol Dis. Sep.-Oct. 2004; 33(2): 111-9.
Merchionne, F., et al. "New therapies in multiple myeloma." Clin Exp Med. Sep. 2007; 7(3): 83-97.
Minguell, J.J., et al. "Mesenchymal stem cells." Exp Biol Med (Maywood). Jun. 2011; 226(6): 507-20.
Mohty, B., et al. "Treatment strategies in relapsed and refractory multiple myeloma: a focus on drug sequencing and 'retreatment' approaches in the era of novel agents." Leukemia. Jan. 2012; 26(1): 73-85.
Montecino-Rodriguez, E., et al. "Identification of a B-1 B cell-specified progenitor." Nat Immunol. Mar. 2006; 7(3): 293-301.
Nefedova, Y., et al. "Involvement of Notch-1 signaling in bone marrow stroma-mediated de novo drug resistance of myeloma and other malignant lymphoid cell lines." Blood. May 1, 2004; 103(9): 3503-10.
Niziolek, P.J., et al. "High-bone-mass-producing mutations in the Wnt signaling pathway result in distinct skeletal phenotypes." Bone. Nov. 2011; 49(5): 1010-9.

(56) References Cited

OTHER PUBLICATIONS

Novak, A., et al. "Signaling through beta-catenin and Lef/Tcf." Cell Mol Life Sci. Oct. 30, 1999; 56(5-6): 523-37.
Nutt, S.L., et al. "Commitment to the B-lymphoid lineage depends on the transcription factor Pax5." Nature. Oct. 7, 1999; 401(6753): 556-62.
Otjacques, E., et al. "Biological aspects of angiogenesis in multiple myeloma." Int J Hematol. Dec. 2011; 94(6): 505-18.
Ozols et al. (1987). Enhanced melphalan cytotoxicity in human ovarian cancer in vitro and in tumor-bearing nude mice by buthionine sulfoximine depletion of glutathione. Biochemical Pharmacology, v36(1), p. 147-153.
Pillai, S., et al. "Marginal zone B cells." Annu Rev Immunol. 2005; 23: 161-96.
Podar, K., et al. "The pathophysiologic role of VEGF in hematologic malignancies: therapeutic implications." B;ppd/Feb. 15, 2005; 105(4): 1383-95.
Pratt, G. "Molecular aspects of multiple myeloma." Mol Pathol. Oct. 2002; 55(5): 273-83.
Quake, S.R., et al. "From micro- to nanofabrication with soft materials." Science. Nov. 24, 2000; 290(5496): 1536-40.
Quarto, N., et al. "Opposite spectrum of activity of canonical Wnt signaling in the osteogenic context of undifferentiated and differentiated mesenchymal cells: implications for tissue engineering." Tissue Eng Part A. Oct. 2010; 16(10): 3185-97.
Raab, M.S., et al. "Multiple myeloma." Lancet. Jul. 25, 2009; 374(9686): 324-39.
Radbruch, A., et al. "Competence and competition: the challenge of becoming a long-lived plasma cell." Nat Rev Immunol. Oct. 2006; 6(10): 741-50.
Radtke, F., et al. "The role of Notch in tumorigenesis: oncogene or tumour suppressor?" Nat Rev Cancer. Oct. 2003; 3(10): 756-67.
Raje, N., et al. "Advances in the biology and treatment of bone disease in multiple myeloma." Clin Cancer Res. Mar. 15, 2011; 17(6): 1278-86.
Alici, E., et al. "Visualization of 5T33 myeloma cells in the C57/BL/KaLwRij mouse: establishment of a new syngeneic murine model of multiple myeloma." Exp Hematol. Nov. 2004; 32(11): 1064-72.
Almeida, M., et al. "Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT." JBiol Chem. Dec. 16, 2005; 280(5): 41342-51.
Arnsdorf, E.J., et al. "Non-canonical Wnt signaling and N-cadherin related beta-catenin signaling play a role in mechanically induced osteogenic cell fate." PLoS One. 2009; 4(4): e5388.
Baksh, D., et al. "Canonical and non-canonical Wnts differentially affect the development potential of primary isolate of human bone marrow mesenchymal stem cells." J Cell Physiol. Sep. 2007; 212(3): 817-26.
Baksh, D., et al. "Cross-talk between Wnt signaling pathways in human mesenchymal stem cells leads to functional antagonism during osteogenic differentiation." J Cell Biochem. Aug. 1, 2007; 101(5): 1109-24.
Baraniak, P.R., et al. "Stem cell paracrine actions and tissue regeneration." Regen Med. Jan. 2010; 5(1): 121-43.
Barille et al. (2004). Myeloma Cells Upregulate Interleukin-6 Secretion in Osteoblastic Cells Through Cell-to-Cell Contact But Downregulate Osteocalcin. Blood, v86(8), p. 3151-3159.
Bataille, R., et al. "Mechanisms of bone destruction in multiple myeloma: the importance of an unbalanced process in determining the severity of lytic bone disease." J Clin Oncol. Dec. 1989; 7(12): 1909-14.
Bayer-Garner, I.B., et al. "Syndecan-1 (CD138) immunoreactivity in bone marrow biopsies of multiple myeloma: shed syndecan-1 accumulates in fibrotic regions." Mod Pathol. Oct. 2011; 14(10): 1052-8.
Bell, E. "Why 3D is better than 2D." Nat Rev Immunol. Feb. 2006; 6: 87.
Bennet, K.P., et al. "Proteomics reveals multiple routes to the osteogenic phenotype in mesenchymal stem cells." BMC Genomics. Oct. 19, 2007; 8: 380.
Burden, T.J., et al. "Bone marrow stem cell derived paracrine factors for regenerative medicine: current perspectives and therapeutic potential." Bone Marrow Res. 2011: 2011: 207326.
Calimeri, T., et al. "A unique three-dimensional SCID-polymeric scaffold (SCID-synth-hu) model for in vivo expansion of human primary multiple myeloma cells." Leukemia. Apr. 2011; 25(4): 707-11.
Cheng, H., et al. "Osteogenic activity of the fourteen types of human bone morphogenetic proteins (BMPs)." J Bone Joint Surg Am. Aug. 2003; 85-A(8): 1544-52.
Chotinantakul, K., et al. "Hematopoietic stem cell development, niches, and signaling pathways." Bone Marrow Res. 2012: 2012: 270425.
Chung, J.B., et al. "Transitional B cells: step by step towards immune competence." Trends Immunol. Jun. 2003; 24 (6): 343-9.
Cobaleda, C., et al. "Conversion of mature B cells into T cells by dedifferentiation to uncommitted progenitors." Nature. Sep. 27, 2007; 449(7161): 473-7.
Cobaleda, C., et al. "PaxS: the guardian of B cell identity and function." Nat Immunol. May 2007; 8(5): 463-70.
Cook, D.N. "The role of MIP-1 alpha in inflammation and hematopoiesis." J Leukoc Biol. Jan. 1996; 59(1): 61-6.
Coutinho, A., et al. "Thymus-independent B-cell induction and paralysis." Adv Immunol. 1975; 21: 113-236.
D'Souza, S., et al. "Gfi1 expressed in bone marrow stromal cells is a novel osteoblast suppressor in patients with multiple myeloma bone disease." Blood. Dec. 22, 2011; 118(26): 6871-80.
De Raeve, H.R., et al. "The role of the bone marrow microenvironment in multiple myeloma." Histol Histopathol. Oct. 2005; 20(4): 1227-50.
Delamarche, E., et al. "Microfluidic networks for chemical patterning of substrates: design and application to bioassays." J Am Chem Soc. Jan. 9, 1998; 120(3): 500-508.
Delamarche, E., et al. "Patterned delivery of immunoglobulins to surfaces using microfluidic networks." Science. May 2, 1997; 276(5313): 779-81.
Deleu, S., et al. "The effects of JNJ-26481585, a novel hydroxamate-based histone deacetylase inhibitor, on the development of multiple myeloma in the 5T2MM and 5T33MM murine models." Leukemia. Oct. 2009; 23(10): 1894-903.
Dilillo, D.J., et al. "Maintenance of long-lived plasma cells and serological memory despite mature and memory B cell depletion during CD20 immunotherapy in mice." J Immunol. Jan. 1, 2008; 180(1): 361-71.
Dorshkind, K., et al. "Fetal B-cell lymphopoiesis and the emergence of B-1-cell potential." Nat Rev Immunol. Mar. 2007; 7(3): 213-9.
Durie, B.G., et al. "Myeloma management guidelines: a consensus report from the Scientific Advisors of the International Myeloma Foundation." Hematol J. 2003; 4(6): 379-98.
Dvorak, H.F., et al. "Tumor microenvironment and progression." J Surg Oncol. May 1, 2011; 103(6): 468-74.
Edwards, C.M., et al. "Increasing Wnt signaling in the bone marrow microenvironment inhibits the development of myeloma bone disease and reduces tumor burden in bone in vivo." Blood. Mar. 1, 2008; 111(5): 2833-42.
Ehrlich, L.A., et al. "The role of immune cells and inflammatory cytokines in Paget's disease and multiple myeloma." Immunol Rev. Dec. 2005; 208: 252-66.
Engler, A.J., et al. "Matrix elasticity directs stem cell lineage specification." Cell. Aug. 25, 2006; 126(4): 677-89.
Eslaminejad, M.B., et al. "Mesenchymal stem cells: in vitro differentiation among bone and cartilage cell lineages." Yakhteh Medical Journal. 2007; 9(3): 158-169.
Field-Smith, A., et al. "Bortezomib (Velcade Tm) in the Treatment of Multiple Myeloma." Ther Clin Risk Manag. Sep. 2006; 2(3): 271-9.
Fowler, J.A., et al. "Bone marrow stromal cells create a permissive microenvironment for myeloma development: a new stromal role for Wnt inhibitor Dkk1." Cancer Res. May 1, 2012; 72(9): 2183-9.

(56) References Cited

OTHER PUBLICATIONS

Fowler, J.A., et al. "Tumor-host cell interactions in the bone disease of myeloma." Bone. Jan. 2011; 48(1): 121-8.
Fulciniti, M., et al. "Anti-DKK1 mAb (BHQ880) as a potential therapeutic agent for multiple myeloma." Blood. Jul. 9, 2009; 114(2): 371-9.
Galimi, F., et al. "The hepatocyte growth factor and its receptor." Stem Cells. Jul. 1993; 11 Suppl 2: 22-30.
Gimble, J.M., et al. "The function of adipocytes in the bone marrow stroma: an update." Bone. Nov. 1996; 19(5): 421-8.
Giuliani, N., et al. "Angiogenesis and multiple myeloma." Cancer Microenviron. Dec. 2011; 4(3): 325-37.
Giuliani, N., et al. "Multiple myeloma bone disease: Pathophysiology of osteoblast inhibition." Blood. Dec. 15, 2006; 108(13): 3992-6.
Grimaud, E., et al. "Receptor activator of nuclear factor kappaB ligand (RANKL)/osteoprotegerin (OPG) ratio is increased in severe osteolysis." Am J Pathol. Nov. 2003; 163(5): 2021-31.
Grove, E.A. "Wnt signaling meets internal dissent" Genes Dev. Sep. 1, 2011; 25(17): 1759-62.
Hardy, R.R., et al. "B cell development pathways." Annu Rev Immunol. 2001; 19: 595-621.
Hayakawa, K., et al. "The 'Ly-1 B' cell subpopulation in normal immunodefective, and autoimmune mice." J Exp Med. Jan. 1, 1983; 157(1):202-18.
Heider et al. (2009). Serum concentrations of DKK-1 decrease in patients with multiple myeloma responding to anti-myeloma treatment. Eur J Haematol, v82(1), p. 31-38.
Hideshima, T., et al. "Advances in biology of multiple myeloma: clinical applications." Blood. Aug. 1, 2004; 104(3): 607-18.
Hou, Z., et al. "Osteoblast-specific gene expression after transplantation of marrow cells: implications for skeletal gene therapy." Proc Natl Acad Sci USA. Jun. 22, 1999; 96(13): 7294-9.
Jacob, J., et al. "Intraclonal generation of antibody mutants in germinal centres." Nature. Dec. 5, 1991; 354(6352): 389-92.
Janeway, C.A, et al. "The B cell is the initiating antigen-presenting cell in peripheral lymph nodes." J Immunol. Feb. 15, 1987; 138(4): 1051-5.
Rajkumar, S.V. "Thalidomide: tragic past and promising future." Mayo Clinic Proc. Jul. 2004; 79(7): 899-903.
Rajkumar, S.V., et al. "A review of angiogenesis and antiangiogenic therapy with thalidomide in multiple myeloma." Cancer Treat Rev. Oct. 2000; 26(5): 351-62.
Reiser, J., et al. "Potential of mesenchymal stem cells in gene therapy approaches for inherited and acquired diseases." Expert Opin Biol Ther. Dec. 2005; 5(12): 1571-84.
Ria, R., et al. "Gene expression profiling of bone marrow endothelial cells in patients with multiple myeloma." Clin Cancer Res. Sep. 1, 2009; 15(17): 5369-78.
Roccaro, A.M., et al. "Stroma-Derived Exosomes Mediate Oncogenesis in Multiple Myeloma" Blood (ASH Annual Meeting Abstracts). 2011; 118: Abstract 625.
Ron, Y., et al. "Defective induction of antigen-reactive proliferating T cells in B cell-deprived mice." Eur J Immunol. Dec. 1981; 11(12): 964-8.
Ron, Y., et al. "T cell priming in vivo: a major role for B cells in presenting antigen to T cells in lymph nodes." J Immunol. May 1, 1987; 138(9): 2848-56.
Roodman, G.D. "Osteoblast function in myeloma." Bone. Jan. 2011; 48(1): 135-40.
Roodman, G.D. "Pathogenesis of myeloma bone disease." Leukemia. Mar. 2009; 23(3): 435-41.
Roodman, G.D. "Rold of the bone marrow microenvironment in multiple myeloma." J Bone Miner Res. Nov. 2002; 17 (11): 1921-5.
Ryoo, H.M., et al. "Stage-specific expression of Dlx-5 during osteoblast differentiation: involvement in regulation of osteocalcin gene expression." Mol Endocrinol. Oct. 1997;11(11): 1681-94.
Schwartz, R.N., et al. "Current and emerging treatments for multiple myeloma." J Manag Care Pharm. Sep. 2008; 14(7 Suppl): 12-18.
Shapiro-Shelef, M., et al. "Blimp-1 is required for the formation of immunoglobulin secreting plasma cells and pre-plasma memory B cells." Immunity. Oct. 2003; 19(4): 607-20.
Shapiro-Shelef, M., et al. "Regulation of plasma-cell development." Nat Rev Immunol. Mar. 2005; 5(3): 230-42.
Shen, J., et al. "Transplantation of mesenchymal stem cells from young donors delays aging in mice." Sci Rep. 2011; 1:67.
Shipman, C.M., et al. "Osteoprotegerin is a soluble decoy receptor for tumor necrosis factor-related apoptosis-inducing ligand/Apo2 ligand and can function as a paracrine survival factor for human myeloma cells." Cancer Res. Mar. 1, 2003; 63(5):912-6.
Stanley, E.R., et al. "Biology and action of colony-stimulating factor-1." Mol Reprod Dev. Jan. 1997; 46(1): 4-10.
Steiniger, B., et al. "The splenic marginal zone in humans and rodents: an enigmatic compartment and its inhabitants." Histochem Cell Biol. Dec. 2006; 126(6): 641-8.
Tanaka, Y., et al. "Myeloma cell-osteoclast interaction enhances angiogenesis together with bone resorption: a role for vascular endothelial cell growth factor and osteopontin." Clin Cancer Res. Feb. 1, 2007; 13(3): 816-23.
The National Institutes of Health, Resource for Stem Cell Research, at http://stemcells.nih.gov/info/scireport/pages/chapter5.aspx.
Tian, E., et al. "The role of the Wnt-signaling antagonist DKK1 in the development of osteolytic lesions in multiple myeloma." N Engl J Med. Dec. 25, 2003; 349(26): 2483-94.
Tsujimoto, Y., et al. "Cloning of the chromosome breakpoint of neoplastic B cells with the t(14;18) chromosome translocation." Science. Nov. 30, 1984; 226(4678): 1097-9.
Tuan, R.S., et al. "Adult mesenchymal stem cells and cell-based tissue engineering." Arthritis Res Ther. 2003; 5(1): 32-45.
Van Der Voort, R., et al. "Paracrine regulation of germinal center B cell adhesion through the c-met-hepatocyte growth factor/scatter factor pathway." J Exp Med. Jun. 16, 1997; 185(12): 2121-31.
Vanderkerken, K. et al. "Multiple myeloma biology: lessons from the 5TMM models." Immunol Rev. Aug. 2003; 194: 196-206.
Vanderkerken, K., et al. "The 5T2MM murine model of multiple myeloma: maintenance and analysis." Methods Mol Med. 2005; 113: 191-205.
Vijayaragavan, K., et al. "Noncanonical Wnt signaling orchestrates early developmental events toward hematopoietic cell fate from human embryonic stem cells." Cell Stem Cell. Mar. 6, 2009; 4(3): 248-62.
Weimar, I.S., et al. "Hepatocyte growth factor/scatter factor promotes adhesion of lymphoma cells to extracellular matrix molecules via alpha 4 beta 1 and alpha 5 beta 1 integrins." Blood. Feb. 1, 1997; 89(3): 990-1000.
Wells, A.D., et al. "Following the fate of individual T cells throughout activation and clonal expansion. Signals from T cell receptor and CD28 differentially regulate the induction and duration of a proliferative response." J Clin Invest. Dec. 15, 1997; 100(12): 3173-83.
Willert, J., et al. "A transcriptional response to Wnt protein in human embryonic carcinoma cells." BMC Dev Biol. Jul. 2, 2002; 2: 8.
Yaccoby, S. "Advances in the understanding of myeloma bone disease and tumour growth." Br J Haematol. May 2010; 149(3): 311-21.
Yaccoby, S., et al. "Antibody-based inhibition of DKK1 suppresses tumor-induced bone resorption and multiple myeloma growth in vivo." Blood. Mar. 1, 2007; 109(5): 2106-11.
Yaccoby, S., et al. "Antimyeloma efficacy of thalidomide in the SCID-hu model" Blood. Dec. 1, 2002; 100(12): 4162-8.
Yaccoby, S., et al. "Myeloma interacts with the bone marrow microenvironment to induce osteoclastogenesis and is dependent on osteoclast activity." Br J Haematol. Feb. 2002; 116(2): 278-90.
Yata, K., et al. "The SCID-rab model: a novel in vivo system for primary human myeloma demonstrating growth of CD138-expressing malignant cells." Leukemia. Nov. 2004; 18(11): 1891-7.
Ye, B.H., et al. "Alterations of a zinc finger-encoding gene, BCL-6, in diffuse large-cell lymphoma." Science. Oct. 29, 1993; 262(5134): 747-50.
Zilberberg, J., et al. "Novel approach for predicting GVHD reactive T cells using V beta spectratype analysis of dividing CFSE-labeled

(56) References Cited

OTHER PUBLICATIONS

T cells from a mixed lymphocyte reaction." Biol Blood Marrow Transplant (ASBMT). Feb. 2007; 13(2, Supp.): 106.
Zilberberg, J., et al. "Treatment with GM-CSF secreting myeloid leukemia cell vaccine prior to autologous-BMT improves the survival of leukemia-challenged mice." Biol Blood Marrow Transplant. Mar. 2011; 17(3): 330-40.
Zlei, M., et al. "Characterization of in vitro growth of multiple myeloma cells." Exp Hematol. Oct. 2007; 35(10): 1550-61.
Gimble JM, "The Function of Adipocytes in the Bone Marrow Stroma" New Biol., Apr. 1990; 2(4): 304-312.
Matsumoto, K. et al, "Growth factor regulation of integrin-mediated cell motility"; Cancer Metastasis Rev. 14: 205-217(1995).
Allen CD, et al.; "Germinal-CenterOrganizationandCellularDynamics"; Immunity. 2007; 27:190-202.
Ye BH, et al.; "Alterations of a Zinc Finger-Encoding Gene, BCL-6, in Diffuse Large-Cell Lymphoma"; Science, 1993;262:747-750.
Loberg, RD, et al.; "Enhanced Glycogen Synthase Kinase-3b Activity Mediates Hypoxia-induced Apoptosis of Vascular Smooth Muscle Cells and Is Prevented by Glucose Transport and Metabolism"; J. Biol. Chem. 277 (44): 41667-673 (2002).
Zver, S. et al.; "Cardiac Toxicity of High-Dose Cyclophosphamide in Patients with Multiple Myeloma Undergoing Autologous Hematopoietic Stem Cell Transplantation"; Intl J. Hematol. 85(5): 408-14 (2007).

\* cited by examiner

Fig. 3a
Adhesion and spreading
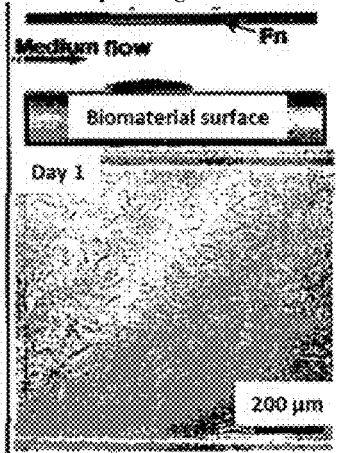
Fig. 3b
Confluent on bottom surface
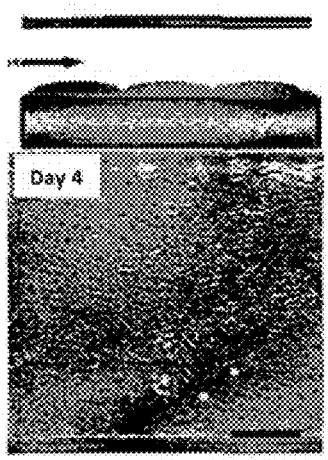
Fig. 3c
Migration to top surface and formation of multiple layers
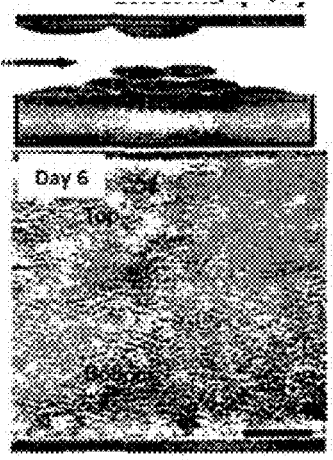
Fig. 3d
Formation of 3-D nodular structures
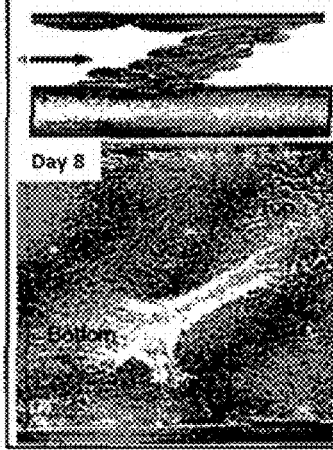
Fig. 3e Re-structuring 3-D tissue-like structures with evidence of mineralization
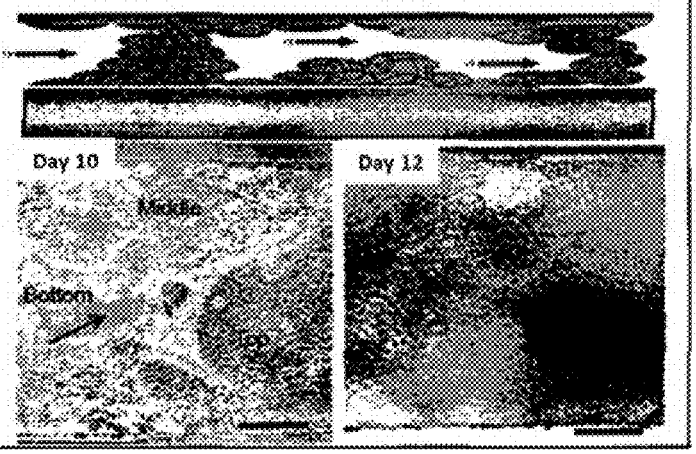

For each of 3 different patient's BM culture: do flow for 2 chambers of each set at a time.
Culture medium: 10% patient's serum, 0.8ul/min Harvest on day 7          Harvest on day 21

Experiment procedure
- Culture BM cell and do flow cytomtry on day 7 and day 21 at Hackensack;
- Monitor BM cell development on 3D bone tissue; Take pictures on 0,7 ,21 days at Stevens.

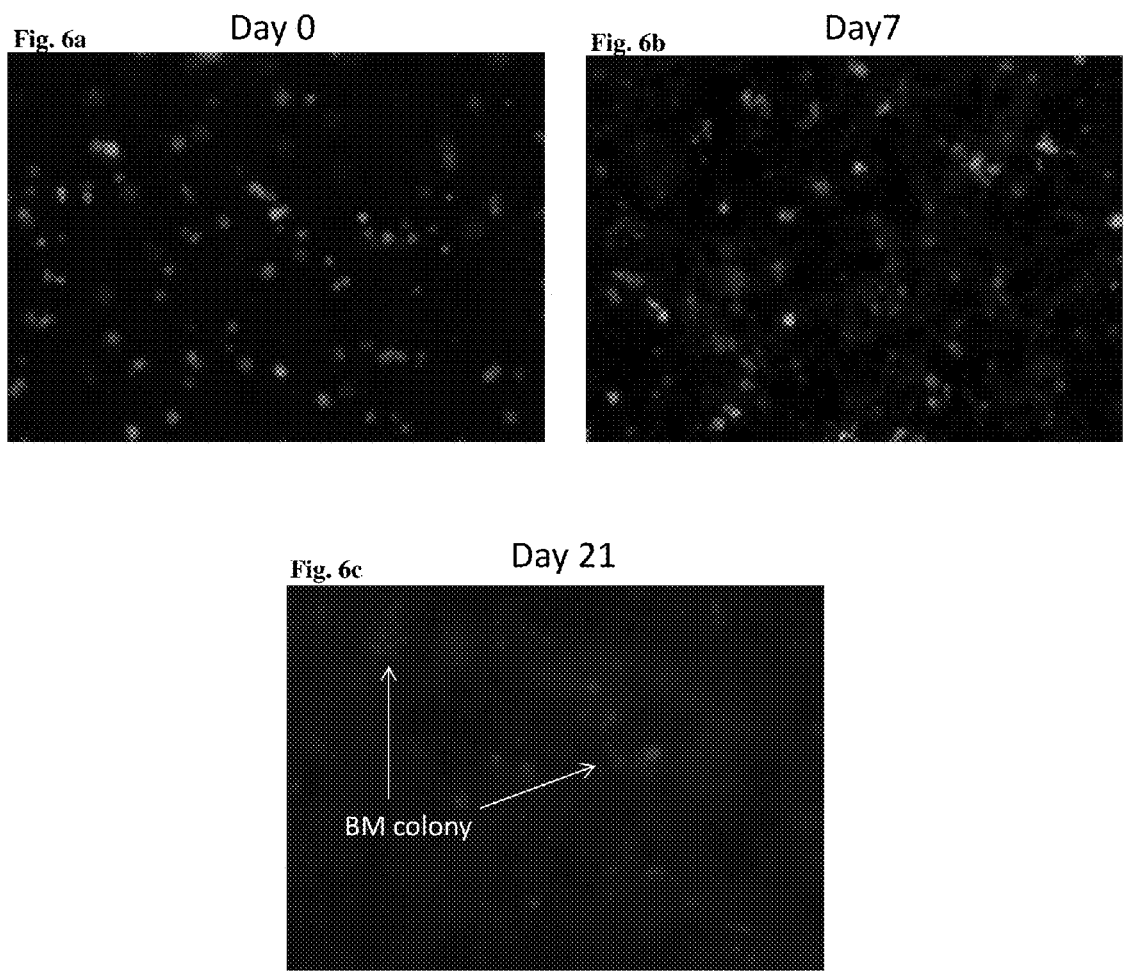

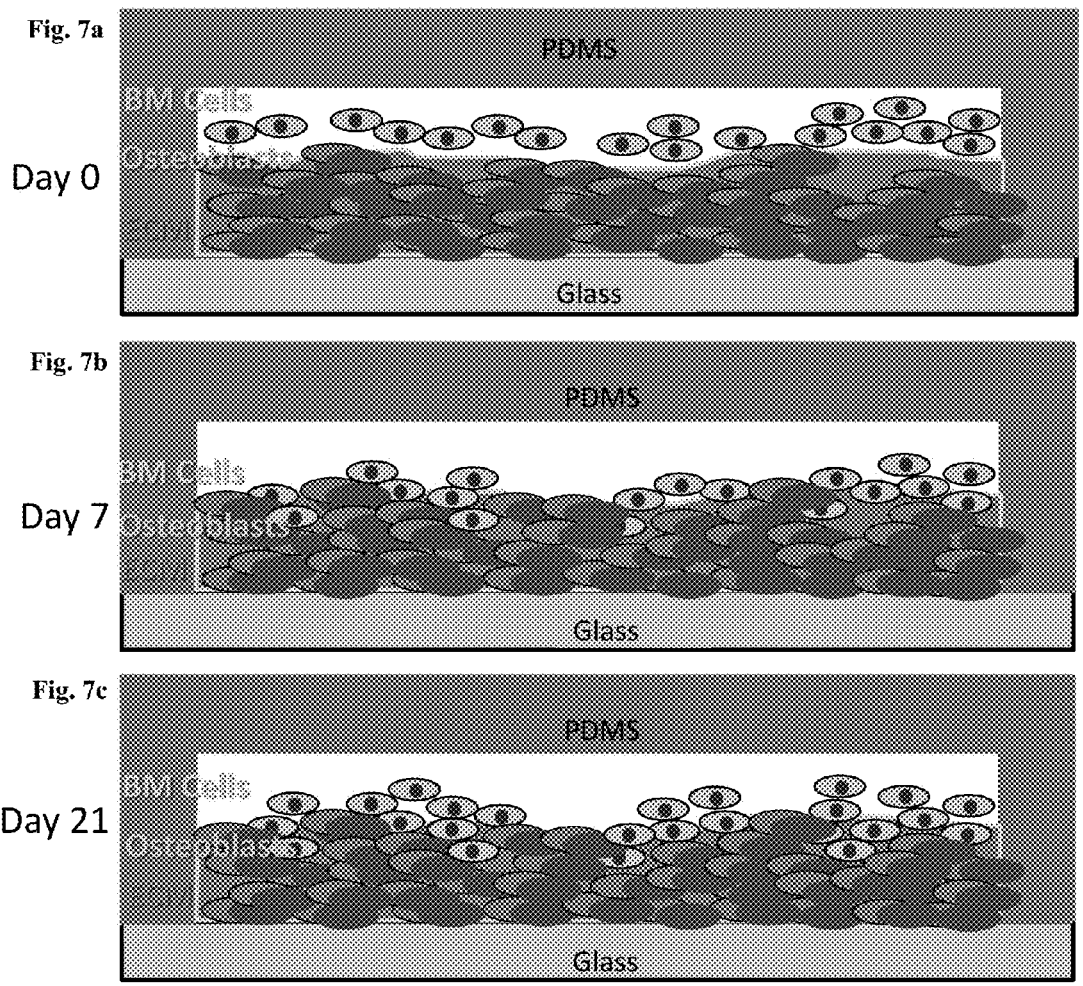

EX VIVO HUMAN MULTIPLE MYELOMA CANCER NICHE AND ITS USE AS A MODEL FOR PERSONALIZED TREATMENT OF MULTIPLE MYELOMA

CROSS REFERENCE TO RELATED APPLICATIONS

This application is a divisional application and claims the benefit of allowed U.S. patent application Ser. No. 13/827,170 filed Mar. 14, 2013, and entitled "An Ex Vivo Human Multiple Myeloma Cancer Niche and its Use as a Model for personalized Treatment of Multiple Myeloma", which is incorporated by reference herein in its entirety.

FIELD OF THE INVENTION

The described invention generally relates to ex vivo propagation and maintenance of human monoclonal gammopathy cells in a dynamic microfluidic ex vivo system and its use as a model system for personalized treatment thereof.

BACKGROUND OF THE INVENTION

Tissue Compartments, Generally

In multicellular organisms, cells that are specialized to perform common functions are usually organized into cooperative assemblies embedded in a complex network of secreted extracellular macromolecules, the extracellular matrix (ECM), to form specialized tissue compartments. Individual cells in such tissue compartments are in contact with ECM macromolecules. The ECM helps hold the cells and compartments together and provides an organized lattice or construct within which cells can migrate and interact with one another. In many cases, cells in a compartment can be held in place by direct cell-cell adhesion. In vertebrates, such compartments may be of four major types, a connective tissue (CT) compartment, an epithelial tissue (ET) compartment, a muscle tissue (MT) compartment and a nervous tissue (NT) compartment, which are derived from three embryonic germ layers: ectoderm, mesoderm and endoderm. The NT and portions of the ET compartments are differentiated from the ectoderm; the CT, MT and certain portions of the ET compartments are derived from the mesoderm; and further portions of the ET compartment are derived from the endoderm.

The Bone Marrow Niche

The term "niche" as used herein refers to a specialized regulatory microenvironment, consisting of components which control the fate specification of stem and progenitor cells, as well as maintaining their development by supplying the requisite factors. The term "bone marrow (BM) niche" as used herein refers to a well-organized architecture composed of osteoblasts, osteoclasts, bone marrow endothelial cells, stromal cells, adipocytes and extracellular matrix proteins (ECM). These elements play an essential role in the survival, growth and differentiation of diverse lineages of blood cells.

Bone marrow consists of a variety of precursor and mature cell types, including hematopoietic cells (the precursors of mature blood cells) and stromal cells (the precursors of a broad spectrum of connective tissue cells), both of which appear to be capable of differentiating into other cell types. The mononuclear fraction of bone marrow contains stromal cells, hematopoietic precursors, and endothelial precursors.

Extracellular Matrix (ECM) Proteins

The ECM is a complex structural entity surrounding and supporting cells found within mammalian tissues. The ECM is comprised of proteoglycans (e.g., heparan sulfate, chondroitin sulfate, keratin sulfate, hyaluronic acid), collagen, fibronectin, laminin and elastin. Most mammalian cells cannot survive unless they are anchored to the ECM. Cells attach to the ECM via transmembrane glycoproteins (e.g., integrins) which bind to various types of ECM proteins (e.g., collagens, laminins, fibronectin).

Adipocytes

Adipocytes of the bone marrow stroma provide the cytokines and extracellular matrix proteins required for the maturation and proliferation of the circulating blood cells. Due to the complexity of the bone marrow as an organ, the normal physiology of these stromal cells is not well understood. In particular, the role of adipocytes in the bone marrow remains controversial. Cloned bone marrow stromal cell lines provide an in vitro model for analysis of the lympho-hematopoietic microenvironment. These cells may be capable of multiple differentiation pathways, assuming the phenotype of adipocytes, chondrocytes, myocytes, and osteocytes in vitro. (Gimble J M, New Biol., 1990 April; 2(4): 304-312).

Hematopoietic Stem Cells Development and Maintenance

Hematopoietic stem cells (HSCs) (also known as the colony-forming unit of the myeloid and lymphoid cells (CFU-M,L), or CD34+ cells) are rare pluripotential cells within the blood-forming organs that are responsible for the continued production of blood cells during life. While there is no single cell surface marker exclusively expressed by hematopoietic stem cells, it generally has been accepted that human HSCs have the following antigenic profile: CD 34+, CD59+, Thy1+ (CD90), CD38low/−, C-kit−/low and, lin− (Chotinantakul, K. and Leeanansaksiri, W., Bone Marrow Research, Vol. 2012, Article ID 270425; The National Institutes of Health, Resource for Stem Cell Research, http://stemcells.nih.gov/info/scireport/pages/chapter5.aspx).

CD45 is also a common marker of HSCs, except platelets and red blood cells (The National Institutes of Health, Resource for Stem Cell Research, http://stemcells.nih.gov/info/scireport/pages/chapter5.aspx). HSCs can generate a variety of cell types, including erythrocytes, neutrophils, basophils, eosinophils, platelets, mast cells, monocytes, tissue macrophages, osteoclasts, and the T and B lymphocytes (The National Institutes of Health, Resource for Stem Cell Research, http://stemcells.nih.gov/info/scireport/pages/chapter5.aspx). The regulation of hematopoietic stem cells is a complex process involving self-renewal, survival and proliferation, lineage commitment and differentiation and is coordinated by diverse mechanisms including intrinsic cellular programming and external stimuli, such as adhesive interactions with the microenvironmental stroma and the actions of cytokines (Chotinantakul, K. and Leeanansaksiri, W., Bone Marrow Research, Vol. 2012, Article ID 270425; The National Institutes of Health, Resource for Stem Cell Research, http://stemcells.nih.gov/info/scireport/pages/chapter5.aspx).

Different paracrine factors are important in causing hematopoietic stem cells to differentiate along particular pathways. Paracrine factors involved in blood cell and lymphocyte formation are called cytokines. Cytokines can be made by several cell types, but they are collected and concentrated by the extracellular matrix of the stromal (mesenchymal) cells at the sites of hematopoiesis (Majumdar, M. K. et al., J. Hematother. Stem Cell Res. 2000 December; 9(6): 841-848). For example, granulocyte-macrophage colony-stimulating factor (GM-CSF) and the multilineage growth factor IL-3 both bind to the heparan sulfate glycosaminoglycan of the bone marrow stroma (Burdon, T. J., et al., Bone Marrow Research, Volume 2011, Article ID 207326; Baraniak, P. R. and McDevitt, T. C., Regen. Med. 2010 January; 5(1): 121-143). The extracellular matrix then presents these factors to the stem cells in concentrations high enough to bind to their receptors.

Mesenchymal Stem Cells (MSCs)

Mesenchymal stem cells (MSCs) (also known as bone marrow stromal stem cells or skeletal stem cells) are non-blood adult stem cells found in a variety of tissues. They are characterized by their spindle-shape morphologically; by the expression of specific markers on their cell surface; and by their ability, under appropriate conditions, to differentiates along a minimum of three lineages (osteogenic, chondrogenic, and adipogenic) (Minguell, J. J., et al., Experimental Biology and Medicine 2001, 226: 507-520; Tuan, R. S., et al., Arthritis Res. Ther. DOI: 10.1186/ar614).

No single marker that definitely delineates MSCs in vivo has been identified due to the lack of consensus regarding the MSC phenotype, but it generally is considered that MSCs are positive for cell surface markers CD105, CD166, CD90, and CD44 and that MSCs are negative for typical hematopoietic antigens, such as CD45, CD34, and CD14 (Minguell, J. J., et al., Experimental Biology and Medicine 2001, 226: 507-520; Lee, H. J., et al., Arthritis & Rheumatism, Vol. 60, No. 8, August 2009, pp. 2325-2332; Kolf, C. M., et al., Arthritis Research & Therapy 2007, 9:204, DOI: 10.1186/ar2116). As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic-supporting stroma (Gimbel, J. M., et al., Transfus. Med. Hemother. 2008; 35: 228-238; Minguell, J. J., et al., Experimental Biology and Medicine 2001, 226: 507-520; Kolf, C. M., et al., Arthritis Research & Therapy 2007, 9:204, DOI: 10.1186/ar2116). Studies using transgenic and knockout mice and human musculoskeletal disorders have reported that MSC differentiate into multiple lineages during embryonic development and adult homeostasis (Komine, A., et al., Biochem. Biophys. Res. Commun. 2012 Oct. 5; 426(4): 468-474; Shen, J., et al., Scientific Reports, 1:67, DOI: 10.1038/srep00067; Reiser, J., et al., Expert. Opin. Biol. Ther. 2005 December; 5(12): 1571-1584).

Analyses of the in vitro differentiation of MSCs under appropriate conditions that recapitulate the in vivo process have led to the identification of various factors essential for stem cell commitment. Among them, secreted molecules and their receptors (e.g., transforming growth factor-β), extracellular matrix molecules (e.g., collagens and proteoglycans), the actin cytoskeleton, and intracellular transcription factors (e.g., Cbfa1/Runx2, PPAR, Sox9, and MEF2) have been shown to play important roles in driving the commitment of multipotent MSCs into specific lineages, and maintaining their differentiated phenotypes (Kolf, C. M., et al., Arthritis Research & Therapy 2007, 9:204, DOI: 10.1186/ar2116).

For example, it has been shown that osteogenesis of MSCs, both in vitro and in vivo, involves multiple steps and the expression of various regulatory factors. During osteogenesis, multipotent MSCs undergo asymmetric division and generate osteoprecursors, which then progress to form osteoprogenitors, preosteoblasts, functional osteoblasts, and eventually osteocytes (Bennett, K. P., et al., BMC Genomics 2007, 8:380, DOI: 10.1186/1471-2164-8-380). This progression from one differentiation stage to the next is accompanied by the activation and subsequent inactivation of transcription factors, i.e., Cbfa1/Runx2, Msx2, Dlx5, Osx, and expression of bone-related marker genes, i.e., osteopontin, collagen type I, alkaline phosphatase, bone sialoprotein, and osteocalcin (Bennett, K. P., et al., BMC Genomics 2007, 8:380, DOI: 10.1186/1471-2164-8-380, Ryoo, H. M., et al., Mol. Endo. 1997, Vol. 11, No. 11, pp. 1681-1694; Hou, Z. et al., Proc. Natl. Acad. Sci., Vol. 96, pp. 7294-7299, June 1999; Engler, A. J., et al., Cell 126, 677-689, Aug. 25, 2006; Marom, R. et al., Journal of Cellular Physiology 202: 41-48 (2005)). Members of the Wnt family also have been shown to impact MSC osteogenesis. Wnts are a family of secreted cysteine-rich glycoproteins that have been implicated in the regulation of stem cell maintenance, proliferation, and differentiation during embryonic development. Canonical Wnt signaling increases the stability of cytoplasmic β-catenin by receptor-mediated inactivation of GSK-3 kinase activity and promotes β-catenin translocation into the nucleus (Liu, G., et al., JCB, Vol. 185, No. 1, 2009, pp. 67-75). The active β-catenin/TCF/LEF complex then regulates the transcription of genes involved in cell proliferation (Novak, A. and Dedhar, S., Cell. Mol. Life Sci. 1999 Oct. 30; 56(5-6): 523-537; Grove, E. A., Genes and Development 2011 25: 1759-1762). In humans, mutations in the Wnt co-receptor, LRP5, lead to defective bone formation (Krishnan, V., et al., The Journal of Clinical Investigation, Vol. 116, No. 5, May 2006, pp. 1202-1209). "Gain of function" mutation results in high bone mass, whereas "loss of function" causes an overall loss of bone mass and strength, indicating that Wnt signaling is positively involved in embryonic osteogenesis (Krishnan, V., et al., The Journal of Clinical Investigation, Vol. 116, No. 5, May 2006, pp. 1202-1209; Niziolek, P. J., et al., Bone 2011 November; 49(5): 1010-1019). Canonical Wnt signaling pathway also functions as a stem cell mitogen via stabilization of intracellular β-catenin and activation of the β-catenin/TCF/LEF transcription complex, resulting in activated expression of cell cycle regulatory genes, such as Myc, cyclin D1, and Msx1 (Willert, J., et al., BMC Development Biology 2002, 2:8, pp. 1-7). When MSCs are exposed to Wnt3a, a prototypic canonical Wnt signal, under standard growth medium conditions, they show markedly increased cell proliferation and a decrease in apoptosis, consistent with the mitogenic role of Wnts in hematopoietic stem cells (Almeida, M., et al., The Journal of Biological Chemistry, Vol. 280, No. 50, pp. 41342-41351, Dec. 16, 2005; Vijayaragavan, K., et al., Cell Stem Cell 4, 248-262, Mar. 6, 2009). However, exposure of MSCs to Wnt3a conditioned medium or overexpression of ectopic Wnt3a during osteogenic differentiation inhibits osteogenesis in vitro through β-catenin mediated down-regulation of TCF activity (Quarto, N., et al., Tissue Engineering: Part A, Vol. 16, No. 10, 2010, pp. 3185-3197). The expression of several osteoblast specific genes, e.g., alkaline phosphatase, bone sialoprotein, and osteocalcin, is dramatically reduced, while the expression of Cbfa1/Runx2, an early osteo-inductive transcription factor is not altered, implying that Wnt3a-mediated canonical signaling pathway is necessary, but not sufficient, to completely block MSC osteogenesis (Quarto, N., et al., Tissue Engineering: Part A, Vol. 16, No. 10, 2010, pp. 3185-3197; Eslaminejad, M. B. and Yazdi, P. E., Yakhteh Medical Journal, Vol. 9, No. 3, Autumn 2007, pp. 158-169). On the other hand, Wnt5a, a typical non-canonical Wnt member, has been shown to promote osteogenesis in vitro (Arnsdorf, E. J., et al., PLoS ONE, April 2009, Vol. 4, Issue 4, e5388, pp. 1-10; Baksh, D., et al., J. Cell. Physiol., 2007, 212: 817-826; J. Cell. Biochem., 2007, 101: 1109-1124).

Since Wnt3a promotes MSC proliferation during early osteogenesis, it is thought likely that canonical Wnt signaling functions in the initiation of early osteogenic commitment by increasing the number of osteoprecursors in the stem cell compartment, while non-canonical Wnt drives the progression of osteoprecursors to mature functional osteoblasts.

Soluble Factors

Hepatocyte Growth Factor/Scatter Factor (HGF/SF)

Hepatocyte growth factor/scatter factor (HGF/SF) is a multifunctional cytokine that promotes mitogenesis, migration, invasion and morphogenesis (Jian, W. G. and S. Hiscox, Histol. Histopathol. 2: 537-555 (1997). HGF/SF signaling modulates integrin function by promoting aggregation and cell adhesion. Morphogenic responses to HGF/SF are dependent on adhesive events. See Matsumoto, K. et al, Cancer Metastasis Rev. 14: 205-217 (1995). HGF/SF-induced effects occur via signaling of the MET tyrosine kinase receptor following ligand binding, which leads to enhanced integrin-mediated B cell and lymphoma cell adhesion. Galimi, F. et al, Stem Cells 2: 22-30 (1993); Van der Voort, R. et al., J. Exp. Med. 185: 2121-31 (1997); Weimar, I. S. et al., Blood 89: 990-1000 (1997).

Tumor Growth Factor (Also Known as Transforming Growth Factor)

The TGF-β1 superfamily of structurally related peptides includes the TGF-β isoforms, β1, β2, β3, and β5, the activins and the bone morphogenetic proteins (BMPs). TGF-β-like factors are a multifunctional set of conserved growth and differentiation factors that control biological processes such as embryogenesis, organogenesis, morphogenesis of tissues like bone and cartilage, vasculogenesis, wound repair and angiogenesis, hematopoiesis, and immune regulation. Signaling by ligands of the TGF-β superfamily is mediated by a high affinity, ligand-induced, heteromeric complex consisting of related Ser/Thr kinase receptors divided into two subfamilies, type I and type II. The type II receptor transphosphorylates and activates the type I receptor in a Gly/Ser-rich region. The type I receptor in turn phosphorylates and transduces signals to a novel family of recently identified downstream targets, termed Smads.

Osteoprotegerin and RANKL

The molecules osteoprotegerin (OPG) and Receptor activator of NF-κB (RANKL) play a role in the communication between osteoclasts and osteoblasts and are members of a ligand-receptor system that directly regulates osteoclast differentiation and bone resorption. Grimaud, E. et al, Am J. Pathol. 2021-2031 (2993). RANKL has been shown to both activate mature osteoclasts and mediate osteoclastogenesis in the presence of M-CSF, i.e., RANKL is essential for osteoclast differentiation via its receptor RANK located on the osteoclast membrane. OPG is a soluble decoy receptor that prevents RANKL from binding to and activating RANK. It also inhibits the development of osteoclasts and down-regulates the RANKL signaling through RANK. RANKL and OPG have been detected in bone pathological situations where osteolysis occurred. The RANKL/OPG ratio is increased and correlated with markers of bone resorption, osteolytic lesions, and markers of disease activity in multiple myeloma. Id.

Macrophage Colony-Stimulating Factor (M-CSF)

Macrophage colony-stimulating factor (M-CSF) is a hematopoietic growth factor that is involved in the proliferation, differentiation, and survival of monocytes, macrophages, and bone marrow progenitor cells. Stanley E R, Berg K L, Einstein D B, Lee P S, Pixley F J, Wang Y, Yeung Y G, Mol. Reprod. Dev. 46 (1): 4-10 (1997).

Macrophage inflammatory protein 1-alpha (MIP1α) is a member of the C-C subrfamily of chemokines, a large superfamily of low-molecular weight, inducible proteins that exhibits a variety of proinflammatory activities in vitro. The C-C chemokines generally are chemotactic for cells of the monocyte lineage and lymphocytes. In addition to its proinflammatory activities, MIP-alpha inhibits the proliferation of hematopoietic stem cells in vitro and in vivo. Cook, D. N., J. Leukocyte Biol. 59(1): 61-66 (1996).

Sclerostin

Sclerostin, a protein expressed by osteocytes, downregulates osteoblastic bone formation by interfering with Wnt signaling.

Osteogenesis or Ossification

Osteogenesis or ossification is a process by which the bones are formed. There are three distinct lineages that generate the skeleton. The somites generate the axial skeleton, the lateral plate mesoderm generates the limb skeleton, and the cranial neural crest gives rise to the branchial arch, craniofacial bones, and cartilage. There are two major modes of bone formation, or osteogenesis, and both involve the transformation of a preexisting mesenchymal tissue into bone tissue. The direct conversion of mesenchymal tissue into bone is called intramembranous ossification. The process by which mesenchymal cells differentiate into cartilage, which is later replaced by bone cells is called endochondral ossification.

Intramembranous Ossification

Intramembraneous ossification is the characteristic way in which the flat bones of the scapula, the skull and the turtle shell are formed. In intramembraneous ossification, bones develop sheets of fibrous connective tissue. During intramembranous ossification in the skull, neural crest-derived mesenchymal cells proliferate and condense into compact nodules. Some of these cells develop into capillaries; others change their shape to become osteoblasts, committed bone precursor cells. The osteoblasts secrete a collagen-proteoglycan matrix that is able to bind calcium salts. Through this binding, the prebone (osteoid) matrix becomes calcified. In most cases, osteoblasts are separated from the region of calcification by a layer of the osteoid matrix they secrete. Occasionally, osteoblasts become trapped in the calcified matrix and become osteocytes. As calcification proceeds, bony spicules radiate out from the region where ossification began, the entire region of calcified spicules becomes surrounded by compact mesenchymal cells that form the periosteum, and the cells on the inner surface of the periosteum also become osteoblasts and deposit osteoid matrix parallel to that of the existing spicules. In this manner, many layers of bone are formed.

Intramembraneous ossification is characterized by invasion of capillaries into the mesenchymal zone, and the emergence and differentiation of mesenchymal cells into mature osteoblasts, which constitutively deposit bone matrix leading to the formation of bone spicules, which grow and develop, eventually fusing with other spicules to form trabeculae. As the trabeculae increase in size and number they become interconnected forming woven bone (a disorganized weak structure with a high proportion of osteocytes), which eventually is replaced by more organized, stronger, lamellar bone.

The molecular mechanism of intramembranous ossification involves bone morphogenetic proteins (BMPs) and the activation of a transcription factor called CBFA1. Bone morphogenetic proteins, for example, BMP2, BMP4, and BMP7, from the head epidermis are thought to instruct the neural crest-derived mesenchymal cells to become bone cells directly. BMPs activate the Cbfa1 gene in mesenchymal cells. The CBFA1 transcription factor is known to transform mesenchymal cells into osteoblasts. Studies have shown that the mRNA for mouse CBFA1 is largely restricted to the mesenchymal condensations that form bone, and is limited to the osteoblast lineage. CBFA1 is known to activate the genes for osteocalcin, osteopontin, and other bone-specific extracellular matrix proteins.

Endochondral Ossification (Intracartilaginous Ossification)

Endochondral ossification, which involves the in vivo formation of cartilage tissue from aggregated mesenchymal cells, and the subsequent replacement of cartilage tissue by bone, can be divided into five stages. The skeletal components of the vertebral column, the pelvis, and the limbs are first formed of cartilage and later become bone.

First, the mesenchymal cells are committed to become cartilage cells. This commitment is caused by paracrine factors that induce the nearby mesodermal cells to express two transcription factors, Pax1 and Scleraxis. These transcription factors are known to activate cartilage-specific genes. For example, Scleraxis is expressed in the mesenchyme from the sclerotome, in the facial mesenchyme that forms cartilaginous precursors to bone, and in the limb mesenchyme.

During the second phase of endochondral ossification, the committed mesenchyme cells condense into compact nodules and differentiate into chondrocytes (cartilage cells that produce and maintain the cartilaginous matrix, which consists mainly of collagen and proteoglycans). Studies have shown that N-cadherin is important in the initiation of these condensations, and N-CAM is important for maintaining them. In humans, the SOX9 gene, which encodes a DNA-binding protein, is expressed in the precartilaginous condensations.

During the third phase of endochondral ossification, the chondrocytes proliferate rapidly to form the model for bone. As they divide, the chondrocytes secrete a cartilage-specific extracellular matrix.

In the fourth phase, the chondrocytes stop dividing and increase their volume dramatically, becoming hypertrophic chondrocytes. These large chondrocytes alter the matrix they produce (by adding collagen X and more fibronectin) to enable it to become mineralized by calcium carbonate.

The fifth phase involves the invasion of the cartilage model by blood vessels. The hypertrophic chondrocytes die by apoptosis, and this space becomes bone marrow. As the cartilage cells die, a group of cells that have surrounded the cartilage model differentiate into osteoblasts, which begin forming bone matrix on the partially degraded cartilage. Eventually, all the cartilage is replaced by bone. Thus, the cartilage tissue serves as a model for the bone that follows.

The replacement of chondrocytes by bone cells is dependent on the mineralization of the extracellular matrix. A number of events lead to the hypertrophy and mineralization of the chondrocytes, including an initial switch from aerobic to anaerobic respiration, which alters their cell metabolism and mitochondrial energy potential. Hypertrophic chondrocytes secrete numerous small membrane-bound vesicles into the extracellular matrix. These vesicles contain enzymes that are active in the generation of calcium and phosphate ions and initiate the mineralization process within the cartilaginous matrix. The hypertrophic chondrocytes, their metabolism and mitochondrial membranes altered, then die by apoptosis.

In the long bones of many mammals (including humans), endochondral ossification spreads outward in both directions from the center of the bone. As the ossification front nears the ends of the cartilage model, the chondrocytes near the ossification front proliferate prior to undergoing hypertrophy, pushing out the cartilaginous ends of the bone. The cartilaginous areas at the ends of the long bones are called epiphyseal growth plates. These plates contain three regions: a region of chondrocyte proliferation, a region of mature chondrocytes, and a region of hypertrophic chondrocytes. As the inner cartilage hypertrophies and the ossification front extends farther outward, the remaining cartilage in the epiphyseal growth plate proliferates. As long as the epiphyseal growth plates are able to produce chondrocytes, the bone continues to grow.

Bone Remodeling

Bone constantly is broken down by osteoclasts and re-formed by osteoblasts in the adult. This process of renewal is known as bone remodeling. The balance in this dynamic process shifts as people grow older: in youth, it favors the formation of bone, but in old age, it favors resorption.

As new bone material is added peripherally from the internal surface of the periosteum, there is a hollowing out of the internal region to form the bone marrow cavity. This destruction of bone tissue is due to osteoclasts that enter the bone through the blood vessels. Osteoclasts dissolve both the inorganic and the protein portions of the bone matrix. Each osteoclast extends numerous cellular processes into the matrix and pumps out hydrogen ions onto the surrounding material, thereby acidifying and solubilizing it. The blood vessels also import the blood-forming cells that will reside in the marrow for the duration of the organism's life.

The number and activity of osteoclasts must be tightly regulated. If there are too many active osteoclasts, too much bone will be dissolved, and osteoporosis will result. Conversely, if not enough osteoclasts are produced, the bones are not hollowed out for the marrow, and osteopetrosis (known as stone bone disease, a disorder whereby the bones harden and become denser) will result.

Lymphocytes and the Immune Response

Multicellular organisms have developed two defense mechanisms to fight infection by pathogens: innate and adaptive immune responses. Innate immune responses are triggered immediately after infection and are independent of the host's prior exposure to the pathogen. Adaptive immune responses operate later in an infection and are highly specific for the pathogen that triggered them. The function of adaptive immune responses is to destroy the invading pathogens and any toxic molecules they produce. ("Chapter 24: The adaptive immune system," Molecular Biology of the Cell, Alberts, B. et al., Garland Science, N Y, 2002).

The immune system consists of a wide range of distinct cell types, amongst which white blood cells called lymphocytes play a central role in determining immune specificity. Other cells, such as monocytes, macrophages, dendritic cells, Langerhans' cells, natural killer (NK) cells, mast cells, basophils, and other members of the myeloid lineage of cells, interact with the lymphocytes and play critical functions in antigen presentation and mediation of immunologic functions. (Paul, W. E., "Chapter 1: The immune system: an introduction," Fundamental Immunology, 4th Edition, Ed. Paul, W. E., Lippicott-Raven Publishers, Philadelphia (1999)).

Lymphocytes are found in central lymphoid organs, the thymus, and bone marrow, where they undergo developmental steps that enable them to orchestrate immune responses. A large portion of lymphocytes and macrophages comprise a recirculating pool of cells found in the blood and lymph, providing the means to deliver immunocompetent cells to localized sites in need. (Paul, W. E., "Chapter 1: The immune system: an introduction," Fundamental Immunology, 4th Edition, Ed. Paul, W. E., Lippicott-Raven Publishers, Philadelphia (1999)).

Lymphocytes are specialized cells, committed to respond to a limited set of structurally related antigens. This commitment, which exists before the first contact of the immune system with a given antigen, is expressed by the presence on the lymphocyte's surface of receptors that are specific for specific determinants or epitopes on the antigen. Each lymphocyte possesses a population of cell-surface receptors, all of which have identical combining regions. One set of lymphocyte, referenced to as a "clone" differs from another in the structure of the combining region of its receptors, and thus differs in the epitopes being recognized. The ability of an organism to respond to any nonself antigen is achieved by large number of different clones of lymphocytes, each bearing receptors specific for a distinct epitope. (Paul, W. E., "Chapter 1: The immune system: an introduction," Fundamental Immunology, 4th Edition, Ed. Paul, W. E., Lippicott-Raven Publishers, Philadelphia (1999)).

The adaptive immune system is composed of millions of lymphocyte clones. The diversity of lymphocytes is such that even a single antigenic determinant is likely to activate many clones, each of which produces an antigen-binding site with its own characteristic affinity for the determinant. Molec. Biol. Of the Cell, 1369). When many clones are activated, such responses are said to be polyclonal; when only a few clones are activated, the response is said to be oligoclonal, and when the response involves only a single B or T cell clone, it is said to be monoclonal.

There are two broad classes of adaptive immune responses that are carried out by different classes of lymphocytes: antibody responses mediated by B-lymphocytes (or B-cells); and cell-mediated immune responses carried out by T-lymphocytes (or T-cells). B-cells are bone-marrow-derived and are precursors of immunoglobulin- (Ig-) or antibody-expressing cells while T-cells are thymus-derived. (Paul, W. E., "Chapter 1: The immune system: an introduction," Fundamental Immunology, 4th Edition, Ed. Paul, W. E., Lippicott-Raven Publishers, Philadelphia (1999)).

Primary immune responses are initiated by the encounter of an individual with a foreign antigenic substance, generally an infectious microorganism. The infected individual responds with the production of immunoglobulin (Ig) molecules specific for the antigenic determinants of the immunogen and with the expansion and differentiation of antigen-specific regulatory and effector T-lymphocytes. The latter include both T-cells that secrete cytokines as well as natural killer T-cells that are capable of lysing the cell. (Paul, W. E., "Chapter 1: The immune system: an introduction," Fundamental Immunology, 4th Edition, Ed. Paul, W. E., Lippicott-Raven Publishers, Philadelphia (1999)).

As a consequence of the initial response, the immunized individual develops a state of immunologic memory. If the same (or closely related) microorganism or foreign object is encountered again, a secondary response is triggered. This generally consists of an antibody response that is more rapid and greater in magnitude than the primary (initial) response and is more effective in clearing the microbe from the body. A similar and more effective T-cell response then follows. The initial response often creates a state of immunity such that the individual is protected against a second infection, which forms the basis for immunizations. (Paul, W. E., "Chapter 1: The immune system: an introduction," Fundamental Immunology, 4th Edition, Ed. Paul, W. E., Lippicott-Raven Publishers, Philadelphia (1999)).

The immune response is highly specific. Primary immunization with a given microorganism evokes antibodies and T-cells that are specific for the antigenic determinants or epitopes found on that microorganism but that usually fail to recognize (or recognize only poorly) antigenic determinants of unrelated microbes. (Paul, W. E., "Chapter 1: The immune system: an introduction," Fundamental Immunology, 4th Edition, Ed. Paul, W. E., Lippicott-Raven Publishers, Philadelphia (1999)).

B-Lymphocytes:

B lymphocytes are a population of cells that express clonally diverse cell surface immunoglobulin (Ig) receptors recognizing specific antigenic epitopes.

B-lymphocytes are derived from hematopoietic stem cells by a complex set of differentiation events. The molecular events through which committed early members of the B lineage develop into mature B lymphocytes occur in fetal liver, and in adult life occur principally in the bone marrow. Interaction with specialized stromal cells and their products, including cytokines, such as interleukin IL-7, are critical to the normal regulation of this process. Tucker W. LeBien and Thomas F. Tedder, How they develop and function, Blood 112 (5): 1570-80 (2008). The phenotype of B cells generated with fetal liver is distinct from that using comparable precursors isolated from adult bone marrow. Richard R. Hardy and Kyoko Hayakawa, B Cell Development Pathways, Ann. Rev. Immunol. 19: 595-621 (2001).

Early B-cell development is characterized by the ordered rearrangement of Ig H and L chain loci, and Ig proteins themselves play an active role in regulating B-cell development.

Pre-B cells arise from progenitor (pro-B) cells that express neither the pre-B cell receptor (pre-BCR) or surface immunoglobulin (Ig).

Plasma cells, the critical immune effector cells dedicated to secretion of antigen-specific immunoglobulin (Ig) develop at three distinct stages of antigen-driven B cell development. Short-lived plasma cells emerge in response to both T-independent and T-dependent antigens. TD antigens also induce a germinal center (GC) pathway involving somatic hypermutation, affinity maturation, and production of memory B cells and long-lived PCs. Post-GC PCs have extended half-lives, produce high affinity antibody, and reside preferentially in the bone marrow. Memory B cells rapidly expand and differentiate into PCs in response to antigen challenge. Shapiro-Shelef, et al, Blimp-1 is required for the formation of immunoglobulin secreting plasma cells and pre-plasma memory B cells, Immunity 19: 607-20 (2003)

Antigen-induced B-cell activation and differentiation in secondary lymphoid tissues are mediated by dynamic changes in gene expression that give rise to the germinal center (GC) reaction (see section on B-cell maturation). Tucker W. LeBien and Thomas F. Tedder, How they develop and function, Blood 112 (5): 1570-80 (2008). The GC reaction is characterized by clonal expansion, class switch recombination (CSR) at the IgH locus, somatic hypermutation (SHM) of VH genes, and selection for increased affinity of a BCR for its unique antigenic epitope through affinity maturation.

Lymphocyte development requires the concerted action of a network of cytokines and transcription factors that positively and negatively regulate gene expression. Marrow stromal cell-derived interleukin-7 (IL-7) is a nonredundant cytokine for murine B-cell development that promotes V to DJ rearrangement and transmits survival/proliferation signals.

FLT3-ligand and TSLP play important roles in fetal B-cell development.

The cytokine(s) that regulate human B-cell development are not as well understood, and the cytokine (or cytokines) that promote marrow B-cell development at all stages of human life remains unknown.

At least 10 distinct transcription factors regulate the early stages of B-cell development, with E2A, EBF, and Pax5 being particularly important in promoting B-lineage commitment and differentiation.

Pax5, originally characterized by its capacity to bind to promoter sequences in Ig loci, may be the most multifunctional transcription factor for B cells. Pax5-deficient pro-B cells harbor the capacity to adapt non-B-lineage fates and develop into other hematopoietic lineages (Nutt S L, Heavey B, Rolink A G, Busslinger M., Nature. 1999; 401:556-562). Pax5 also regulates expression of at least 170 genes, a significant number of them important for B-cell signaling, adhesion, and migration of mature B cells (Cobaleda C, Schebesta A, Delogu A, Busslinger M., Nat Immunol. 2007; 8: 463-470). Conditional Pax5 deletion in mature murine B cells can result in dedifferentiation to an uncommitted hematopoietic progenitor and subsequent differentiation into T-lineage cells under certain conditions (Cobaleda C, Jochum W, Busslinger M., Nature. 2007; 449:473-477).

B lymphocyte induced maturation protein (Blimp-1), a transcriptional repressor, a 98 kDa protein containing five zinc finger motifs, has been implicated in plasma cell differentiation, and is required for the complete development of the pre-plasma memory B cell compartment. Shapiro-Shelef, et al, Blilmp-1 is required for the formation of immunoglobulin secreting plasma cells and pre-plasma memory B cells, Immunity 19: 607-20 (2003).

B Cell Specific Cell Surface Molecules:

Table 1 shows Cell surface CD molecules that are preferentially expressed by B cells. Tucker W. LeBien and Thomas F. Tedder, How they develop and function, Blood 112 (5): 1570-80 (2008):

TABLE 1

| Name | Original name | Cellular Reactivity | Structure |
| --- | --- | --- | --- |
| CD19 | B4 | Pan-B cell, follicular dendritic cells | Ig superfamily |
| CD20 | B1 | Mature B cells | MS4A family |
| CD21 | B2, HB-5 | Mature B cells, FDCs | Complement receptor family |
| CD22 | BL-CAM, Lyb-8 | Mature B cells | Ig superfamily |
| CD23 | FcεRII | Activated B cells, FDCs, others | C-type lectin |
| CD24 | BA-1, HB-6 | Pen-B cell, granulocytes, epithelial cells | GPI anchored |
| CD40 | Bp50 | B cells, epithelial cells, FDCs, others | TNF receptor |
| CD72 | Lyb-2 | Pam-B cell | C-type lectin |
| CD79 a, b | Igε,β | Surface Ig+ B cells | Ig superfamily |

CD19 is expressed by essentially all B-lineage cells and regulates intracellular signal transduction by amplifying Src-family kinase activity. CD20 is a mature B cell-specific molecule that functions as a membrane-embedded Ca2+ channel. Importantly, ritixumab, the first mAb approved by the Food and Drug Administration (FDA) for clinical use in cancer therapy (eg, follicular lymphoma), is a chimeric CD20 mAb.

CD21 is the C3d and Epstein-Barr virus receptor that interacts with CD19 to generate transmembrane signals and inform the B cell of inflammatory responses within microenvironments.

CD22 functions as a mammalian lectin for α2,6-linked sialic acid that regulates follicular B-cell survival and negatively regulates signaling.

CD23 is a low-affinity receptor for IgE expressed on activated B cells that influences IgE production.

CD24 was among the first pan-B-cell molecules to be identified, but this unique GPI-anchored glycoprotein's function remains unknown.

CD40 serves as a critical survival factor for GC B cells and is the ligand for CD154 expressed by T cells.

CD72 functions as a negative regulator of signal transduction and as the B-cell ligand for Semaphorin 4D (CD100).

There may be other unidentified molecules preferentially expressed by B cells, but the cell surface landscape is likely dominated by molecules shared with multiple leukocyte lineages.

B-Cell Maturation and Subset Development

Outside the marrow, B cells are morphologically homogenous, but their cell surface phenotypes, anatomic localization, and functional properties reveal still-unfolding complexities. Immature B cells exiting the marrow acquire cell surface IgD as well as CD21 and CD22, with functionally important density changes in other receptors. Immature B cells are also referred to as "transitional" (T1 and T2) based on their phenotypes and ontogeny, and have been characterized primarily in the mouse (Chung J B, Silverman M, Monroe J G., Trends Immunol. 2003; 24:343-349). Immature B cells respond to T cell-independent type 1 antigens such as lipopolysaccharides, which elicit rapid antibody responses in the absence of MHC class II-restricted T-cell help (Coutinho A, Moller G., Adv Immunol. 1975; 21:113-236). The majority of mature B cells outside of the gut associated lymphoid tissue (GALT) reside within lymphoid follicles of the spleen and lymph nodes, where they encounter and respond to T cell-dependent foreign antigens bound to follicular dendritic cells (DCs), proliferate, and either differentiate into plasma cells or enter GC reactions.

Germinal centers (GCs), which refers to sites within lymphoid tissue that are more active in lymphocyte proliferation than are other parts of the lymphoid tissue, containing rapidly proliferating cells (ie, centroblasts) are the main site for high-affinity antibody-secreting plasma cell and memory B-cell generatior (Jacob J, Kelsoe G, Rajewsky K, Weiss U., Nature. 1991; 354:389-392). Within GCs, somatic hypermutation (SHM) and purifying selection produce the higher affinity B-cell clones that form the memory compartments of humoral immunity (Jacob J, Kelsoe G, Rajewsky K, Weiss U., Nature. 1991; 354:389-392; Kelsoe G., Immunity. 1996; 4:107-111). Affinity maturation in GCs does not represent an intrinsic requirement for BCR signal strength but rather a local, Darwinian competition. The dynamics of lymphocyte entry into follicles and their selection for migration into and within GCs represents a complex ballet of molecular interactions orchestrated by chemotactic gradients and B-cell receptor (BCR) engagement that is only now being elucidated (Allen C D, Okada T, Cyster J G., Immunity. 2007; 27:190-202).

B-cell subsets with individualized functions such as B-1 and marginal zone (MZ, referring to the junction of the lymphoid tissue of a lymphatic nodule with the surrounding non-lymphoid red pulp of the spleen) B cells have also been identified. Murine B-1 cells are a unique CD5+ B-cell subpopulation (Hayakawa K, Hardy R R, Parks D R, Herzenberg L A., J Exp Med. 1983; 157:202-218) distinguished from conventional B (B-2) cells by their phenotype, anatomic localization, self-renewing capacity, and production of natural antibodies (Hardy R R, Hayakawa K., Annu Rev Immunol. 2001; 19:595-621). Peritoneal B-1 cells are further subdivided into the B-1a (CD5+) and B-1b (CD5−) subsets. Their origins, and whether they derive from the same or distinct progenitors compared with B-2 cells, have been controversial (Dorshkind K, Montecino-Rodriguez E., Nat Rev Immunol. 2007; 7:213-219). However, a B-1 progenitor that appears distinct from a B-lineage progenitor that develops primarily into the B-2 population has been identified in murine fetal marrow, and to a lesser degree in adult marrow (Montecino-Rodriguez E, Leathers H, Dorshkind K., Nat Immunol. 2006; 7:293-301). B-1a cells and their natural antibody products provide innate protection against bacterial infections in naive hosts, while B-1b cells function independently as the primary source of long-term adaptive antibody responses to polysaccharides and other T cell-independent type 2 antigens during infection (Montecino-Rodriguez E, Leathers H, Dorshkind K., Nat Immunol. 2006; 7:293-301). The function and potential subpopulation status of human B-1 cells is less understood (Dorshkind K, Montecino-Rodriguez E., Nat Rev Immunol. 2007; 7:213-219). MZ B cells are a unique population of murine splenic B cells with attributes of naive and memory B cells (Pillai S, Cariappa A, Moran S T., Annu Rev Immunol. 2005; 23:161-196), and constitute a first line of defense against blood-borne encapsulated bacteria. Uncertainty regarding the identity of human MZ B cells partially reflects the fact that the microscopic anatomy of the human splenic MZ differs from rodents (Steiniger B, Timphus E M, Barth P J., Histochem Cell Biol. 2006; 126:641-648) Likewise, the microscopic anatomy of human follicular mantle zones is not recapitulated in mouse spleen and lymph nodes.

The B1, MZ, and GC B-cell subsets all contribute to the circulating natural antibody pool, thymic-independent IgM antibody responses, and adaptive immunity by terminal differentiation into plasma cells, the effector cells of humoral immunity (Radbruch A, Muehlinghaus G, Luger E O, et al., Nat Rev Immunol. 2006; 6:741-750). Antigen activation of mature B cells leads initially to GC development, the transient generation of plasmablasts that secrete antibody while still dividing, and short-lived extrafollicular plasma cells that secrete antigen-specific germ line-encoded antibodies (FIG. 1). GC-derived memory B cells generated during the second week of primary antibody responses express mutated BCRs with enhanced affinities, the product of SHM. Memory B cells persist after antigen challenge, rapidly expand during secondary responses, and can terminally differentiate into antibody-secreting plasma cells. In a manner similar to the early stages of B-cell development in fetal liver and adult marrow, plasma cell development is tightly regulated by a panoply of transcription factors, most notably Bcl-6 and BLIMP-1 (Shapiro-Shelef M, Calame K., Nat Rev Immunol. 2005; 5:230-242).

Persistent antigen-specific antibody titers derive primarily from long-lived plasma cells (Radbruch A, Muehlinghaus G, Luger E O, et al., Nat Rev Immunol. 2006; 6:741-750). Primary and secondary immune responses generate separate pools of long-lived plasma cells in the spleen, which migrate to the marrow where they occupy essential survival niches and can persist for the life of the animal without the need for self-replenishment or turnover ((Radbruch A, Muehlinghaus G, Luger E O, et al., Nat Rev Immunol. 2006; 6:741-750; McHeyzer-Williams L J, McHeyzer-Williams M G., Annu Rev Immunol. 2005; 23:487-513). The marrow plasma cell pool does not require ongoing contributions from the memory B-cell pool for its maintenance, but when depleted, plasma cells are replenished from the pool of memory B cells (Dilillo D J, Hamaguchi Y, Ueda Y, et al., J Immunol. 2008; 180:361-371). Thereby, persisting antigen, cytokines, or Toll-like receptor signals may drive the memory B-cell pool to chronically differentiate into long-lived plasma cells for long-lived antibody production.

In addition to their essential role in humoral immunity, B cells also mediate/regulate many other functions essential for immune homeostasis (FIG. 2). Of major importance, B cells are required for the initiation of T-cell immune responses, as first demonstrated in mice depleted of B cells at birth using anti-IgM antiserum (Ron Y, De Baetselier P, Gordon J, Feldman M, Segal S., Eur J Immunol. 1981; 11:964-968). However, this has not been without controversy as an absence of B cells impairs CD4 T-cell priming in some studies, but not others. Nonetheless, antigen-specific interactions between B and T cells may require the antigen to be first internalized by the BCR, processed, and then presented in an MHC-restricted manner to T cells (Ron Y, Sprent J., J Immunol. 1987; 138:2848-2856; Janeway C A, Ron J, Jr, Katz M E., J Immunol. 1987; 138:1051-1055; Lanzavecchia A., Nature. 1985; 314:537-539).

B-Cell Abnormalities:

The normal B-cell developmental stages have malignant counterparts that reflect the expansion of a dominant subclone leading to development of leukemia and lymphoma. For example, non-T, non-B ALL is a malignancy of B-cell precursors (Korsmeyer S J, Arnold A, Bakhshi A, et al., J Clin Invest. 1983; 71:301-313). The antiapoptotic Bcl-2 gene was discovered as the translocation partner with the IgH locus in the t(14; 18)(q32; q21); frequently occurring in follicular lymphoma (Tsujimoto Y, Finger L R, Yunis J, Nowell P C, Croce C M., Science. 1984; 226:1097-1099). A substantial number of cases of diffuse large B-cell lymphoma exhibit dysregulated expression of the transcriptional repressor Bcl-6 (Ye B H, Lista F, Lo Coco F, et al., Science. 1993; 262:747-750). The Hodgkin/Reed-Sternberg cell in Hodgkin lymphoma, is of B-lymphocyte origin based on the demonstration of clonal Ig gene rearrangements (Kuppers R, Rajewsky K, Zhao M, et al., Proc Natl Acad Sci USA. 1994; 91: 10962-10966).

The monoclonal gammopathies (paraproteinemias or dysproteinemias) are a group of disorders characterized by the proliferation of a single clone of plasma cells which produces an immunologically homogeneous protein commonly referred to as a paraprotein or monoclonal protein (M-protein, where the "M" stands for monoclonal). Each serum M-protein consists of two heavy polypeptide chains of the same class designated by a capital letter and a corresponding Greek letters: Gamma (γ) in IgG, Alpha (α) in IgA, Mu (μ) in IgM, Delta (δ) in IgD, Epsilon (ε) in IgE. For example, basophils in IgE myeloma are characterized by a higher expression of high affinity IgE receptor relative to normal controls.

Multiple Myeloma

Multiple myeloma (MM), a B cell malignancy characterized by the accumulation of plasma cells in the BM and the secretion of large amounts of monoclonal antibodies that ultimately causes bone lesions, hypercalcaemia, renal disease, anemia, and immunodeficiency (Raab M S, Podar K, Breitkreutz I, Richardson P G, Anderson K C., Lancet 2009; 374:324-39), is the second most frequent blood disease in the United States affecting 7.1 per 100,000 men and 4.6 per 100,000 women.

MM is characterized by monoclonal proliferation of malignant plasma cells (PCs) in the bone marrow (BM), the presence of high levels of monoclonal serum antibody, the development of osteolytic bone lesions, and the induction of angiogenesis, neutropenia, amyloidosis, and hypercalcemia (Vanderkerken K, Asosingh K, Croucher P, Van Camp B., Immunol Rev 2003; 194:196-206; Raab M S, Podar K, Breitkreutz I, Richardson P G, Anderson K C., Lancet 2009; 374:324-39). MM is seen as a multistep transformation process. G. Pratt., Molecular Aspects of multiple myeloma, J. Clin. Pathol: Molec. Pathol. 55: 273-83 (2002). Although little is known about the immortalizing and initial transforming events, the initial event is thought to be the immortalization of a plasma cell to form a clone, which may be quiescent, non-accumulating and not cause end organ damage due to accumulation of plasma cells within the bone marrow (MGUS). Smouldering MM (SMM) also has no detectable end-organ damage, but differs from MGUS by having a serum mIg level higher than 3 g/dl or a BM PC content of more than 10% and an average rate of progression to symptomatic MM of 10% per year. Currently there are no tests that measure phenotypic or genotypic markers on tumor cells that predict progression. W. Michael Kuehl and P. Leif Bergsagel, Molecular pathogenesis of multiple myeloma and its premalignant precursor, J. Clin. Invest. 122 (10): 3456-63 (2012). An abnormal immunophenotype distinguishes healthy plasma cells (PCs) from tumor cells. Healthy BM PCs are CD38+CD138+CD19+CD45+CD56−. Id. Although MM tumor cells also are CD38+CD138+, 90% are CD19−, 99% are CD45− or CD45 lo, and 70% are CD56+. Id.

The prognosis and treatment of this disease has greatly evolved over the past decade due to the incorporation of new agents that act as immunomodulators and proteosome inhibitors. Despite recent progress with a number of novel treatments (Raab M S, Podar K, Breitkreutz I, Richardson P G, Anderson K C., Lancet 2009; 374:324-39; Schwartz R N, Vozniak M., J Manag Care Pharm 2008; 14:12-9), patients only experience somewhat longer periods of remission. Because of the development of drug resistance or relapse, MM is an incurable disease (Schwartz R N, Vozniak M., J Manag Care Pharm 2008; 14:12-9; Kyle R A., Blood 2008; 111:4417-8), with a median survival time of 3-4 years.

Disease management is currently tailored based on the patient's co-morbidity factors and stage of disease (for a complete list of treatments and their implementation, see Raab M S, Podar K, Breitkreutz I, Richardson P G, Anderson K C., Lancet 2009; 374:324-39 and Schwartz R N, Vozniak M., J Manag Care Pharm 2008; 14:12-9).

Staging of Myeloma

While multiple myeloma may be staged using the Durie-Salmon system, its value is becoming limited because of newer diagnostic methods. The International Staging System for Multiple Myeloma relies mainly on levels of albumin and beta-2-microglobulin in the blood. Other factors that may be important are kidney function, platelet count and the patient's age. [www.cancer.org/cancer/multiplemyeloma/detailedguide/multiple-myeloma-staging, last revised Feb. 12, 2013]

The Durie-Salmon staging system is based on 4 factors:

The amount of abnormal monoclonal immunoglobulin in the blood or urine: Large amounts of monoclonal immunoglobulin indicate that many malignant plasma cells are present and are producing that abnormal protein.

The amount of calcium in the blood: High blood calcium levels can be related to advanced bone damage. Because bone normally contains lots of calcium, bone destruction releases calcium into the blood.

The severity of bone damage based on x-rays: Multiple areas of bone damage seen on x-rays indicate an advanced stage of multiple myeloma.

The amount of hemoglobin in the blood: Hemoglobin carries oxygen in red blood cells. Low hemoglobin levels mean that the patient is anemic; it can indicate that the myeloma cells occupy much of the bone marrow and that not enough space is left for the normal marrow cells to make enough red blood cells.

This system uses these factors to divide myeloma into 3 stages. Stage I indicates the smallest amount of tumor, and stage III indicates the largest amount of tumor:

In Stage I, a relatively small number of myeloma cells are found. All of the following features must be present:

Hemoglobin level is only slightly below normal (still above 10 g/dL)

Bone x-rays appear normal or show only 1 area of bone damage

Calcium levels in the blood are normal (less than 12 mg/dL)

Only a relatively small amount of monoclonal immunoglobulin is in blood or urine In Stage II, a moderate number of myeloma cells are present. Features are between stage I and stage III.

In Stage III, a large number of myeloma cells are found. One or more of the following features must be present:

Low hemoglobin level (below 8.5 g/dL)

High blood calcium level (above 12 mg/dL)

3 or more areas of bone destroyed by the cancer

Large amount of monoclonal immunoglobulin in blood or urine

The International Staging System divides myeloma into 3 stages based only on the serum beta-2 microglobulin and serum albumin levels.

In Stage I, serum beta-2 microglobulin is less than 3.5 (mg/L) and the albumin level is above 3.5 (g/L). Stage II is neither stage I nor III, meaning that either: The beta-2 microglobulin level is between 3.5 and 5.5 (with any albumin level), OR the albumin is below 3.5 while the beta-2 microglobulin is less than 3.5. In Stage III, Serum beta-2 microglobulin is greater than 5.5.

Factors other than stage that affect survival include kidney function (when the kidneys are damaged by the monoclonal immunoglobulin, blood creatinine levels rise, predicting a worse outlook); age (in the studies of the international staging system, older people with myeloma do not live as long); the myeloma labeling index (sometimes called the plasma cell labeling index), which, indicates how fast the cancer cells are growing; a high labeling index can predict a more rapid accumulation of cancer cells and a worse outlook; and chromosome studies, i.e., certain chromosome changes in the malignant cells can indicate a poorer outlook. For example, changes in chromosome 13 will lower a person's chances for survival. Another genetic abnormality that predicts a poor outcome is a translocation (meaning an exchange of material) from chromosomes 4 and 14.

Biological pharmacotherapy for the treatment of MM currently includes immunomodulatory agents, such as thalidomide or its analogue, lenalidomide, and bortezomib, a first-in-class proteosome inhibitor. Unfortunately, some side effects associated with these therapies such as peripheral neuropathy and thrombocytopenia (in the case of bortezomib) restrict dosing and duration of treatment (Raab M S, Podar K, Breitkreutz I, Richardson P G, Anderson K C., Lancet 2009; 374:324-39; Schwartz R N, Vozniak M., J Manag Care Pharm 2008; 14:12-9; Field-Smith A, Morgan G J, Davies F E., Ther Clin Risk Manag 2006; 2:271-9).

Despite significant advances in the implementation of these drugs, MM still remains a lethal disease for the vast majority of patients. Since MM is a disease characterized by multiple relapses, the order/sequencing of the different effective treatment options is crucial to the outcome of MM patients. In the frontline setting, the first remission is likely to be the period during which patients will enjoy the best quality of life. Thus, one goal is to achieve a first remission that is the longest possible by using the most effective treatment upfront. At relapse, the challenge is to select the optimal treatment for each patient while balancing efficacy and toxicity. The decision will depend on both disease- and patient-related factors (Mohty B, El-Cheikh J, Yakoub-Agha I, Avet-Loiseau H, Moreau P, Mohty M., Leukemia 2012; 26:73-85). Thus, having the capability of testing the efficacy of a potential therapy, prior to patient treatment, can have a major impact in the management of this disease.

As opposed to other hematological malignancies, MM as well as other cancers that metastasize to the BM strongly interact with the BM microenvironment, which is composed of endothelial cells, stromal cells, osteoclasts (OCL), osteoblasts (OSB), immune cells, fat cells and the extracellular matrix (ECM). These interactions, as illustrated in FIG. 1 (adapted from Roodman G D., Bone 2011; 48:135-40), are responsible for the specific homing in the BM, the proliferation and survival of the MM cells, the resistance of MM cells to drug treatment, and the development of osteolysis, immunodeficiency, and anemia (Dvorak H F, Weaver V M, Tlsty T D, Bergers G., J Surg Oncol 2011; 103:468-74; De Raeve H R, Vanderkerken K., Histol Histopathol 2005; 20:1227-50; Fowler J A, Edwards C M, Croucher P I., Bone 2011; 48:121-8; Fowler J A, Mundy G R, Lwin S T, Edwards C M., Cancer Res 2012; Roodman G D., J Bone Miner Res 2002; 17:1921-5).

The Bone Marrow Niche and MM Progression

The BM niche plays a key role in MM-related bone disease. A complex interaction with the BM microenvironment in areas adjacent to tumor foci, characterized by activation of osteoclasts and suppression of osteoblasts, leads to lytic bone disease. W. Michael Kuehl and P. Leif Bergsagel, Molecular pathogenesis of multiple myeloma and its premalignant precursor, J. Clin. Invest. 122 (10): 3456-63 (2012); Shmuel Yaccoby, Advances in the understanding of myeloma bone disease and tumour growth, Br. J. Haematol. 149 (3): 311-321 (2010). Thus, although the MM microenvironment is highly complex, it is understood that suppression of OSB activity plays a key role in the bone destructive process as well as progression of the tumor burden (Roodman G D., Bone 2011; 48:135-40). Treatments that target both the bone microenvironment as well as the tumor, such as bortezomib and immunomodulatory drugs, have been more effective than prior therapies for MM and have dramatically increased both progression-free survival and overall survival of patients.

MM cells closely interact with the BM microenvironment, also termed the cancer niche. The elements of the bone marrow niche can provide an optimal growth environment for multiple hematological malignancies including multiple myeloma (MM). MM cells convert the bone marrow into specialized neoplastic niche, which aids the growth and spreading of tumor cells by a complex interplay of cytokines, chemokines, proteolytic enzymes and adhesion molecules. Moreover, the MM BM microenvironment confers survival and chemoresistance of MM cells to current therapies.

Bone Marrow Stromal Cells (BMSCs)

Multiple myeloma (MM) cells adhere to BMSC and ECM. Tumor cells, such as MM cells, bind to ECM proteins, such as type I collagen and fibronectin via syndecan 1 and very late antigen 4 (VLA-4) on MM cells and to BMSC VCAM-1 via VLA-4 on MM cells. Adhesion of MM cells to BMSC activates many pathways resulting in upregulation of cell cycle regulating proteins and antiapoptotic proteins (Hideshima T, Bergsagel P L, Kuehl W M, Anderson K C., Blood. 2004; 104(3):607-618). The interaction between MM cells and BMSCs triggers NF-κB signaling pathway and interleukin-6 (IL-6) secretion in BMSCs. In turn, IL-6 enhances the production and secretion of VEGF by MM cells. The existence of this paracrine loop optimizes the BM milieu for MM tumor cell growth (Kumar S, Witzig T E, Timm M, et al., Leukemia. 2003; 17(10):2025-2031). BMSC-MM cell interaction is also mediated through Notch. The Notch-signaling pathways both in MM cells as well as in BMSC, promote the induction of IL-6, vascular endothelial growth factor (VEGF), and insulin-like growth factor (IGF-1) secretion and is associated with MM cell proliferation and survival (Radtke F, Raj K., Nature Reviews Cancer. 2003; 3(10):756-767; Nefedova Y, Cheng P, Alsina M, Dalton W S, Gabrilovich D I., Blood. 2004; 103(9):3503-3510). It has been shown that BMSC from MM patients expresses several proangiogenic molecules, such as VEGF, basic-fibroblast growth factor (bFGF), angiopoietin 1 (Ang-1), transforming growth factor (TGF)-β, platelet-derived growth factor (PDGF), hepatocyte growth factor (HGF) and interleukin-1 (IL-1) (Giuliani N, Storti P, Bolzoni M, Palma B D, Bonomini S., Cancer Microenvironment. 2011; 4(3): 325-337). BMSCs from MM patients also have been shown to release exosomes, which are transferred to MM cells, thereby resulting in modulation of tumor growth in vivo, mediated by specific miRNA (Roccaro A M, Sacco A, Azab A K, et al., Blood. 2011; 118, abstract 625 ASH Annual Meeting Abstracts).

Endothelial Cells and Angiogenesis

BM angiogenesis represents a constant hallmark of MM progression, partly driven by release of pro-angiogenic cytokines from the tumor plasma cells, BMSC, and osteoclasts, such as VEGF, bFGF, and metalloproteinases (MMPs). The adhesion between MM cells and BMSCs upregulates many cytokines with angiogenic activity, most notably VEGF and bFGF (Podar K, Anderson K C., Blood. 2005; 105(4):1383-1395). In MM cells, these pro-angiogenic factors may also be produced constitutively as a result of oncogene activation and/or genetic mutations (Rajkumar S V, Witzig T E., Cancer Treatment Reviews. 2000; 26(5): 351-362). Evidence for the importance of angiogenesis in the pathogenesis of MM was obtained from BM samples from MM patients (Kumar S, Gertz M A, Dispenzieri A, et al., Bone Marrow Transplantation. 2004; 34(3):235-239). The level of BM angiogenesis, as assessed by grading and/or microvessel density (MVD), is increased in patients with active MM as compared to those with inactive disease or monoclonal gammopathy of undetermined significance (MGUS), a less advanced plasma cell disorder. Comparative gene expression profiling of multiple myeloma endothelial cells and MGUS endothelial cells has been performed in order to determine a genetic signature and to identify vascular mechanisms governing the malignant progression (Ria R, Todoerti K, Berardi S, et al., Clinical Cancer Research. 2009; 15(17):5369-5378). Twenty-two genes were found differentially expressed at relatively high stringency in MM endothelial cells compared with MGUS endothelial cells. Functional annotation revealed a role of these genes in the regulation of ECM formation and bone remodelling, cell adhesion, chemotaxis, angiogenesis, resistance to apoptosis, and cell-cycle regulation. The distinct endothelial cell gene expression profiles and vascular phenotypes detected may influence remodelling of the bone marrow microenvironment in patients with active multiple myeloma. Overall, these evidences suggest that EC presents with functional, genetic, and morphologic features indicating their ability to induce BM neovascularization, resulting in MM cell growth, and disease progression.

Osteoclasts

The usual balance between bone resorption and new bone formation is lost in many cases of MM, resulting in bone destruction and the development of osteolytic lesions (Bataille R, Chappard D, Marcelli C, et al., *Journal of Clinical Oncology*. 1989; 7(12):1909-1914). Bone destruction develops adjacent to MM cells, yet not in areas of normal bone marrow. There are several factors implicated in osteoclast activation, including receptor activator of NF-κB ligand (RANKL), macrophage inflammatory protein-1a (MIP-1a), interleukin-3 (IL-3), and IL-6 (Roodman G D., *Leukemia*. 2009; 23(3):435-441). RANK ligand is a member of the tumor necrosis factor (TNF) family and plays a major role in the increased osteoclastogenesis implicated in MM bone disease. RANK is a transmembrane signaling receptor expressed by osteoclast cells. MM cell binding to neighboring BMSC within the bone marrow results in increased RANKL expression. This leads to an increase in osteoclast activity through the binding of RANKL to its receptor, on osteoclast precursor cells, which further promotes their differentiation through NF-κB and JunN-terminal kinase pathway (Ehrlich L A, Roodman G D., *Immunological Reviews*. 2005; 208:252-266). RANKL is also involved in inhibition of osteoclast apoptosis. Blocking RANKL with a soluble form of RANK has been shown to modulate not only bone loss but also tumor burden in MM in vivo models (Yaccoby S, Pearse R N, Johnson C L, Barlogie B, Choi Y, Epstein J., *British Journal of Haematology*. 2002; 116(2): 278-290). Moreover osteoclasts constitutively secrete proangiogenic factors osteopontin that enhanced vascular tubule formation (Tanaka Y, Abe M, Hiasa M, et al., *Clinical Cancer Research*. 2007; 13(3):816-823).

Osteoblasts in MM Progression

Osteoblasts are thought to contribute to MM pathogenesis by supporting MM cells growth and survival (Karadag A, Oyajobi B O, Apperley J F, Graham R, Russell G, Croucher P I., *British Journal of Haematology*. 2000; 108(2):383-390). This could potentially result from the ability of osteoblasts to secrete IL-6 in a co-culture system with MM cells, thus increasing IL-6 levels within the BM milieu and inducing MM plasma cell growth. Other mechanisms include the possible role of osteoblasts in stimulating MM cell survival by blocking TRAIL-mediated programmed MM cell death, by secreting osteoprotegerin (OPG), a receptor for both RANKL and TRAIL (Shipman C M, Croucher P I., *Cancer Research*. 2003; 63(5):912-916). In addition, suppression of osteoblast activity is responsible for both bone destructive process and progression of myeloma tumor burden. Several factors have been implicated in the suppression of osteoblast activity in MM, including DKK1 (Tian E, Zhan F, Walker R, et al., *The New England Journal of Medicine*. 2003; 349(26):2483-2494). DKK1 is a Wnt-signaling antagonist secreted by MM cells that inhibits osteoblast differentiation. DKK1 is significantly overexpressed in patients with MM who present with lytic bone lesions. Myeloma-derived DKK1 also disrupts Wnt-regulated OPG and RANKL production by osteoblasts. Studies have shown that blocking DKK1 and activating Wnt signaling prevents bone disease in MM and is associated with a reduction in tumor burden (Yaccoby S, Ling W, Zhan F, Walker R, Barlogie B, Shaughnessy J D., Jr., *Blood*. 2007; 109(5):2106-2111; Edwards C M, Edwards J R, Lwin S T, et al., *Blood*. 2008; 111(5):2833-2842; Fulciniti M, Tassone P, Hideshima T, et al., *Blood*. 2009; 114(2):371-379).

Many components of the microenvironment support the propagation of the MM cells through cell-cell adhesion and the release of growth factors such as interleukin-6 (IL-6) and insulin-like growth factor-1 (IGF-1) (Deleu S, Lemaire M, Arts J, et al., Leukemia 2009; 23:1894-903; Field-Smith A, Morgan G J, Davies F E., Ther Clin Risk Manag 2006; 2:271-9; D'Souza S, del Prete D, Jin S, et al. Blood 2011; 118:6871-80). Survival and drug resistance of malignant cells is associated with their ability to shape the local microenvironment, in part by disrupting the balance of pro- and anti-angiogenic factors through neovascularization (Otjacques E, Binsfeld M, Noel A, Beguin Y, Cataldo D, Caers J., Int J Hematol 2011; 94:505-18) and bone remodeling which leads to osteolysis (Raje N, Roodman G D., Clin Cancer Res 2011; 17:1278-86; Giuliani N, Rizzoli V, Roodman G D., Blood 2006; 108:3992-6; Lentzsch S, Ehrlich L A, Roodman G D., Hematol Oncol Clin North Am 2007; 21:1035-49, viii).

Unfortunately, primary MM tumor cells have been difficult to propagate ex vivo because they require a microenvironment hard to reproduce in vitro. MM cells grown in vitro therefore are very short lived and grow poorly outside their BM milieu and attempts to optimize their maintenance have been hampered by lack of known conditions that allow for their ex vivo survival (Zlei M, Egert S, Wider D, Ihorst G, Wasch R, Engelhardt M., Exp Hematol 2007; 35:1550-61). Aside from various xenograft models (Calimeri T, Battista E, Conforti F, et al., Leukemia 2011; 25:707-11; Yata K, Yaccoby S., Leukemia 2004; 18:1891-7; Yaccoby S, Johnson C L, Mahaffey S C, Wezeman M J, Barlogie B, Epstein J., Blood 2002; 100:4162-8; Bell E., Nature Reviews Immunology 2006; 6:87), only one group to date has reported on creating an in vitro model capable of supporting the proliferation and survival of MM cells (Kirshner J, Thulien K J, Martin L D, et al., Blood 2008; 112:2935-45). However, the macroscale static methodology that was employed has limited value as, inter alia, it fails to recapitulate the spatial and temporal characteristics of the complex tumor niche.

Recently, Lee et al described a three-dimensional (3D) tissue construct in which a multichannel microfluidic device was used to create mineralized 3D tissue-like structures by dynamic long-term culture of osteoblasts to evaluate efficacy of biomaterials aimed at accelerating orthopedic implant related wound healing while preventing bacterial infection. Development of osteoblasts into 3D tissue-like structures and how this development was influenced by interaction with the pathogen *Staphylococcus epidermidis* was studied in real-time. Lee, et al., Microfluidic approach to create three-dimensional tissue models for biofilm-related infection of orthopoedic implants, Tissue Engineering: Part C, 17 (1): 39-48 (2011); Lee, et al., Microfluidic 3D bone tissue model for high throughput evaluation of wound healing and infection-preventing biomaterials," Biomaterials 33: 999-1006 (2012). It was observed that in the absence of bacteria, osteoblasts formed a confluent layer on the bottom channel surface, gradually migrated to the side and top surfaces, and formed calcified 3D nodular structures in 8 days.

This 3D biological construct now has been used to create a microfluidic 3D MM/bone tissue model, which provides a perfused microenvironment, facilitates the seeding of adherent and non-adherent BM cells, and accelerates reconstruction of the BM milieu. The model system better preserves the BM/MM interactions, and, from a clinical perspective, enables a physiologically relevant system that: 1) maximizes sample use by requiring very small amounts of patient BM cells (<1×106 cells) and plasma (<2 mL/culture/week) and 2) accelerates the evaluation of new therapeutics for the treatment of MM. Furthermore, because real-time monitoring of BM/MM cell developments and interactions are performed, the described model is useful to study and identify new mechanisms associated with the MM niche and tumor progression. For example, use of the microfluidic 3D MM/bone tissue model to evaluate effects of soluble factors secreted by MM cells on the maintenance of the microfluidic 3D bone tissue has been reported. Zhang, et al., Microfluidic 3D bone tissue model for multiple myeloma, 9th World Biomaterials Congress, Jun. 5, 2012.

In addition, although MM has been used as a model system, the conservation of the BM microenvironment from BM biospecimens has broader utility in the study of other blood cancers and solid tumors that reside or metastasize to the BM.

SUMMARY OF THE INVENTION

According to one aspect, the described invention provides an ex vivo dynamic multiple myeloma (MM) cancer niche contained in a microfluidic device comprising (a) a three-dimensional tissue construct containing a dynamic ex vivo bone marrow (BM) niche comprising (i) a mineralized bone-like tissue comprising (a) viable osteoblasts self-organized into cohesive multiple cell layers and (b) an extracellular matrix secreted by the viable adherent osteoblasts; and (ii) a microenvironment dynamically perfused by nutrients and dissolved gas molecules; and (b) human myeloma cells seeded from a biospecimen composition comprising mononuclear cells and the multiple myeloma cells, wherein the human myeloma cells are in contact with osteoblasts of the BM niche, and the viability of the human myeloma cells is maintained by the MM cancer niche.

According to another aspect, the described invention provides a method for preparing an ex vivo dynamic multiple myeloma (MM) cancer niche comprising (a) acquiring a biospecimen containing mononuclear cells from a subject in need thereof, wherein the biospecimen comprises viable multiple myeloma cells; (b) preparing a biospecimen composition comprising the viable multiple myeloma cells and plasma autologous to the subject; (c) preparing a three-dimensional tissue construct containing a dynamic ex vivo bone marrow (BM) niche comprising (i) a mineralized bone-like tissue comprising (a) viable osteoblasts self-organized into cohesive multiple cell layers and (b) an extracellular matrix secreted by the viable adherent osteoblasts; and (ii) a microenvironment dynamically perfused by nutrients and dissolved gas molecules; (d) adding the biospecimen composition to the three-dimensional tissue construct containing the dynamic ex vivo bone marrow (BM) niche to seed the BM niche with MM cells; and (e) forming the dynamic ex vivo MM niche such that the MM cells are in contact with the osteoblasts of the BM niche, wherein the MM cancer niche is capable of maintaining viability of the human myeloma cells.

According to another aspect, the described invention provides a method for assessing chemotherapeutic efficacy of a chemotherapeutic agent on viable human multiple myeloma cells obtained from a subject comprising: (a) acquiring a biospecimen from the subject, wherein the biospecimen comprises viable multiple myeloma cells; (b) preparing a biospecimen composition comprising the viable multiple myeloma cells and plasma autologous to the subject; (c) preparing a three-dimensional tissue construct containing a dynamic ex vivo bone marrow (BM) niche comprising (i) a mineralized bone-like tissue comprising (a) viable osteoblasts self-organized into cohesive multiple cell layers and (b) an extracellular matrix secreted by the viable adherent osteoblasts; and (ii) a microenvironment dynamically perfused by nutrients and dissolved gas molecules; (d) adding the biospecimen composition to the three-dimensional tissue construct containing the dynamic ex vivo bone marrow (BM) niche to seed the BM niche with MM cells; (e) forming the dynamic ex vivo MM niche such that the MM cells are in contact with the osteoblasts of the BM niche, wherein the MM cancer niche is capable of maintaining viability of the human myeloma cells; (f) optionally cultivating the human myeloma cells in the MM cancer niche to propagate the MM cells for a period of time; (g) adding a test chemotherapeutic agent to the MM niche; (h) comparing at least one of viability and level of apoptosis of the MM cells in the MM niche in the presence of the chemotherapeutic agent to an untreated control; and (i) initiating therapy to treat the MM in the patient if the agent significantly reduces viability or increases apoptosis of the MM cells.

According to one embodiment, the biospecimen comprising mononuclear cells and the human myeloma cells further comprises human plasma autologous to the patient from which the human myeloma cells were derived.

According to one embodiment, the microenvironment dynamically perfused by nutrients and dissolved gas molecules of the dynamic ex vivo bone marrow (BM) niche is suitable for dynamic propagation of the human myeloma cells.

According to one embodiment, the MM niche further comprises osteoblast-secreted and MM cell-secreted soluble cytokines and growth factors.

According to one embodiment, the MM cells are adherent to osteoblasts of the BM niche. According to another embodiment, the MM cells adhere to the osteoblasts of the BM niche by cell-cell interaction.

According to one embodiment, the human myeloma cells are cellular components of a bone marrow aspirate. According to another embodiment, the human myeloma cells are cellular components of peripheral blood. According to another embodiment, the human myeloma cells are cellular components of a core biopsy.

According to one embodiment, the ex vivo dynamic multiple myeloma (MM) cancer niche is suitable for dynamic propagation of the human myeloma cells for at least 7 days.

According to one embodiment, the sample of human myeloma cells added to the BM niche constitutes $1 \times 10^4$ to $1 \times 10^5$ mononuclear cells.

According to one embodiment, propagation of the MM cells is capable of producing deterioration of the 3D ossified tissue of the BM niche.

According to one embodiment, the chemotherapeutic agent is selected from the group consisting of an alkylating agent, an antimetabolite, a natural product, a hormone, a biologic, a kinase inhibitor, a platinum coordination complex, an EDTA derivative, a platelet-reducing agent, a retinoid and a histone deacetylase inhibitor.

According to one embodiment, the chemotherapeutic agent is selected from the group consisting of an immunomodulatory drug, a proteasome inhibitor and a bisphosphonate. According to another embodiment, the immunomodulatory drug is Thalidomide or Lenalidomide. According to another embodiment, the proteasome inhibitor is Bortezomib. According to another embodiment, the bisphosphonate is Pamidronate or zoledronic acid.

BRIEF DESCRIPTION OF THE FIGURES

FIG. 3*a-d* and left panel e show real-time imaging of osteoblast development sequence. Right panel e shows end-point imaging after alizarin red staining. The arrow depicted in e (right panel) indicates nodular structure with dense ECM. Bars represent 200 µm.

FIG. 6*a-c* show fluorescence images of CFSE labeled BM cells at day 0, day 7 and day 21 respectively. Cells get darker as they lose half of the CFSE staining after each cell division.

FIG. 7*a-c* show a schematic of bone marrow cell activity upon seeding into the 3D-bone like tissue at 0, day 7 and day 21 respectively.

FIG. 10*a* shows CD38+CD56+CFSE+MM cells. FIG. 10*b* shows CD138+CFSE+MM cells.

DETAILED DESCRIPTION OF THE INVENTION

Glossary

Figure 1:
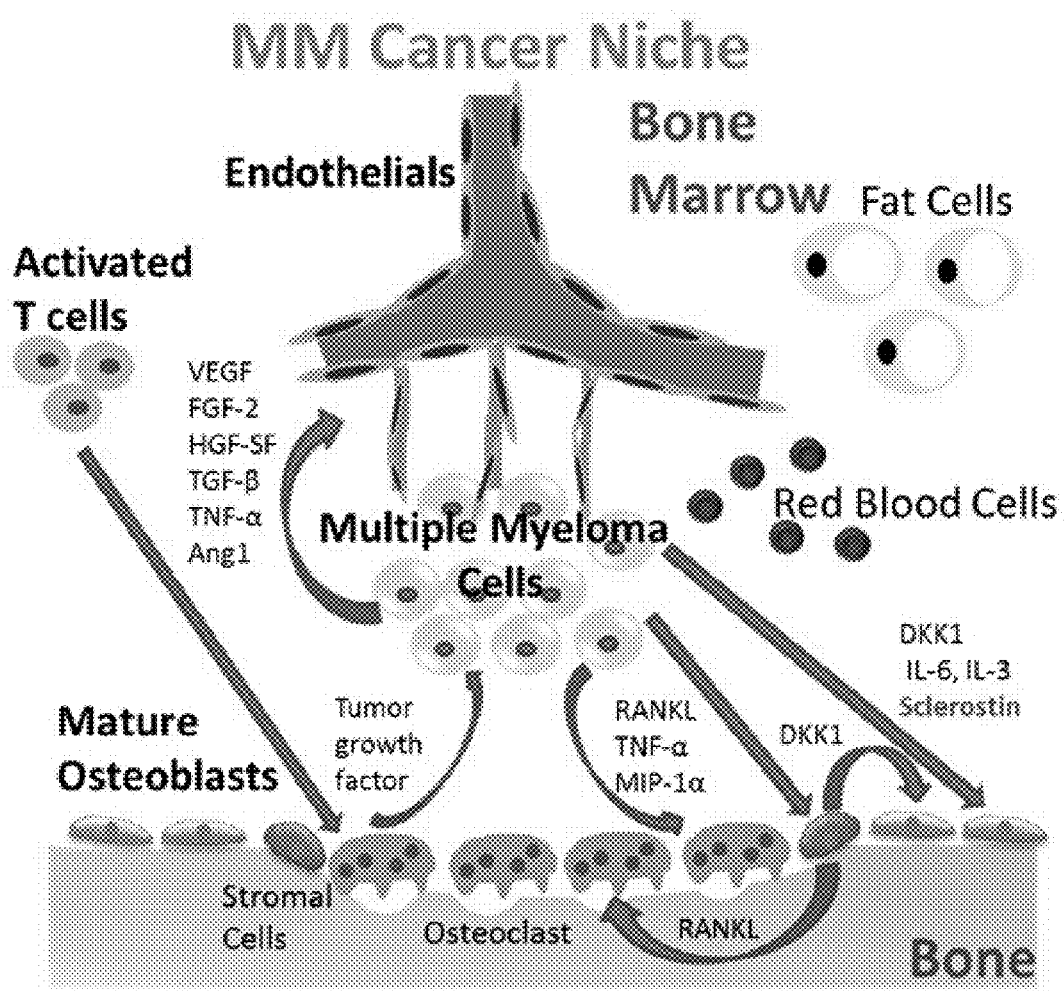
FIG. 1 shows a schematic representation of the MM cancer niche.

The terms "administering" or "administration" as used herein are used interchangeably to mean the giving or applying of a substance The term "administering" as used herein includes in vivo administration, as well as administration ex vivo.

The term "antigen" and its various grammatical forms refers to any substance that can stimulate the production of antibodies and can combine specifically with them. The term "antigenic determinant" or "epitope" as used herein refers to an antigenic site on a molecule.

An "antiserum" is the liquid phase of blood recovered after clotting has taken place obtained from an immunized mammal, including humans.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon aggregation and mitochondrial localization, induces cytochrome c release. Akt is a critical regulator of GSK-3, and phosphorylation and inactivation of GSK-3 may mediate some of the antiapoptotic effects of Akt.

The term "associate" and its various grammatical forms as used herein refers to joining, connecting, or combining to, either directly, indirectly, actively, inactively, inertly, non-inertly, completely or incompletely. The term "in association with" refers to a relationship between two substances that connects, joins or links one substance with another The term "arrange" as used herein refers to being disposed or placed in a particular kind of order.

The term "Bence Jones protein(s)" as used herein refers to Ig light chain of one type (either κ or λ) that appears in the urine of patients with multiple myeloma.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The term "bone" as used herein refers to a hard connective tissue consisting of cells embedded in a matrix of mineralized ground substance and collagen fibers. The fibers are impregnated with a form of calcium phosphate similar to hydroxyapatite as well as with substantial quantities of carbonate, citrate sodium and magnesium. Bone consists of a dense outer layer of compact substance or cortical substance covered by the periosteum and an inner loose, spongy substance; the central portion of a long bone is filled with marrow. The term "bound" or any of its grammatical forms as used herein refers to the capacity to hold onto, attract, interact with or combine with.

The term "bone morphogenic protein (BMP)" as used herein refers to a group of cytokines that are part of the transforming growth factor-β (TGF-β) superfamily. BMP ligands bind to a complex of the BMP receptor type II and a BMP receptor type I (Ia or Ib). This leads to the phosphorylation of the type I receptor that subsequently phosphorylates the BMP-specific Smads (Smad1, Smad5, and Smad8), allowing these receptor-associated Smads to form a complex with Smad4 and move into the nucleus where the Smad complex binds a DNA binding protein and acts as a transcriptional enhancer. BMPs have a significant role in bone and cartilage formation in vivo. It has been reported that most BMPs are able to stimulate osteogenesis in mature osteoblasts, while BMP-2, 6, and 9 may play an important role in inducing osteoblast differentiation of mesenchymal stem cells. Cheng, H. et al., J. Bone & Joint Surgery 85: 1544-52 (2003).

The term "cell" is used herein to refer to the structural and functional unit of living organisms and is the smallest unit of an organism classified as living.

The term "cell adhesion" refers to adherence of cells to surfaces or other cells, or to the close adherence (bonding) to adjoining cell surfaces.

The term "cell adhesion molecule" refers to surface ligands, usually glycoproteins, that mediate cell-to-cell adhesion. Their functions include the assembly and interconnection of various vertebrate systems, as well as maintenance of tissue integration, wound healing, morphogenic movements, cellular migrations, and metastasis.

The term "cell-cell interaction" refers to the ways in which living cells communicate, whether by direct contact or by means of chemical signals.

The term "cell culture" as used herein refers to establishment and maintenance of cultures derived from dispersed cells taken from original tissues, primary culture, or from a cell line or cell strain.

The term "cell line" as used herein refers to an immortalized cell, which have undergone transformation and can be passed indefinitely in culture.

The term "cell strain" as used herein refers to cells which can be passed repeatedly but only for a limited number of passages.

The term "cell clones" as used herein refers to individual cells separated from the population and allowed to grow.

The term "primary culture" as used herein refers to cells resulting from the seeding of dissociated tissues, i.e. HUVEC cells. Primary cultures often lose their phenotype and genotypes within several passages.

The term "cell passage" as used herein refers to the splitting (dilution) and subsequent redistribution of a monolayer or cell suspension into culture vessels containing fresh media.

The term "chemokine" as used herein refers to a class of chemotactic cytokines that signal leukocytes to move in a specific direction. The terms "chemotaxis" or "chemotactic" refer to the directed motion of a motile cell or part along a chemical concentration gradient towards environmental conditions it deems attractive and/or away from surroundings it finds repellent.

Cluster of Differentiation

The cluster of differentiation (CD) system is a protocol used for the identification of cell surface molecules present on white blood cells. CD molecules can act in numerous ways, often acting as receptors or ligands; by which a signal cascade is initiated, altering the behavior of the cell. Some CD proteins do not play a role in cell signaling, but have other functions, such as cell adhesion. Generally, a proposed surface molecule is assigned a CD number once two specific monoclonal antibodies (mAb) are shown to bind to the molecule. If the molecule has not been well-characterized, or has only one mAb, the molecule usually is given the provisional indicator "w."

The CD system nomenclature commonly used to identify cell markers thus allows cells to be defined based on what molecules are present on their surface. These markers often are used to associate cells with certain immune functions. While using one CD molecule to define populations is uncommon, combining markers has allowed for cell types with very specific definitions within the immune system. There are more than 350 CD molecules identified for humans.

CD molecules are utilized in cell sorting using various methods, including flow cytometry. Cell populations usually are defined using a "+" or a "−" symbol to indicate whether a certain cell fraction expresses or lacks a CD molecule. For example, a "CD34+, CD31−" cell is one that expresses CD34, but not CD31. Table 2 shows commonly used markers employed by skilled artisans to identify and characterize differentiated white blood cell types.

TABLE 2

| Type of Cell | CD Markers |
| --- | --- |
| Stem cells | CD34+, CD31− |
| All leukocyte groups | CD45+ |
| Granulocyte | CD45+, CD15+ |
| Monocyte | CD45+, CD14+ |
| T lymphocyte | CD45+, CD3+ |
| T helper cell | CD45+, CD3+, CD4+ |
| Cytotoxic T cell | CD45+, CD3+, CD8+ |

TABLE 2-continued

| Type of Cell | CD Markers |
| --- | --- |
| B lymphocyte | CD45+, CD19+ or CD45+, CD20+ |
| Thrombocyte | CD45+, CD61+ |
| Natural killer cell | CD16+, CD56+, CD3 |

CD molecules used in defining leukocytes are not exclusively markers on the cell surface. Most CD molecules have an important function, although only a small portion of known CD molecules have been characterized. For example, there are over 350 CD for humans identified thus far.

CD3 (TCR complex) is a protein complex composed of four distinct chains. In mammals, the complex contains a CD3γ chain, a CD3δ chain, and two CD3ε chains, which associate with the T cell receptor (TCR) and the ξ-chain to generate an activation signal in T lymphocytes. Together, the TCR, the ξ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (SSEA-1)) is a carbohydrate adhesion molecule that can be expressed on glycoproteins, glycolipids and proteoglycans. CD15 commonly is found on neutrophils and mediates phagocytosis and chemotaxis.

CD16 is an Fc receptor (FcγRIIIa and FcγRIIIb) found on the surface of natural killer cells, neutrophil polymorphonuclear leukocytes, monocytes and macrophages. Fc receptors bind to the Fc portion of IgG antibodies.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases.

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils. CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigent receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells.

CD56 (neural cell adhesion molecule, NCAM) is a homophilic binding glycoprotein expressed on the surface of neurons, glia, skeletal muscle and natural killer cells. It generally is believed that NCAM has a role in cell-cell adhesion, neurite outgrowth, and synaptic plasticity. There are three known main isoforms of NCAM, each varying only in their cytoplasmic domains: NCAM-120kDA (glycosyl-phopharidylinositol (GPI) anchored); NCAM-140 kDa (short cytoplasmic domain); and NCAM (long cytoplasmic domain). The different domains of NCAM have different roles, with the Ig domains being involved in homophilic binding to NCAM, and the fibronection type III (FNIII) domains being involved in signaling leading to neurite outgrowth.

CD66b ((CGM1); CD67, CGM6, NCA-95) is a glycosyl-phosphatidylinositol (GPI)-linked protein that is a member of the immunoglobulin superfamily and carcinoembryonic antigen (CEA)-like subfamily. CD66b, expressed on granulocytes, generally is believed to be involved in regulating adhesion and activation of human eosinophils.

Human leukocyte antigen (HLA)-DR is a major histocompatibility complex (MHC) class II cell surface receptor. HLA-DR commonly is found on antigen-presenting cells such as macrophages, B-cells, and dendritic cells. This cell surface molecule is a $\alpha\beta$ heterodimer with each subunit containing 2 extracellular domains: a membrane spanning domain and a cytoplasmic tail. Both the $\alpha$ and $\beta$ chains are anchored in the membrane. The complex of HLA-DR and its ligand (a peptide of at least 9 amino acids) constitutes a ligand for the TCR.

Integrins are receptors that mediate attachment between a cell and the tissues surrounding it and are involved in cell-cell and cell-matrix interactions. In mammals, 18 $\alpha$ and 8 $\beta$ subunits have been characterized. Both $\alpha$ and $\beta$ subunits contain two separate tails, both of which penetrate the plasma membrane and possess small cytoplasmic domains.

Integrin $\alpha$M (ITGAM; CD11b; macrophage-1 antigen (Mac-1); complement receptor 3 (CR3)) is a protein subunit of the heterodimeric integrin $\alpha$M$\beta$2 molecule. The second chain of $\alpha$M$\beta$2 is the common integrin $\beta$2 subunit (CD18). $\alpha$M$\beta$2 is expressed on the surface of many leukocytes including monocytes, granulocytes, macrophages and natural killer cells. It generally is believed that of $\alpha$M$\beta$2 mediates inflammation by regulating leukocyte adhesion and migration. Further, of $\alpha$M$\beta$2 is thought to have a role in phagocytosis, cell-mediated cytotoxicity, chemotaxis and cellular activation, as well as being involved in the complement system due to its capacity to bind inactivated complement component 3b (iC3b). The ITGAM subunit of integrin of $\alpha$M$\beta$2 is involved directly in causing the adhesion and spreading of cells, but cannot mediate cellular migration without the presence of the $\beta$2 (CD18) subunit.

CD61 (integrin $\beta$3; platelet glycoprotein Ma; ITGB3) is a cell surface protein composed of an $\alpha$-chain and a $\beta$-chain. A given chain may combine with multiple partners resulting in different integrins. CD61 is found along with the $\alpha$ IIb chain in platelets and is known to participate in cell adhesion and cell-surface mediated signaling.

CD63 (LAMP-3; ME491; MLA1; OMA81H) is a cell surface glycoprotein of the transmembrane 4 superfamily (tetraspanin family). Many of these cell surface receptors have four hydrophobic domains and mediate signal transduction events that play a role in the regulation of cell development, activation, growth and motility. CD63 forms complexes with integrins and may function as a blood platelet activation marker. It generally is believed that the sensitivity and specificity of measuring the upregulation of CD63 alone, or as part of a combination, is not specific enough to serve as a diagnostic marker for the diagnosis of IgE mediated allergy.

CD123 is the 70 kD transmembrane a chain of the cytokine interleukin-3 (IL-3) receptor. Alone, CD123 binds IL-3 with low affinity; when CD123 associates with CDw131 (common $\beta$ chain), it binds IL-3 with high affinity. CD123 does not transduce intracellular signals upon binding IL-3 and requires the $\beta$ chain for this function. CD123 is expressed by myeloid precursors, macrophages, dendritic cells, mast cells, basophils, megakaryocytes, and some B cells CD123 induces tyrosine phosphorylation within the cell and promotes proliferation and differentiation within the hematopoietic cell lines.

CD203c (ectonucleotide pyrophosphatase/phosphodiesterase 3; ENPP3) is an ectoenzyme constitutively and specifically expressed on the cell surface and within intracellular compartments of basophils, mast cells, and precursors of these cells. CD203c detection by flow cytometry has been used to specifically identify basophils within a mixed leukocyte suspension, since its expression is unique to basophils among the cells circulating in blood. The expression of CD203c is both rapidly and markedly upregulated following IgE-dependent activation. However, as with CD63, it is generally believed that the sensitivity and specificity of measuring the upregulation of CD203c alone, or as part of a combination, is not specific enough to serve as a diagnostic marker for the diagnosis of IgE mediated allergy. Further, the exact role of CD203c in basophil biology is unknown.

CD294 (G protein-coupled receptor 44; GPR44; CRTh2; DP2) is an integral membrane protein. This chemoattractant receptor homologous molecule is expressed on T helper type-2 cells. The transmembrane domains of these proteins mediate signals to the interior of the cell by activation of heterotrimeric G proteins that in turn activate various effector proteins that ultimately result a physiologic response.

The term "clone" as used herein refers to a population of cells formed by repeated division from a common cell.

The term "compatible" as used herein means that the components of a composition are capable of being combined with each other in a manner such that there is no interaction that would substantially reduce the efficacy of the composition under ordinary use conditions.

The term "Complement" as used herein refers to a system of plasma proteins that interact with pathogens to mark them for destruction by phagocytes. Complement proteins can be activated directly by pathogens or indirectly by pathogen-bound antibody, leading to a cascade of reactions that occurs on the surface of pathogens and generates active components with various effector functions.

The term "composition" as used herein refers to an aggregate material formed of two or more substances.

The transitional term "comprising", which is synonymous with "including," "containing," or "characterized by," is inclusive or open-ended and does not exclude additional, unrecited elements or method steps.

The term "concentration" as used herein refers to the amount of a substance in a given volume.

The term "concurrent" as used herein refers to occurring, or to operating, before, during or after an event, episode or time period.

The term "component" as used herein refers to a constituent part, element or ingredient.

The term "condition", as used herein, refers to a variety of health states and is meant to include disorders or diseases caused by any underlying mechanism or disorder, injury.

The term "connected" as used herein refers to being joined, linked, or fastened together in close association.

The term "contact" as used herein refers to the state or condition of touching or being in immediate proximity.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "inflammatory mediators" or "inflammatory cytokines" as used herein refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, and proinflammatory cytokines, including, but not limited to, interleukin-1-beta (IL-1β), interleukin-4 (IL-4), interleukin-6 (IL-6), interleukin-8 (IL-8), tumor necrosis factor-alpha (TNF-α), interferon-gamma (IF-γ), and interleukin-12 (IL-12).

Among the pro-inflammatory mediators, IL-1, IL-6, and TNF-α are known to activate hepatocytes in an acute phase response to synthesize acute-phase proteins that activate complement. Complement is a system of plasma proteins that interact with pathogens to mark them for destruction by phagocytes. Complement proteins can be activated directly by pathogens or indirectly by pathogen-bound antibody, leading to a cascade of reactions that occurs on the surface of pathogens and generates active components with various effector functions. IL-1, IL-6, and TNF-α also activate bone marrow endothelium to mobilize neutrophils, and function as endogenous pyrogens, raising body temperature, which helps eliminating infections from the body. A major effect of the cytokines is to act on the hypothalamus, altering the body's temperature regulation, and on muscle and fat cells, stimulating the catabolism of the muscle and fat cells to elevate body temperature. At elevated temperatures, bacterial and viral replication are decreased, while the adaptive immune system operates more efficiently.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by wellknown chemical modification methods (see, e.g., Glazer et al., Chemical Modification of Proteins, Selected Methods and Analytical Procedures, Elsevier Biomedical Press, New York (1975)).

The phrase "density-dependent inhibition of growth" as used herein refers to reduced response of cells upon reaching a threshold density. These cells recognize the boundaries of neighbor cells upon confluence and respond, depending on growth patterns, by forming a monolayer. Usually these cells transit through the cell cycle at reduce rate (grow slower).

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "differentiation" as used herein refers to a property of cells to exhibit tissue-specific differentiated properties in culture.

The term "dissolved gas molecules" as used herein refers to molecules (e.g., $O_2$, $CO_2$, etc.) dissolved in cell culture medium.

The term "dynamic" as used herein refers to changing conditions to which an agent must adapt.

The term "extracellular matrix" as used herein refers to a construct in a cell's external environment with which the cell interacts via specific cell surface receptors. The extracellular matrix serves many functions, including, but not limited to, providing support and anchorage for cells, segregating one tissue from another tissue, and regulating intracellular communication. The extracellular matrix is composed of an interlocking mesh of fibrous proteins and glycosaminoglycans (GAGs). Examples of fibrous proteins found in the extracellular matrix include collagen, elastin, fibronectin, and laminin. Examples of GAGs found in the extracellular matrix include proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached one or more glycosaminoglycans.

The term "cytometry" as used herein, refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and to collect cells (or other small particles) with measured characteristics that fall within a user-selected range of values.

The term "differential label" as used herein, generally refers to a stain, dye, marker, antibody or antibody-dye combination, or intrinsically fluorescent cell-associated molecule, used to characterize or contrast components, small molecules, macromolecules, e.g., proteins, and other structures of a single cell or organism. The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X¬rhodamine, Lissamine Rhodamine B, Texas Red, TruRed, and derivatives thereof.

Flow Cytometry

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus.

Flow cytometry utilizes a beam of light (usually laser light) of a single wavelength that is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analyzing fluctuations in brightness at each detector (usually one for each fluorescent emission peak) it then is possible to derive various types of information about the physical and chemical structure of each individual particle. FSC correlates with the cell volume and SSC depends on the inner complexity of the particle (i.e. shape of the nucleus, the amount and type of cytoplasmic granules or the membrane roughness).

FACS

The term "fluorescence-activated cell sorting" (also referred to as "FACS"), as used herein, refers to a method for sorting a heterogeneous mixture of biological cells into one or more containers, one cell at a time, based upon the specific light scattering and fluorescent characteristics of each cell.

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest.

Utilizing FACS, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Before the stream breaks into droplets the flow passes through a fluorescence measuring station where the fluorescent character of interest of each cell is measured. An electrical charging ring or plane is placed just at the point where the stream breaks into droplets. A charge is placed on the ring based on the prior light scatter and fluorescence intensity measurements, and the opposite charge is trapped on the droplet as it breaks from the stream. The charged droplets then fall through an electrostatic deflection system that diverts droplets into containers based upon their charge. In some systems the charge is applied directly to the stream while a nearby plane or ring is held at ground potential and the droplet breaking off retains charge of the same sign as the stream. The stream is then returned to neutral after the droplet breaks off.

The term "growth" as used herein refers to a process of becoming larger, longer or more numerous, or an increase in size, number, or volume.

The term "growth factor" as used herein refers to signal molecules involved in the control of cell growth and differentiation and cell survival.

The term "hybridoma cell" as used herein refers to an immortalized hybrid cell resulting from the in vitro fusion of an antibody-secreting B cell with a myeloma cell. For example, monoclonal antibodies (mAbs) can be generated by fusing mouse spleen cells from an immunized donor with a mouse myeloma cell line to yield established mouse hybridoma clones that grow in selective media.

The term "immunoglobulin (Ig)" as used herein refers to one of a class of structurally related proteins, each consisting of two pairs of polypeptide chains, one pair of identical light (L) (low molecular weight) chains ($\kappa$ or $\lambda$), and one pair of identical heavy (H) chains ($\gamma$, $\alpha$, $\mu$, $\delta$ and $\varepsilon$), usually all four linked together by disulfide bonds. On the basis of the structural and antigenic properties of the H chains, Igs are classified (in order of relative amounts present in normal human serum) as IgG, IgA, IgM, IgD, and IgE. Each class of H chain can associate with either $\kappa$ or $\lambda$ L chains. There are four subclasses of IgG immunoglobulins (IgG1, IgG2, IgG3, IgG4) having $\gamma$1, $\gamma$2, $\gamma$3, and $\gamma$4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

The term Ig refers not only to antibodies, but also to pathological proteins classified as myeloma proteins, which appear in multiple myeloma along with Bence Jones proteins, myeloma globulins, and Ig fragments.

Antibodies are serum proteins the molecules of which possess small areas of their surface that are complementary to small chemical groupings on their targets. Both light and heavy chains usually cooperate to form the antigen binding surface. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions.

All five immunoglobulin classes differ from other serum proteins in that they normally show a broad range of electrophoretic mobility and are not homogeneous. This heterogeneity—that individual IgG molecules, for example, differ from one another in net charge—is an intrinsic property of the immunoglobulins, and accounts for the libraries of antibodies each individual possesses.

The term "immunoglobulin fragment" ("Ig fragment") refers to a partial immunoglobulin molecule.

The term "in vitro immunization" is used herein to refer to primary activation of antigen-specific B cells in culture.

The term "interacted with" as used herein refers to a kind of action that occurs as two or more objects have an effect upon one another.

The term "interleukin" as used herein refers to a cytokine secreted, and acting on, leukocytes. Interleukins regulate cell growth, differentiation, and motility, and stimulates immune responses, such as inflammation. Examples of interleukins include, interleukin-1 (IL-1), interleukin-1$\beta$ (IL-1$\beta$), interleukin-6 (IL-6), interleukin-8 (IL-8), and interleukin-12 (IL-12).

The term "isolated" is used herein to refer to material, such as, but not limited to, a cell, nucleic acid, peptide, polypeptide, or protein, which is: (1) substantially or essentially free from components that normally accompany or interact with it as found in its naturally occurring environment.

The terms "label" or "labeled" as used herein refers to incorporation of a detectable marker or molecule.

The term "marker' as used herein refers to a receptor, or a combination of receptors, found on the surface of a cell. These markers allow a cell type to be distinguishable from other kinds of cells. Specialized protein receptors (markers) that have the capability of selectively binding or adhering to other signaling molecules coat the surface of every cell in the body. Cells use these receptors and the molecules that bind to them as a way of communicating with other cells and to carry out their proper function in the body.

The term "microfluidics" refers to a set of technologies that control the flow of minute amounts of liquids or dissolved gas molecules, typically measured in nano- and pico-liters in a miniaturized system. The microchips require only a small amount of sample and reagent for each process, and microscale reactions occur much faster because of the physics of small fluid volumes.

The term "modulate" as used herein means to regulate, alter, adapt, or adjust to a certain measure or proportion.

The term "monoclonal" as used herein refers to resulting from the proliferation of a single clone.

The term "monoclonal Ig" as used herein refers to a homogeneous immunoglobulin resulting from the proliferation of a single clone of plasma cells and which, during electrophoresis of serum, appears as a narrow band or "spike". It is characterized by H chains of a single class and subclass, and light chains of a single type.

The term "monolayer" as used herein refers to a layer of cells one cell thick, grown in a culture.

As used herein, the terms "osteoprogenitor cells," "mesenchymal cells," "mesenchymal stem cells (MSC)," or "marrow stromal cells" are used interchangeably to refer to multipotent stem cells that differentiate from CFU-F cells capable of differentiating along several lineage pathways into osteoblasts, chondrocytes, myocytes and adipocytes. When referring to bone or cartilage, MSCs commonly are known as osteochondrogenic, osteogenic, chondrogenic, or osteoprogenitor cells, since a single MSC has shown the ability to differentiate into chondrocytes or osteoblasts, depending on the medium.

The term "osteoblasts" as used herein refers to cells that arise when osteoprogenitor cells or mesenchymal cells, which are located near all bony surfaces and within the bone marrow, differentiate under the influence of growth factors. Osteoblasts, which are responsible for bone matrix synthesis, secrete a collagen rich ground substance essential for later mineralization of hydroxyapatite and other crystals. The collagen strands to form osteoids: spiral fibers of bone matrix. Osteoblasts cause calcium salts and phosphorus to precipitate from the blood, which bond with the newly formed osteoid to mineralize the bone tissue. Once osteoblasts become trapped in the matrix they secrete, they become osteocytes. From least to terminally differentiated, the osteocyte lineage is (i) Colony-forming unit-fibroblast (CFU-F); (ii) mesenchymal stem cell/marrow stromal cell (MSC); (3) osteoblast; (4) osteocyte.

The term "osteogenesis" refers to the formation of new bone from bone forming or osteocompetent cells.

The term "osteocalcin" as used herein refers to a protein constituent of bone; circulating levels are used as a marker of increased bone turnover.

The term "osteoclast" as used herein refers to the large multinucleate cells associated with areas of bone resorption bone resorption (breakdown).

The term "osteogenic factors" refers to the plethora of mediators associated with bone development and repair, including, but not limited to bone morphogenic proteins (BMPs), vascular endothelial growth factor (VEGF), basic fibroblast growth factor (bFGF), transforming growth factor beta (TGFβ), and platelet-derived growth factor (PDGF).

The term "perfusion" as used herein refers to the process of nutritive delivery of arterial blood to a capillary bed in biological tissue. Perfusion ("F") can be calculated with the formula $F=((PA-Pv)/R)$ wherein PA is mean arterial pressure, Pv is mean venous pressure, and R is vascular resistance. Tissue perfusion can be measured in vivo, by, for example, but not limited to, magnetic resonance imaging (MRI) techniques. Such techniques include using an injected contrast agent and arterial spin labeling (ASL) (wherein arterial blood is magnetically tagged before it enters into the tissue of interest and the amount of labeling is measured and compared to a control recording). Tissue perfusion can be measured in vitro, by, for example, but not limited to, tissue oxygen saturation ($StO_2$) using techniques including, but not limited to, hyperspectral imaging (HSI).

The terms "proliferation" and "propagation" are used interchangeably herein to refer to expansion of a population of cells by the continuous division of single cells into identical daughter cells.

The term "three-dimensional tissue construct" as used herein refers to a tissue like collection of cells and the intercellular substances surrounding them in a geometric configuration having length, width, and depth.

The terms "subject" and "patients" are used interchangeably herein and include animal species of mammalian origin, including humans.

The term "suspension culture" as used herein refers to cells which do not require attachment to substratum to grow, i.e. anchorage independent. Cell culture derived from blood are typically grown in suspension. Cells can grow as single cells or clumps. To subculture the cultures which grow as single cells they can be diluted. However, the cultures containing clumps need to have the clumps disassociated prior to subculturing of the culture.

The term "target" as used herein refers to a biological entity, such as, for example, but not limited to, a protein, cell, organ, or nucleic acid, whose activity can be modified by an external stimulus. Depending upon the nature of the stimulus, there may be no direct change in the target, or a conformational change in the target may be induced.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "tumor necrosis factor" (TNF) as used herein refers to a cytokine made by white blood cells in response to an antigen or infection, which induce necrosis (death) of tumor cells and possesses a wide range of pro-inflammatory actions. Tumor necrosis factor also is a multifunctional cytokine with effects on lipid metabolism, coagulation, insulin resistance, and the function of endothelial cells lining blood vessels.

The terms "VEGF-1" or "vascular endothelial growth factor-1" are used interchangeably herein to refer to a cytokine that mediates numerous functions of endothelial cells including proliferation, migration, invasion, survival, and permeability. VEGF is critical for angiogenesis.

According to one aspect, an ex vivo dynamic multiple myeloma (MM) cancer niche is created in a microfluidic device. The MM cancer niche comprises a dynamic ex vivo bone marrow (BM) niche suitable for dynamic propagation of a biospecimen comprising human myeloma cells. It comprises a three-dimensional tissue construct containing a dynamic ex vivo bone marrow (BM) niche comprising a mineralized bone-like tissue comprising (a) viable osteoblasts self-organized into cohesive multiple cell layers and (b) an extracellular matrix secreted by the viable adherent osteoblasts; and a microenvironment dynamically perfused by nutrients and dissolved gas molecules, into which human myeloma cells from a biospecimen composition containing mononuclear cells and the human myeloma cells are placed. The human myeloma cells are in contact with osteoblasts of the BM niche and are maintained viable by the MM cancer niche. According to another embodiment, the BM niche provides a perfused microenvironment to supports propagation of the human myeloma cells. According to another embodiment, the human myeloma cells are cellular components of a bone marrow aspirate. According to another embodiment, the human myeloma cells are cellular components of peripheral blood. According to another embodiment, the human myeloma cells are cellular components of a core biopsy. According to another embodiment, the biospecimen comprises plasma autologous to the patient. According to another embodiment, the ex vivo dynamic multiple myeloma (MM) cancer niche is suitable for dynamic propagation of the human myeloma cells for at least 7 days. According to another embodiment, the sample of human myeloma cells added to the BM niche constitutes $1\times10^4$ to $1\times10^5$ mononuclear cells.

According to another embodiment, propagation of MM cells can result in deterioration of the 3D ossified tissue of the BM niche.

According to another aspect, the ex vivo dynamic multiple myeloma (MM) cancer niche is prepared by (1) acquiring a biospecimen from a subject in need thereof, wherein the biospecimen comprises viable multiple myeloma cells;

(2) preparing a biospecimen composition comprising the viable multiple myeloma cells and plasma autologous to the subject;

(3) preparing a three-dimensional tissue construct containing a dynamic ex vivo bone marrow (BM) niche comprising (i) a mineralized bone-like tissue comprising (a) viable osteoblasts self-organized into cohesive multiple cell layers and (b) an extracellular matrix secreted by the viable adherent osteoblasts; and (ii) a microenvironment dynamically perfused by nutrients and dissolved gas molecules;

(4) adding the biospecimen composition to the three-dimensional tissue construct containing the dynamic ex vivo bone marrow (BM) niche so that the MM cells are in contact with the osteoblasts of the BM niche, and (5) forming the dynamic ex vivo MM niche, which is capable of maintaining viability of the human myeloma cells.

According to one embodiment of the method, the MM niche further comprises osteoblast-secreted and MM cell-secreted soluble cytokines and growth factors. According to another embodiment, the MM cells are adherent to osteoblasts of the BM niche. According to another embodiment, the MM cells adhere to the osteoblasts of the BM niche by cell-cell interactions. According to another embodiment, the human myeloma cells are cellular components of a bone marrow aspirate. According to another embodiment, the human myeloma cells are cellular components of peripheral blood. According to another embodiment, the human myeloma cells are cellular components of a core biopsy. According to another embodiment, the ex vivo dynamic multiple myeloma (MM) cancer niche is suitable for dynamic propagation of the human myeloma cells for at least 7 days. According to another embodiment, the sample of human myeloma cells added to the BM niche constitutes $1\times10^4$ to $1\times10^5$ mononuclear cells. According to another embodiment, propagation of the MM cells is capable of producing deterioration of the 3D ossified tissue of the BM niche.

According to another aspect, the described one aspect, the described invention provides a method for assessing chemotherapeutic efficacy of a chemotherapeutic agent on viable human multiple myeloma cells obtained from a subject.

The term "chemotherapy", in its most general sense, refers to the treatment of disease by means of chemical substances or drugs. In popular usage, it refers to antineoplastic drugs used alone or in combination as a cytotoxic standardized regimen to treat cancer. In its non-oncological use, "chemotherapy" may refer, for example, to antibiotics.

Chemotherapy is employed as part of a multimodality approach to the initial treatment of many tumors, including, but not limited to, MM, breast cancer, colon cancer and locally advanced stages of head and neck, lung, cervical, and esophageal cancer, soft tissue sarcomas, pediatric solid tumors and the like. The basic approaches to cancer treatment are constantly changing. Newer therapies have improved patient survival, and, in some cases, turned cancer into a chronic disease.

The majority of chemotherapeutic drugs can be divided into several categories including, but not limited to, (1) alkylating agents; (2) antimetabolites; (3) natural products; (4) hormones and related agents; (5) biologics; (6) miscellaneous agents; and (7) those effective in treating MM.

1. Alkylating Agents and their Side-Effects

Alkylating agents used in chemotherapy encompass a diverse group of chemicals that have in common the capacity to contribute, under physiological conditions, alkyl groups to biologically vital macromolecules, such as DNA. For several of the most valuable agents, such as cyclophosphamides and nitrosoureas, the active alkylating moieties are generated in vivo after complex metabolic reactions.

As shown in Table 3, there are five major types of alkylating agents used in chemotherapy of neoplastic diseases: (1) nitrogen mustards; (2) ethylenimimes; (3) alkyl sulfonates; (4) nitrosoureas; and (5) triazenes.

TABLE 3

Examples of Alkylating Agents Useful for Treating Neoplastic Diseases.

| Class | Type of Agent | Example | Neoplasms/Disease | Proposed Mechanism of Action |
|---|---|---|---|---|
| Alkylating Agents | Triazene | Temozolomide (Temodar ®) | Glioma; malignant melanoma | temozolomide is converted at physiologic pH to the short-lived active compound, monomethyl triazeno imidazole carboxamide (MTIC). The cytotoxicity of MTIC is due primarily to methylation of DNA which results in inhibition of DNA replication |

TABLE 3-continued

Examples of Alkylating Agents Useful for Treating Neoplastic Diseases.

| Class | Type of Agent | Example | Neoplasms/Disease | Proposed Mechanism of Action |
|---|---|---|---|---|
| Alkylating Agents | Alkyl Sulfonate | Busulfan (Myleran ®) | Chronic granulocytic leukemia | appears to act through the alkylation of DNA |
| Alkylating Agents | Nitrogen Mustard | Cyclophosamide (Cytoxan ®) | breast cancer; different types of leukemia including acute lymphoblastic leukemia ("ALL"), acute myeloid leukemia ("AML"), chronic lymphocytic leukemia ("CLL"), and chronic myelogenous leukemia ("CML"); Hodgkin lymphoma; multiple myeloma; mycosis fungoides; neuroblastoma; non-Hodgkin lymphoma; ovarian cancer; and retinoblastoma. | In the liver, cyclophosphamide is converted to the active metabolites aldophosphamide and phosphoramide mustard, which bind to DNA, thereby inhibiting DNA replication and initiating cell death. |
| Alkylating Agents | Nitrogen Mustard | Ifosamide (Mitoxana ®, Ifex ®) | Acute and chronic lymphocytic leukemias; Hodgkin's disease; non-Hodgkin's lymphomas; multiple myeloma; neuroblastoma; breast, ovary, lung cancer; Wilm's tumor; cervix, testis cancer; soft-tissue sarcomas | alkylates and forms DNA crosslinks, thereby preventing DNA strand separation and DNA replication |
| Alkylating Agents | Nitrogen Mustard | Melphalan (L-sarcolysin; Alkeran ®) | Multiple myeloma; breast, ovarian cancer | alkylates DNA at the N7 position of guanine and induces DNA inter-strand cross-linkages, resulting in the inhibition of DNA and RNA synthesis and cytotoxicity against both dividing and non-dividing tumor cells |
| Alkylating Agents | Nitrosourea | Carmustine (BCNU; Gliadel Wafer ®) | Hodgkin's disease, non-Hodgkin's lymphomas, primary brain tumors, multiple myeloma, malignant myeloma | alkylates and cross-links DNA during all phases of the cell cycle, resulting in disruption of DNA function, cell cycle arrest, and apoptosis. This agent also carbamoylates proteins, including DNA repair enzymes, resulting in an enhanced cytotoxic effect |

Chemotherapeutic alkylating agents become strong electrophiles through the formation of carbonium ion intermediates or of transition complexes with the target molecules. This results in the formation of covalent linkages by alkylation of various nucleophilic moieties, such as phosphate, amino, sulfhydryl, hydroxyl, carboxyl, and imidazole groups. The chemotherapeutic and cytotoxic effects of alkylating agents are related directly to alkylation of DNA, which has several sites that are susceptible to the formation of a covalent bond.

The most important pharmacological actions of alkylating agents are those that disturb DNA synthesis and cell division. The capacity of these drugs to interfere with DNA integrity and function in rapidly proliferating tissues provides the basis for their therapeutic applications and for many of their toxic properties. Whereas certain alkylating agents may have damaging effects on tissues with normally low mitotic indices, such as the liver, kidney, and mature lymphocytes, they are most cytotoxic to rapidly proliferating tissues in which a large proportion of the cells are in division. These alkylating compounds may readily alkylate nondividing cells, but their cytotoxicity is enhanced markedly if DNA is damaged in cells programmed to divide. In contrast to many other antineoplastic agents, the effects of the alkylating drugs, although dependent on proliferation, are not cell-cycle-specific, and the drugs may act on cells at any stage of the cycle. However, the toxicity is usually expressed when the cell enters the S phase and the progression through the cycle is blocked. DNA alkylation itself may not be a lethal event if DNA repair enzymes can correct the lesions in DNA prior to the next cellular division.

Alkylating agents differ in their patterns of antitumor activity and in the sites and severity of their side effects. Most cause dose-limiting toxicity to bone marrow elements and to intestinal mucosa and alopecia. Most alkylating agents, including nitrogen mustard, melphalan, chloramucil, cyclophosphamide, and ifosfamide, produce an acute myelosuppression. Cyclophosphamide has lesser effects on peripheral blood platelet counts than do other alkylating agents. Busuflan suppresses all blood elements and may produce a prolonged and cumulative myelosuppression lasting months. BCNU and other chloroethylnitrosoureas cause delayed and prolonged suppression of both platelets and granulocytes.

Alkylating agents also suppress both cellular and humoral immunity, although immunosuppression is reversible at doses used in most anticancer protocols.

In addition to effects on the hematopoietic system, alkylating agents are highly toxic to dividing mucosal cells. The mucosal effects are particularly significant in high-dose chemotherapy protocols associated with bone marrow reconstitution; they may predispose a patient to bacterial sepsis arising from the gastrointestinal tract. Generally, mucosal and bone marrow toxicities occur predictably with conventional doses of these drugs; however other organ toxicities, although less common, can be irreversible and sometimes lethal. All alkylating agents have caused pulmonary fibrosis.

Heart failure that occurs after high-dose cyclophosphamide, ifosfamide, or mitomycin treatment is manifested by neurohumoral activation without concomitant cardiomyocyte necrosis. Mild functional mitral regurgitation also may develop in cyclophosphamide-treated patients. Zver, S. et al., Intl J. Hematol. 85(5): 408-14 (2007).

In high-dose protocols, a number of toxicities not seen at conventional doses become dose-limiting. For example, endothelial damage that may precipitate venoocclusive disease of the liver; the nitrosoureas, after multiple cycles of therapy, may lead to renal failure; ifosamide frequently causes a central neurotoxicity (manifest in the form of nausea and vomiting), with seizures, coma and sometimes death. Cyclophosamide and ifosfamide release a nephrotoxic and urotoxic metabolite, acrolein, which causes severe hemorrhagic cystitis, an undesirable effect that in high-dose regimens can be prevented by coadministration of mesna (2-mercaptoethanesulfonate).

The more unstable alkylating agents (particularly nitrogen mustards and the nitrosoureas) have strong vesicant properties, damage veins with repeated use, and if extravasated, produce ulceration.

As a class of drugs, the alkylating agents are highly leukomogenic. Acute nonlymphocytic leukemia may affect up to 5% of patients treated on regimens containing alkylating drugs. Melphalan, the nitrosoureas, and procarbazine have the greatest propensity to cause leukemia. Additionally, all alkylating agents have toxic effects on the male and female reproductive systems.

Examples of alklyating agents include, but are not limited to, cyclophosphamide (Cytotaxan®), a synthetic alkylating agent chemically related to the nitrogen mustards; temozolomide (Temodar®), a triazene analog of dacarbazine; busulfan (Myleran®), a synthetic derivative of dimethane sulfonate; ifosfamide (Ifex®), a synthetic analog of cyclophosphamide; mesna (Mesnex®), a sulfhydryl compound; melphalan hydrochloride (Alkeran®), an orally available phenylalanine derivative of nitrogen mustard; and the nitrosoureas carmustine (BiCNU®) and lomustine (CEENU®).

2. Antimetabolites

Antimetabolites are a class of drugs that interfere with DNA and RNA growth by preventing purines (azathioprine, mercaptopurine) or pyrimidine from becoming incorporated into DNA during the S phase of the cell cycle, thus stopping normal development and division. Antimetabolites commonly are used to treat leukemias, tumors of the breast, ovary and the intestinal tract, as well as other cancers.

Antimetabolites include folic acid analogs, such as methotrexate and aminopterin; pyrimidine analogs, such as fluorouracil and fluorodeoxyuridine; cytarabine (cytosine arabinoside); and purine analogs, such as mercaptopurine, thioguanine, fludarabine phosphate, pentostatin (2'-deoxycoformycin), and cladribine. Table 4 presents examples of some antimetabolites useful for treating neoplastic diseases.

TABLE 4

Examples of Antimetabolites Useful for Treating Neoplastic Diseases

| Class | Type of Agent | Example | Proposed Mechanism of Action | Neoplasms/Disease |
|---|---|---|---|---|
| Antimetabolites | Pyrimidine Analog | 5-fluorouracil (fluorouracil; 5-FU) | Fluorouracil and its metabolites possess a number of different mechanisms of action. In vivo, fluorouracil is converted to the active metabolite 5-fluoroxyuridine monophosphate (F-UMP); replacing uracil, F-UMP incorporates into RNA and inhibits RNA processing, thereby inhibiting cell growth. Another active metabolite, 5-5-fluoro-2'-deoxyuridine-5'-O-monophosphate (F-dUMP), inhibits thymidylate synthase, resulting in the depletion of thymidine triphosphate (TTP), one of the four nucleotide triphosphates used in the in vivo synthesis of DNA. Other fluorouracil metabolites incorporate into both RNA and DNA; incorporation into RNA results in major effects on both RNA processing and functions. | palliative treatment of colorectal cancer, breast cancer, stomach cancer, and pancreatic cancer. In combination, with other drugs it is used to treat locally advanced squamous cell carcinoma of the head and neck, gastric adenocarcinoma, and Stage III colorectal cancer. |

TABLE 4-continued

Examples of Antimetabolites Useful for Treating Neoplastic Diseases

| Class | Type of Agent | Example | Proposed Mechanism of Action | Neoplasms/Disease |
|---|---|---|---|---|
| Antimetabolites | Pyrimidine Analog | Capecitabine (Xeloda ®) | As a prodrug, capecitabine is selectively activated by tumor cells to its cytotoxic moiety, 5-fluorouracil (5-FU); subsequently, 5-FU is metabolized to two active metabolites, 5-fluoro-2-deoxyuridine monophosphate (FdUMP) and 5-fluorouridine triphosphate (FUTP) by both tumor cells and normal cells. FdUMP inhibits DNA synthesis and cell division by reducing normal thymidine production, while FUTP inhibits RNA and protein synthesis by competing with uridine triphosphate for incorporation into the RNA strand. | metastatic (Stage III) colorectal cancer and metastatic breast cancer. |
| Antimetabolites | Pyrimidine Analog | Gemcitabine (gemcitabine hydrochloride, Gemzar ®) | Gemcitabine is converted intracellularly to the active metabolites difluorodeoxycytidine di- and triphosphate (dFdCDP, dFdCTP). dFdCDP inhibits ribonucleotide reductase, thereby decreasing the deoxynucleotide pool available for DNA synthesis; dFdCTP is incorporated into DNA, resulting in DNA strand termination and apoptosis. | pancreatic cancer, ovarian cancer, breast cancer, and non-small cell lung cancer. |
| Antimetabolites | Pyrimidine Analog | floxuridine (FUDR) | inhibits thymidylate synthetase, resulting in disruption of DNA synthesis and cytotoxicity. This agent is also metabolized to fluorouracil and other metabolites that can be incorporated into RNA and inhibit the utilization of preformed uracil in RNA synthesis. | the palliative treatment of gastrointestinal adenocarcinoma metastatic to the liver. |
| Antimetabolites | Purine Analog | 2-chlorodeoxyadenosine (cladribine, Leustatin ®) | cladribine triphosphate, a phosphorylated metabolite of cladribine, incorporates into DNA, resulting in single-strand breaks in DNA, depletion of nicotinamide adenine dinucleotide (NAD) and adenosine triphosphate (ATP), and apoptosis | Hairy cell leukemia, chronic lymphocytic leukemia, non-Hodgkin's lymphomas |
| Antimetabolites | Pyrimidine Analog | Decitabine (Dacogen ®) | incorporates into DNA and inhibits DNA methyltransferase, resulting in hypomethylation of DNA and intra-S-phase arrest of DNA replication | Myelodysplastic syndromes including refractory anemia and chronic myelomonocytic leukemia |
| Antimetabolites | Purine Analog | fludarabine phosphate (Fludara ®) | blocks cells from making DNA; purine antagonist and a type of ribonucleotide reductase inhibitor | refractory B-cell chronic lmphocytic leukemia |
| Antimetabolites | Purine Analog | Mercaptopurine (6-mercaptopurine; 6-MP; Purinethol ®) | a thiopurine-derivative antimetabolite with antineoplastic and immunosuppressive activities. | Acute lymphocytic, acute granulocytic, and chronic granulocytic leukemias |

TABLE 4-continued

Examples of Antimetabolites Useful for Treating Neoplastic Diseases

| Class | Type of Agent | Example | Proposed Mechanism of Action | Neoplasms/Disease |
|---|---|---|---|---|
| Antimetabolites | Purine Analog | 2'-deoxycoformycin (Nipent®, pentostatin) | binds to and inhibits adenine deaminase (ADA), an enzyme essential to purine metabolism | Hairy cell leukemia |
| Antimetabolites | Purine Analog | Dacarbazine (DTIC-Dome®) | alkylates and cross-links DNA during all phases of the cell cycle, resulting in disruption of DNA function, cell cycle arrest, and apoptosis | metastatic melanoma, Hodgkin's lymphoma |
| Antimetabolites | Folic Acid Analogs | Pemetrexed disodium (Alimta®) | binds to and inhibits the enzyme thymidylate synthase (TS) which catalyses the methylation of 2'-deoxyuridine-5'-monophosphate (dUMP) to 2'-deoxythymidine-5'-monophosphate (dTMP), an essential precursor in DNA synthesis | Mesothelioma, non-small cell lung cancer |
| Antimetabolite | Folic Acid Analog | Methotrexate (methotrexate sodium, amethopterin, Folex®, Mexate®, Rheumatrex®) | binds to and inhibits the DHFR, resulting in inhibition of purine nucleotide and thymidylate synthesis and, subsequently, inhibition of DNA and RNA syntheses | chorioadenoma destruens, choriocarcinoma, acute lymphoblastic leukemia, breast cancer, lung cancer, certain types of head and neck cancer, advanced non-Hodgkin lymphoma, and osteosarcoma; rheumatoid arthritis and psoriasis |
| Antimetabolite | Cytidine analog | Cytarabine (cytosine arabinoside) | antimetabolite analog of cytidine with a modified sugar moiety (arabinose instead of ribose). Cytarabine is converted to the triphosphate form within the cell and then competes with cytidine for incorporation into DNA. Because the arabinose sugar sterically hinders the rotation of the molecule within DNA, DNA replication ceases, specifically during the S phase of the cell cycle. This agent also inhibits DNA polymerase, resulting in a decrease in DNA replication and repair. | Acute non-lymphatic leukemia, acute lymphocytic leukemia, blast phase chronic myelocytic leukemia |

2.1. Anti-Folates and their Side-Effects

Folic acid is an essential dietary factor from which is derived a series of tetrahydrofolate cofactors that provide single carbon groups for the synthesis of precursors of DNA (thymidylate and purines) and RNA (purines). The enzyme dihydrofolate reductase ("DHFR") is the primary site of action of most anti-folates. Inhibition of DHFR leads to toxic effects through partial depletion of tetrahydrofolate cofactors that are required for the synthesis of purines and thymidylate.

Examples of anti-folates include, but are not limited to, methotrexate and Pemetrexed disodium. The most commonly used anti-folate is methotrexate (methotrexate sodium, amethopterin, Folex®, Mexate®, Rheumatrex®), which is an antimetabolite and antifolate agent with antineoplastic and immunosuppressant activities. Pemetrexed disodium (Alimta®) is the disodium salt of a synthetic pyrimidine-based antifolate.

2.2. Pyrmidine Analogs and their Side-Effects

Pyrmidine analogs are a diverse group of drugs with the capacity to inhibit biosynthesis of pyrimidine nucleotides or to mimic these natural metabolites to such an extent that the analogs interfere with the synthesis or function of nucleic acids. Drugs in this group have been employed in the treatment of diverse afflictions, including neoplastic diseases, psoriasis and infections caused by fungi and DNA-containing viruses.

Examples of pyrimidine analogs include, but are not limited to, 5-Fluorouracil (fluorouracil, 5-FU, Adrucil®, Efudex®, Fluorplex®), an antimetabolite fluoropyrimidine analog of the nucleoside pyrimidine with antineoplastic activity; floxuridine, a fluorinated pyrimidine monophosphate analogue of 5-fluoro-2'-deoxyuridine-5'-phosphate (FUDR-MP) with antineoplastic activity; capecitabine (Xeloda®), an antineoplastic fluoropyrimidine carbamate; and gemcitabine hydrochloride (Gemzar®), the salt of an analog of the antimetabolite nucleoside deoxycytidine with antineoplastic activity.

2.3. Purine Analogs and their Side-Effects

Several analogs of natural purine bases, nucleosides and nucleotides useful in the treatment of malignant diseases (mercaptopurine, thioguanine) and for immunosuppressive (azatioprine) and antiviral (acyclovir, ganciclovir, vidarabine, zidovudine) therapies have been identified.

The purine analogs mercaptopurine and its derivative azatioprine are among the most clinically useful drugs of the antimetabolite class. Examples of purine analogs include, but are not limited to, mercaptopurine (Purinethol®), a thiopurine-derivative antimetabolite with antineoplastic and immunosuppressive activities; decitabine (Dacogen®), a cytidine antimetabolite analogue with potential antineoplastic activity; and dacarbazine (DTIC-DOME®), a triazene derivative with antineoplastic activity.

3. Natural Products and their Side-Effects

Many chemotherapeutic agents are found or derived from natural resources. Table 5 shows examples of chemotherapeutic drugs classified as natural products.

TABLE 5

Examples of Natural Products Useful to Treat Neoplastic Diseases

| Class | Type of Agent | Example | Proposed Mechanism of Action | Neoplasms/Disease |
| --- | --- | --- | --- | --- |
| Natural Products | *Vinca* Alkaloid | Vincristine (vincristine sulfate) | binds irreversibly to microtubules and spindle proteins in S phase of the cell cycle and interferes with the formation of the mitotic spindle, thereby arresting tumor cells in metaphase | Acute lymphocytic leukemia, neuroblastoma, Wilm's tumor, rhabdomyosarcoma, Hodgkin's disease, non-Hodgkin's lymphomas, small-cell lung cancer |
| Natural Products | *Vinca* Alkaloid | Vinblastine (vinblastine sulfate, VLB) | binds to tubulin and inhibits microtubule formation, resulting in disruption of mitotic spindle assembly and arrest of tumor cells in the M phase of the cell cycle | Hodgkin's disease, non-Hodgkin's lymphomas, breast and testis cancer |
| Natural Products | *Vinca* Alkaloid | Vinorelbine tartrate (Navelbine ®) | binds to tubulin, thereby inhibiting tubulin polymerization into microtubules and spindle formation and resulting in apoptosis of susceptible cancer cells. | Advanced non-small cell lung cancer |
| Natural Products | Taxane | Paclitaxel (Taxol ®) | inhibitor of mitosis, differing from the vinca alkaloids and colchicine derivatives in that it promotes rather than inhibits microtubule formation | Ovarian, breast, lung, head and neck cancer; used in combination therapy of cisplatin-refractory ovarian, breast, (non-small cell) lung, esophagus, bladder, and head and neck cancers |
| Natural Products | Epothilone | Ixabepilone (Ixempra ®, INN, azaepothilone B) | binds to tubulin and promotes tubulin polymerization and microtubule stabilization, thereby arresting cells in the G2-M phase of the cell cycle and inducing tumor cell apoptosis | Non-Hodgkin's lymphoma; breast cancer |
| Natural Products | Anthracycline | Daunorubicin (Cerubidine ®, daunomycin, rubidomycin) | daunorubicin exhibits cytotoxic activity through topoisomerase-mediated interaction with DNA, thereby inhibiting DNA replication and repair and RNA and protein synthesis | Acute granulocytic and acute lymphocytic leukemias |
| Natural Products | Anthracycline | Epirubicin (Ellence ®) | intercalates into DNA and interacts with topoisomerase II, thereby inhibiting DNA replication and repair and RNA and protein synthesis | Breast cancer |
| Natural Products | Anthracycline | Doxorubicin (Doxil ®, doxorubicin hydrochloride, Adriamycin ®, Rubex ®) | intercalates between base pairs in the DNA helix, thereby preventing DNA replication and ultimately inhibiting protein synthesis; | Soft-tissue, osteogenic, and other sarcomas; Hodgkin's disease, non-Hodgkin's lymphomas; acute leukemias; breast, genitourinary, thyroid, lung, |

TABLE 5-continued

Examples of Natural Products Useful to Treat Neoplastic Diseases

| Class | Type of Agent | Example | Proposed Mechanism of Action | Neoplasms/Disease |
|---|---|---|---|---|
| Natural Products | Anthracycline | Idarubicin (idarubicin hydrochloride, Idamycin PFS ®) | inhibits topoisomerase II which results in an increased and stabilized cleavable enzyme-DNA linked complex during DNA replication and subsequently prevents the ligation of the nucleotide strand after double-strand breakage intercalates into DNA and interferes with the activity of topoisomerase II, thereby inhibiting DNA replication, RNA transcription and protein synthesis | stomach cancer; neuroblastoma Acute myeloid leukemia |
| Natural Products | Anthracenedione | Mitoxantrone (Novantrone ®) | stimulates the formation of strand breaks in DNA (mediated by topoisomerase II) and also by intercalating with DNA | Acute granulocytic leukemia, breast and prostate cancer |
| Natural Products | Antibiotic | Mitomycin (mitocyin C; Mutamycin ®) | bioreduced mitomycin C generates oxygen radicals, alkylates DNA, and produces interstrand DNA cross-links, thereby inhibiting DNA synthesis. Preferentially toxic to hypoxic cells, mitomycin C also inhibits RNA and protein synthesis at high concentrations | Stomach, cervix, colon, breast, pancreas, bladder, head and neck cancer |
| Natural Products | Camptothecin | Irinotecan (Camptosar ®, irinotecan hydrochloride) | prodrug, is converted to a biologically active metabolite 7-ethyl-10-hydroxy-camptothecin (SN-38) by a carboxylesterase-converting enzyme. One thousand-fold more potent than its parent compound irinotecan, SN-38 inhibits topoisomerase I activity by stabilizing the cleavable complex between topoisomerase I and DNA, resulting in DNA breaks that inhibit DNA replication and trigger apoptotic cell death | Ovarian cancer, small cell lung cancer, colon cancer |
| Natural Products | Camptothecin | Topotecan (Hycamtin ®, topotecan hydrochloride) | during the S phase of the cell cycle, topotecan selectively stabilizes topoisomerase I-DNA covalent complexes, inhibiting religation of topoisomerase I-mediated single-strand DNA breaks and producing potentially lethal double-strand DNA breaks when complexes are encountered by the DNA replication machinery | Ovarian cancer, small cell lung cancer, colon cancer |
| Natural Products | Epipodophyllotoxin | Etoposide (VePesid ®) | binds to and inhibits topoisomerase II and its function in ligating cleaved DNA molecules, | Testis, small-cell lung and other lung, breast cancer; Hodgkin's disease, non-Hodgkin's lymphomas, acute |

TABLE 5-continued

Examples of Natural Products Useful to Treat Neoplastic Diseases

| Class | Type of Agent | Example | Proposed Mechanism of Action | Neoplasms/Disease |
|---|---|---|---|---|
| | | | resulting in the accumulation of single- or double-strand DNA breaks, the inhibition of DNA replication and transcription, and apoptotic cell death | granulocytic leukemia, Kaposi's sarcoma |
| Natural Products | Epipodophyllotoxin | Teniposide (Vumon ®) | forms a ternary complex with the enzyme topoisomerase II and DNA, resulting in dose-dependent single- and double-stranded breaks in DNA, DNA: protein cross-links, inhibition of DNA strand religation, and cytotoxicity | Testis, small-cell lung and other lung, breast cancer; Hodgkin's disease, non-Hodgkin's lymphomas, acute granulocytic leukemia, Kaposi's sarcoma |
| Natural Products | Epipodophyllotoxin | Etoposide phosphate (Etopophos ®) | binds to the enzyme topoisomerase II, inducing double-strand DNA breaks, inhibiting DNA repair, and resulting in decreased DNA synthesis and tumor cell proliferation. Cells in the S and G2 phases of the cell cycle are most sensitive to this agent. | Testicular tumors, small cell lung cancer |
| Natural Products | Antibiotic | Amphotericin B | binds to ergosterol, an essential component of the fungal cell membrane, resulting in depolarization of the membrane; alterations in cell membrane permeability and leakage of important intracellular components; and cell rupture. This agent may also induce oxidative damage in fungal cells and has been reported to stimulate host immune cells. | Induction chemotherapy for childhood acute leukemia |

3.1. Antimitotic Drugs 3.1.1. Vinca Alkaloids and their Side-Effects

The vinca alkaloids, cell-cycle-specific agents that, in common with other drugs, such as colchicine, podophyllotoxin, and taxanes, block cells in mitosis, exerts their biological activities by specifically binding to tubulin, thereby blocking the ability of protein to polymerize into microtubules, and arresting cell division in metaphase through disruption of the microtubules of the mitotic apparatus. In the absence of an intact mitotic spindle, the chromosomes may disperse throughout the cytoplasm or may clump in unusual groupings. Both normal and malignant cells exposed to vinca alkaloids undergo changes characteristic of apoptosis.

Examples of vinca alkaloids include, but are not limited to, vincristine sulfate, a salt of a natural alkaloid isolated from the plant Vinca rosea Linn; vinblastine, a natural alkaloid isolated from the plant Vinca rosea Linn; and vinorelbine. Both vincristine and vinblastine, as well as the analog vinorelbine, have potent and selective antitumor effects, although their actions on normal tissue differ significantly.

3.1.2. Taxanes

The taxanes include, for example, but not limited to, paclitaxel, extracted from the Pacific yew tree *Taxus brevifolia*, and docetaxel (Taxotere®), a semi-synthetic, second-generation taxane derived from a compound found in the European yew tree *Taxus baccata*.

3.2. Epipodophyllotoxins and their Side-Effects

Podophyllotoxin is the active principle extracted from the mandrake plant *Podophyllum peltatum* from which two semisynthetic glycosides, etoposide and teniposide, have been developed.

3.3. Camptothecin Analogs and their Side-Effects

Camptothecins target the enzyme topoisomerase I. The parent compound, camptothecin, was first isolated from the Chinese tree *Camptotheca acuminata*. Although the parent camptothecin compound demonstrated antitumor activity, its severe and unpredictable toxicity, principally myelosuppression and hemorrhagic cystitis limited its use. The most widely used camptothecin analogs are irinotecan and toptecan, which are less toxic and more soluble.

3.4. Anti-Tumor Antibiotics

Antitumor antibiotics are compounds that have cytotoxic as well as antimicrobial properties. Most commonly used in neoplastic disease treatment are the actinomycins and anthracyclines.

3.4.1. Actinomycin

An exemplary actinomycin includes Dactinomycin (Actinomycin D), produced by *Streptomyces parvullus*. This highly toxic agent inhibits rapidly proliferating cells of normal and neoplastic origin.

3.4.2. Anthracyclines

The anthracycline antibiotics and their derivatives are produced by the fungus *Streptomyces peucetius* var. *caesius*. Anthracyclines and anthracenediones can intercalate with DNA. Accordingly, many functions of DNA are affected, including DNA and RNA synthesis. Single-strand and double-strand breaks occur, as does sister chromatid exchange; thus these compounds are both mutagenic and carcinogenic. Scission of DNA is believed to be mediated by drug binding to DNA and topoisomerase II that prevents the resealing of DNA breaks created by the enzyme.

Examples of anthracyclines include, but are not limited to, idarubicin hydrochloride, a semisynthetic 4-demethoxy analog of daunorubicin (daunorubicin hydrochloride, daunomycin, rubidomycin; Cerubidine®); doxorubicin (doxorubicin hydrochloride, Adriamycin®, Rubex®); as well as several analogs of doxorubicin including valrubicin (Valstar®) (for intravescial therapy of BCG-refractory urinary bladder carcinoma) and epirubicin (4'-epidxorubicin, Ellence®) (as a component of adjuvant therapy following resection of early lymph-node-positive breast cancer).

Additional antibiotic antineoplastics include, but are not limited to, mitoxantrone (Novotrone®), an anthracenedione; and bleomycin antibiotics, fermentation products of *Streptomyces verticillus* that cleave DNA, and includes bleomycin sulfate (Blenoxane®); and mitomycin (mitomycin-C, Mutamycin®), an antibiotic isolated from *Streptomyces caespitosus*.

4. Biologics

Generally, the term "biologics" as used herein refers to compounds that are produced by biological processes, including those utilizing recombinant DNA technology. Biologic compounds include agents or approaches that beneficially affect a patient's biological response to a neoplasm. Included are agents that act indirectly to mediate their anti-tumor effects (e.g., by enhancing the immunological response to neoplastic cells) or directly on the tumor cells (e.g., differentiating agents). Table 6 shows examples of chemotherapeutic agents that are classified as biologics.

TABLE 6

Examples of Biologics Useful for Treating Neoplastic Diseases

| Class | Type of Agent | Example | Proposed Mechanism of Action | Neoplasms/Disease |
|---|---|---|---|---|
| Biologics | Granulocyte-Colony Stimulating Factor | Filgrastim (Neupogen ®) | In vitro, G-CSF expands the population of neutrophil granulocyte precursors, augments granulocyte function by enhancing chemotaxis and antibody-dependent cellular cytotoxicity, and enhances the mobilization of stem cells in the peripheral blood following cytotoxic chemotherapy | Neutropenia |
| Biologics | Monoclonal Antibody | Bevacizumab (Avastin ®) | binds to and inhibits the biologic activity of human vascular endothelial growth factor ("VEGF") | Colorectal cancer, non-small cell lung cancer, breast cancer |
| Biologics | Granulocyte-Macrophage Colony Stimulating Factor | Sargramostim (Leukine ®) | used following induction chemotherapy in patients with acute myelogenous leukemia (AML) to shorten the time to neutrophil recovery and to reduce the incidence of severe and life-threatening infections; rescue bone marrow graft failure or speed graft recovery in patients undergoing autologous bone marrow transplantation | Acute myelogenous leukemia, mobilization and engraftment of peripheral blood progenitor cells |
| Biologics | HER2/neu receptor antagonist | Trastuzumab (Herceptin ®) | recombinant humanized monoclonal antibody directed against the human epidermal growth factor receptor 2 (HER2). After binding to HER2 on the tumor cell surface, trastuzumab induces an antibody-dependent | Adenocarcinomas, breast cancer |

TABLE 6-continued

Examples of Biologics Useful for Treating Neoplastic Diseases

| Class | Type of Agent | Example | Proposed Mechanism of Action | Neoplasms/Disease |
|---|---|---|---|---|
| | | | cell-mediated cytotoxicity against tumor cells that overexpress HER2. HER2 is overexpressed by many adenocarcinomas, particularly breast adenocarcinomas. | |
| Biologics | Therapeutic peptide | Interferon α-2b (Intron ® A) | cytokines produced by nucleated cells (predominantly natural killer (NK) leukocytes) upon exposure to live or inactivated virus, double-stranded RNA or bacterial products. These agents bind to specific cell-surface receptors, resulting in the transcription and translation of genes containing an interferon-specific response element. The proteins so produced mediate many complex effects, including antiviral effects (viral protein synthesis); antiproliferative effects (cellular growth inhibition and alteration of cellular differentiation); anticancer effects (interference with oncogene expression); and immune-modulating effects (natural killer cell activation, alteration of cell surface antigen expression, and augmentation of lymphocyte and macrophage cytotoxicity) | Hairy cell leukemia, malignant melanoma, follicular lymphoma, condylomata acuminata, chronic hepatitis C and B, |
| Biologics | Therapeutic peptide | Interferon β-1b (Betaseron ®, Rebif ®) | chemically identical to or similar to endogenous interferon beta with antiviral and anti-tumor activities. Endogenous interferons beta are cytokines produced by nucleated cells (predominantly natural killer cells) upon exposure to live or inactivated virus, double-stranded RNA or bacterial products. These agents bind to specific cell-surface receptors, resulting in the transcription and translation of genes with an interferon-specific response element. The proteins so produced mediate many complex effects, including antiviral (the most important being inhibition of viral protein synthesis), | relapsing multiple sclerosis |

TABLE 6-continued

Examples of Biologics Useful for Treating Neoplastic Diseases

| Class | Type of Agent | Example | Proposed Mechanism of Action | Neoplasms/Disease |
| --- | --- | --- | --- | --- |
| Biologics | IL-2 product | Aldesleukin (Proleukin ®) | antiproliferative and immune modulating effects. Possesses the biological activities of human native IL-2 | Metastatic renal cell carcinoma, metastatic melanoma |
| Biologics | Monoclonal antibody | Alemtuzumab (Campath ®) | CD52-directed cytolytic antibody | B-cell chronic lymphocytic leukemia |

Examples of antineoplastic biologics include, but are not limited to, Filgrastim (Neupogen®), a recombinant granulocyte colony-stimulating factor (G-CSF); and Sargramostim (Leukine®), a recombinant granulocyte/macrophage colony-stimulating factor (GM-CSF).

The term "monoclonal antibodies" ("mAb") generally refers to identical monospecific immunoglobulin molecules derived from a laboratory procedure from a single cell clone that are capable of binding to an agonist. Fully human monoclonal antibodies have the amino acid sequence of an immunoglobulin of the human species. "Humanized" monoclonal antibodies are constructed from mouse monoclonal antibodies having the desired specificity, and often have complementarity determining regions of a mouse immunoglobulin while maintaining the framework and constant regions of a human antibody to prevent a human-antimouse neutralizing response.

Examples of antineoplastic monoclonal antibodies include, but are not limited to, Bevacizumab (Avastin®), a recombinant humanized monoclonal IgG1 antibody that binds to and inhibits the biologic activity of human vascular endothelial growth factor ("VEGF") in in vitro and in vivo assay systems, and Panitumumab (Vectibix®), a human monoclonal antibody produced in transgenic mice that attaches to the transmembrane epidermal growth factor (EGF) receptor.

5. Hormones and Related Agents

Several chemotherapeutic agents exert their therapeutic effect through interactions with hormones and related agents. Table 7 shows examples of several chemotherapeutic agents classified as hormone and related agents.

TABLE 7

Examples of Hormones and Antagonists Useful for Treating Neoplastic Diseases

| Class | Type of Agent | Example | Proposed Mechanism of Action | Neoplasms/Disease |
| --- | --- | --- | --- | --- |
| Hormones and Antagonists | Progestin | Megestrol Acetate (Megace ES ®) | Mimicking the action of progesterone, megestrol binds to and activates nuclear progesterone receptors (PRs) in the reproductive system and pituitary; ligand-receptor complexes are translocated to the nucleus where they bind to progesterone response elements (PREs) located on target genes. Megestrol's antineoplastic activity against estrogen-responsive tumors may be due, in part, to the suppression of pituitary gonadotropin production and the resultant decrease in ovarian estrogen secretion; interference with the estrogen receptor complex in its interaction with genes and; as part of the progesterone receptor complex, direct interaction with the genome and downregulation of specific estrogen-responsive genes. This agent may also directly kill tumor cells | Endometrium, breast cancer; anorexia, cachexia (wasting), or other unexplained weight loss |

TABLE 7-continued

Examples of Hormones and Antagonists Useful for Treating Neoplastic Diseases

| Class | Type of Agent | Example | Proposed Mechanism of Action | Neoplasms/Disease |
|---|---|---|---|---|
| Hormones and Antagonists | Antiestrogen | Tamoxifen Citrate (Nolvadex ®) | When bound to the ER, tamoxifen induces a change in the three-dimensional shape of the receptor, inhibiting its binding to the estrogen-responsive element ("ERE") on DNA. Under normal physiological conditions, estrogen stimulation increases tumor cell production of transforming growth factor β ("TGF-β"), an autocrine inhibitor of tumor cell growth. "Autocrine signaling" refers to a form of signaling in which a cell secretes a hormone or chemical messenger (autocrine agent) that binds to autocrine receptors on the same cell type, leading to changes in the cells. By blocking these pathways, the net effect of tamoxifen treatment is to decrease the autocrine stimulation of breast cancer growth. | breast cancer, especially postmenopausal women with estrogen-receptor positive (ER+) metastatic breast cancer or following primary tumor therapy in the adjuvant setting; premenopausal women with ER+ tumors. |
| Hormones and Antagonists | Androgen | Fluoxymesterone (Halotestin ®) | binds to and activates specific nuclear receptors, resulting in an increase in protein anabolism, a decrease in amino acid catabolism, and retention of nitrogen, potassium, and phosphorus. This agent also may competitively inhibit prolactin receptors and estrogen receptors, thereby inhibiting the growth of hormone-dependent tumor lines | Breast cancer; testosterone replacement therapy in males with primary hypogonadism or hypogonadotrophic hypogonadism, as well as palliation of androgen-responsive recurrent mammary cancer in females |
| Hormones and Antagonists | Gonadotropin-releasing Hormone Analog | Leuprolide (leuprolide acetate, Eligard ®) | binds to and activates gonadotropin-releasing hormone (GnRH) receptors. Continuous, prolonged administration of leuprolide in males results in pituitary GnRH receptor desensitization and inhibition of pituitary secretion of follicle stimulating hormone (FSH) and luteinizing hormone (LH), leading to a significant decline in testosterone production; in females, prolonged administration results in a decrease in estradiol production. This agent reduces testosterone production to castration levels and may inhibit androgen receptor-positive tumor progression | Prostate cancer; endometriosis, anemia secondary to uterine leiomyomas and central precocious puberty |

TABLE 7-continued

Examples of Hormones and Antagonists Useful for Treating Neoplastic Diseases

| Class | Type of Agent | Example | Proposed Mechanism of Action | Neoplasms/Disease |
|---|---|---|---|---|
| Hormones and Antagonists | Somatostatin Analog | Octreotide acetate (Sandostatine LAR Depot ®) | suppresses the luteinizing hormone response to gonadotropin-releasing hormone, decreases splanchnic blood flow, and inhibits the release of serotonin, gastrin, vasoactive intestinal peptide (VIP), secretin, motilin, pancreatic polypeptide, and thyroid stimulating hormone | Acromegaly, severe diarrhea/flushing episodes associated with metastatic carcinoid tumors, diarrhea associated with VIP-secreting tumors |

5.1. Antiestrogens

Antiestrogens are modulators of the estrogen receptor. Estrogens are the family of hormones that promote the development and maintenance of female sex characteristics. Examples of antiestrogens include, but are not limited to, tamoxifen citrate (Nolvadex®), a competitive inhibitor of estradiol binding to the estrogen receptor ("ER").

5.2. Gonadotropin-Releasing Hormone Analogs

Gonadotropin-releasing hormone ("GnRH") analogs are synthetic peptide drugs modeled after human GnRH. They are designed to interact with GnRH receptor. The analogs of GnRH peptide include leuprolide (Lupron®, Eligard®), goserelin (Zoladex®), triptorelin (Trelstar Depot®) and buserelin (Suprefact®). These compounds have biphasic effects on the pituitary. Initially, they stimulate the secretion of both follicle-stimulating hormone ("FSH") and luteinizing hormone ("LH"). However, with longer-term administration, cells become desensitized to the action of GnRH analogs. As a result, there is inhibition of the secretion of LH and FSH and the concentration of testosterone falls to castration levels in men and estrogen levels fall to postmenopausal values in women.

GnRH analogs have been used to treat prostatic carcinomas. They present several side-effects, including a transient "flare" of disease. Notwithstanding, leuprolide and goserelin have been used for the treatment of metastatic breast cancer. GnRH analogs also have been used in the treatment of endometriosis, anemia secondary to uterine leiomyomas and central precocious puberty. Examples of gonadotropin-releasing hormone analogs include Leuprolide acetate, the salt of a synthetic nonapeptide analog of gonadotropin-releasing hormone.

5.3. Androgens and Antiandrogens

The term "androgen" as used herein refers to any natural or synthetic compound that promotes male characteristics. Examples of antineoplastic androgens include, but are not limited to, fluoxymesterone (Halotestin®), a halogenated derivative of 17-alpha-methyltestosterone.

Antiandrogens are competitive inhibitors that prevent the natural ligands of the androgen receptor from binding to the receptor. These compounds have activity of their own against prostate cancer. They also are effective in preventing the flare reaction induced by the testosterone surge that can occur with GnRH chemotherapy. The antiandrogens may be divided structurally and mechanistically into (1) steroidal and (2) nonsteroidal antiandrogens ("NSAAs"). The steroidal agents have some partial agonist activity at the androgen receptor. These include such compounds as cyproterone acetate (Androcur®) and megestrol acetate ("Megace®). Side-effects include loss of libido, decreased sexual potency, and low testosterone levels. The NSAAs inhibit the translocation of the androgen receptor to the nucleus from the cytoplasm of target cells, thus providing an antiproliferative effect. NSAAs include flutamide (Eulexin®), nilutamide (Nilandron®), and bicalutamide (Casodex®).

Additional antiandrogen agents, include, but are not limited to, megestrol acetate, the salt of megestrol, a synthetic derivative of the naturally occurring female sex hormone progesterone, with progestogenic, antiestrogenic, and antineoplastic activities.

5.4. Somatostatin Analog

Examples of somatostatin analogs include, but are not limited to, octreolide acetate (Sandostatin LAR® Depot), the salt of a synthetic long-acting cyclic octapeptide with pharmacologic properties mimicking those of the natural hormone somatostatin.

6. Miscellaneous Agents

Imatinib mesylate (Gleevec®) inhibits the function of bcr-abl, a constituitively active tyrosine kinase. See, e.g., Kerkelä, R., et al., Nat. Med. 12: 908-16 (2006). Table 8 shows examples of other miscellaneous chemotherapeutic agents for treating neoplastic disease.

TABLE 8

Examples of Miscellaneous Agents Useful for Treating Neoplastic Diseases

| Class | Type of Agent | Example | Proposed Mechanism of Action | Neoplasms/Disease |
|---|---|---|---|---|
| Miscellaneous Agent | Kinase inhibitor | Sorafenib (Nexavar ®) | blocks the enzyme RAF kinase, a critical component of the RAF/MEK/ERK-β signaling cascade, thereby blocking tumor angiogenesis | Hepatocellular carcinoma, advanced renal cell carcinoma |

TABLE 8-continued

Examples of Miscellaneous Agents Useful for Treating Neoplastic Diseases

| Class | Type of Agent | Example | Proposed Mechanism of Action | Neoplasms/Disease |
|---|---|---|---|---|
| Miscellaenous Agents | Kinase inhibitor | Imatinib mesylate (Gleevec ®) | binds to an intracellular pocket located within tyrosine kinases (TK), thereby inhibiting ATP binding and preventing phosphorylation and the subsequent activation of growth receptors and their downstream signal transduction pathways. This agent inhibits TK encoded by the bcr-abl oncogene as well as receptor TKs encoded by the c-kit and platelet-derived growth factor receptor (PDGFR) oncogenes | myeloid leukemia, lymphoblastic leukemia, myelodysplastic - myeloproliferative diseases |
| Miscellaneous Agent | kinase inhibitor | Sunitinib malate (Sutent ®) | | Gastrointestinal stromal tumor, advanced renal cell carcinoma |
| Miscellaneous Agent | HER1/EGFR tyrosine kinase inhibitor | Erlotinib (Tarceva ®) | competes with ATP to reversibly bind to the intracellular catalytic domain of epidermal growth factor receptor (EGFR) tyrosine kinase, thereby reversibly inhibiting EGFR phosphorylation and blocking the signal transduction events and tumorigenic effects with EGFR activation | Non-small cell lung cancer, pancreatic cancer |
| Miscellaneous Agents | Platinum Coordination Complex | Cisplatin | forms highly reactive, charged, platinum complexes which bind to nucleophilic groups such as GC-rich sites in DNA, inducing intrastrand and interstrand DNA cross-links, as well as DNA-protein cross-links. These cross-links result in apoptosis and cell growth inhibition | ovarian cancer, non-small cell lung cancer, and small cell lung cancer; cancer of bladder, head and neck, and endometrium |
| Miscellaneous Agents | Platinum Coordination Complex | Carboplatin | when activated intracellularly forms reactive platinum complexes that bind to nucleophilic groups such as GC-rich sites in DNA, thereby inducing intrastrand and interstrand DNA cross-links, as well as DNA-protein cross-links. These carboplatin-induced DNA and protein effects result in apoptosis and cell growth inhibition | ovarian cancer, non-small cell lung cancer, and small cell lung cancer |
| Miscellaneous Agents | Platinum Coordination Complex | Oxaliplatin (Eloxatin ®) | alkylates macromolecules, forming both inter- and intra-strand platinum-DNA crosslinks, which result in inhibition of DNA replication and transcription and cell-cycle nonspecific cytotoxicity | Advanced metastatic carcinoma of colon or rectum; colon cancer |

TABLE 8-continued

Examples of Miscellaneous Agents Useful for Treating Neoplastic Diseases

| Class | Type of Agent | Example | Proposed Mechanism of Action | Neoplasms/Disease |
|---|---|---|---|---|
| Miscellaneous Agents | Synthetic polypeptides | Glatiramer acetate (Copaxone ®) | Unknown | Multiple sclerosis |
| Miscellaneous Agents | Platelet-reducing Agent | Anagrelide (Agrylin ®, anagrelide hydrochloride) | Putatively provides dose-related reduction in platelet production resulting from a decrease in megakaryocyte hypermaturation | Thrombocythemia, polycythemia, chronic myelogenous leukemia, other myeloproliferative disorders including myeloid metaplasia with myelofibrosis |
| Miscellaneous Agents | Retinoids | Isotretinoin (Accutane ®) | binds to and activates nuclear retinoic acid receptors (RARs); activated RARs serve as transcription factors that promote cell differentiation and apoptosis | Severe recalcitrant nodular acne |
| Miscellaneous Agents | Retinoids | Tretinoin (Vesanoid ®) | induces maturation of acute promyelocytic leukemia | Acute promyelocytic leukemia |
| Miscellaneous Agents | Retinoids | Bexarotene (Targretin ®) | selectively binds to and activates retinoid X receptors (RXRs), thereby inducing changes in gene expression that lead to cell differentiation, decreased cell proliferation, apoptosis of some cancer cell types, and tumor regression | Cutaneous manifestations of T-cell lymphoma |
| Miscellaneous Agents | Sympathoimetic amine | Methylphenidate (Daytrana ®; Ritalin ®, Methylin ®, Metadate CD ®, Concerta ®) | activates the brain stem arousal system and cortex to produce its stimulant effect and, in some clinical settings, may improve cognitive function. | Attention deficit hyperactivity disorder; narcolepsy |
| Miscellaneous Agents | Sympathoimetic amine | Dexmethylphenidate HCl (Focalin ®) | activates the brain stem arousal system and cortex to produce its stimulant effect and, in some clinical settings, may improve cognitive function. | Attention deficit hyperactivity disorder |
| Miscellaneous Agents | Sympathoimetic amine | Dextroamphetamine sulfate (Dexedrine ®) | elevates blood pressure and cause bronchodilation | Attention deficit hyperactivity disorder; narcolepsy |
| Miscellaneous Agents | Synthetic analog | Paricalcitol (Zemplar ®) | synthetic noncalcemic, nonphosphatemic vitamin D analogue that binds to the vitamin D receptor and has been shown to reduce parathyroid hormone (PTH) levels | secondary hyperparathyroidism associated with chronic kidney disease |
| Miscellaneous Agents | Class I antiarrhythmic | Disopyramide phosphate (Norpace ®) | decreases rate of diastolic depolarization in cells with augmented automaticity, decreases upstroke velocity, and increases action of potential duration of normal cardiac cells | Life-threatening ventricular arrhythmias |
| Miscellaneous Agents | ACE inhibitor/calcium channel blocker (nondihydropyridine) | Trandolapril-verapamil HCl (Tarka ®) | ACE inhibitor, calcium channel blocker | Hypertension |
| Miscellaenous Agents | Opioid analgesic | Methadone HCl (Dolophine ®) | Opioid analgesic; μ-agonist; also acts as an antagonist at the N-methyl-D-aspartate (NMDA) receptor | detoxifiction and temporary maintenance treatment of narcotic addiction; relief of severe pain |

TABLE 8-continued

Examples of Miscellaneous Agents Useful for Treating Neoplastic Diseases

| Class | Type of Agent | Example | Proposed Mechanism of Action | Neoplasms/Disease |
|---|---|---|---|---|
| Miscellaneous Agents | 5-hydroxy-tryptamine$_1$ receptor agonist | Sumatriptan Succinate (Imitrex ®) | selective agonist for a vascular 5-hydrotryptamine$_1$ receptor subtype | migraine, cluster headache |
| Miscellaneous Agents | Immune response modifying agent | Imiquimod (Aldara ®) | stimulates cytokine production, especially interferon production, and exhibits antitumor activity, particularly against cutaneous cancers. | actinic keratosis, superficial basal cell carcinoma, external genital warts |
| Miscellaneous Agents | serotonin reuptake inhibitor | Fluvoxamine maleate (Luvox ®) | serotonin reuptake inhibition | obsessive compulsive disorder, social anxiety disorder |
| Miscellaneous Agents | Norepinephrine (noradrenaline) reuptake inhibitor | Atomoxetine HCl (Strattera ®) | Unknown | Attention-deficit/hyperactivity disorder |

6.1. Kinase Inhibitors

Antineoplastic kinase inhibitors include, but are not limited to, Sorafenib tosylate (Nexavar®), a synthetic compound that targets growth signaling and angiogenesis, and Erlotinib hydrochloride (Tarceva®), the salt of a quinazoline derivative with antineoplastic properties.

6.2. Platinum Coordination Complexes

Examples of antineoplastic agents that form platinum coordination complexes include, but are not limited to, Cisplatin (cis-diamminedichloroplatinum (II), Platinol-AQ®), a divalent inorganic water-soluble, platinum containing complex that appears to enter cells by diffusion and reacts with nucleic acids and proteins, is a component of several combination chemotherapy regimens. For example, it is used with bleomycin, etoposide and vinblastine for treating patients with advanced testicular cancer, and with paclitaxel, cyclophosphamide or doxorubicin for treating ovarian cancer.

Another antineoplastic agent that forms a platinum coordination complex is Carboplatin (CBDCA, JM-8), which has a mechanism and spectrum of clinical activity similar to cisplatin, but generally is less reactive than cisplatin.

An additional antineoplastic agent is Oxaliplatin (trans-1-diaminocyclohexane oxalatoplatinum), which, like cisplatin, has a wide range of antitumor activity and is active in ovarian cancer, germ-cell cancer and cervical cancer. Unlike cisplatin, oxaliplatin in combination with 5-fluorouracil is active in colorectal cancer.

6.3. EDTA Derivatives

Other antineoplastic agents include EDTA-derivatives. Such compounds include, but are not limited to, Dexrazoxane hydrochloride (Zincard®), the salt of a bisdioxopiperazine with iron-chelating, chemoprotective, cardioprotective, and antineoplastic activities.

6.4. Platelet-Reducing Agent

Anagrelide hydrochloride (Agrlyin®) is a platelet-reducing agent used to treat thrombocythemia, secondary to myeloproliferative disorders, to reduce the elevated platelet count and the risk of thrombosis and to ameliorate associated symptoms including thrombo-hemorrhagic events.

6.5. Retinoids

Retinoids are a group of substances related to vitamin A and function like vitamin A in the body. Retinoids include, but are not limited to, bexarotene (Targretin®), a synthetic retinoic acid agent with potential antineoplastic, chemopreventive, teratogenic and embryotoxic properties; and isotretinoin (Accutane®), a naturally-occurring retinoic acid with potential antineoplastic activity.

6.6. Histone Deacetylase Inhibitors

The histone deacetylase inhibitor vorinostat (Zolinza®) is a synthetic hydroxamic acid derivative with antineoplastic activity, and a second generation polar-planar compound that binds to the catalytic domain of the histone deacetylases (HDACs). This allows the hydroxamic moiety to chelate zinc ion located in the catalytic pockets of the HDAC, thereby inhibiting deacetylation and leading to an accumulation of both hyperacetylated histones and transcription factors. Hyperacetylation of histone proteins results in the upregulation of the cyclin-dependant kinase p21, followed by $G_1$ arrest. Hyperacetylation of non-histone proteins such as tumor suppressor p53, alpha tubulin, and heat-shock protein 90 produces additional anti-proliferative effects. Vorinostat also induces apoptosis and sensitizes tumor cells to cell death processes.

7. Chemotherapeutic Drugs Useful for Treating Multiple Myeloma (MM)

7.1 Immunomodulatory Drugs

Immunomodulatory drugs effective in treating MM, include, but are not limited to, Thalidomide, and its synthesized analog Lenalidomide. Thalidomide/Lenalidomide are oral agents shown to be effective across the spectrum of myeloma disease (Rajkumar S V, Mayo Clin Proc. 2004; 79: 899-903; Kyle R A et al., Blood. 2008; 111: 2962-2972). The mechanism of action of both Thalidomide and Lenalidomide in MM is not fully understood. Proposed mechanism(s) include the inhibition of tumor necrosis factor-alpha (TNF alpha), prevention of free-radical-mediated DNA damage, suppression of angiogenesis, increase in cell-mediated cytotoxic effects, and alteration of the expression of cellular adhesion molecules, inhibition of the activity of nuclear factor kappa B (NF-kappa B) and the enzymes cyclooxygenase-1 and cyclooxygenase-2, and promotion of the cytotoxic activity of natural killer and T cells by stimulating their proliferation and secretion of interleukin 2 and interferon gamma.

7.2 Proteasome Inhibitors

Proteasome inhibitors effective in treating MM, include, but are not limited to, Bortezomib. Bortezomib, a first-in-class proteasome inhibitor, targets the 26S proteasome, a multicatalytic proteinase complex involved in intracellular protein degradation. Bortezomib inhibits transcription factor NF-kappaB activation by protecting its inhibitor I kappa B (IkappaB) from degradation by the 26S proteasome. Degradation of I kappa B by proteasome activates NF-kappaB, which up-regulates transcription of proteins that promote cell survival and growth, decreases apoptosis susceptibility, influences the expression of adhesion molecules, and induces drug resistance in myeloma cells (Merchionne F et al., Clin Exp Med. 2007; 7: 83-97). Bortezomib not only targets the myeloma cell, but also acts in the bone marrow microenvironment by inhibiting the binding of myeloma cells to bone marrow stromal cells and bone marrow-triggered angiogenesis.

7.3 Bisphosphonates

Bisphosphonates effective in treating MM, include, but are not limited to, Pamidronate and zoledronic acid. Bisphosphonates inhibit the dissolution of the hydroxyapatite crystals and down-regulate osteoclast function (Schwartz R N et al., JMCP, September 2008, Vol. 14, No. 7, pp. S12-S18). Certain bisphosphonates (the more potent nitrogen-containing compounds) also appear to have antitumor activity and have been shown to reduce production of the growth factor interleukin 6 (IL-6), which plays a role in the growth and survival of myeloma cells (Schwartz R N et al., JMCP, September 2008, Vol. 14, No. 7, pp. S12-S18). Pamidronate also stimulates an immune response against MM that is mediated by T cells (Schwartz R N et al., JMCP, September 2008, Vol. 14, No. 7, pp. S12-S18). Pamidronate and zoledronic acid have been shown to induce apoptosis (programmed cell death) in the laboratory (Multiple Myeloma Research Foundation. Bisphosphonate overview, www.multiplemyeloma.org/treatment/3.06.php).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The Microfluidic System

The value of 3D in vitro culture for developing tissues that reproduce authentic cell functions and physiology in comparison to conventional 2D culture has been demonstrated (Bell E., Nature Reviews Immunology 2006; 6:87). The ability to control the architecture and dynamics of 3D tissue microenvironments also provides opportunities to maintain certain cells and their functions which have been previously difficult to reproduce in vitro.

Sealable microfluidic devices useful in the described invention include the devices described in U.S. patent application Ser. No. 13/690,831, the contents of which are incorporated by reference herein.

According to one embodiment, the described invention provides a platform of interconnected 3D microfluidic tissue culture devices having tissue culture chambers. An exemplary platform arranged according to certain embodiments of the described invention comprises a plurality of such devices. Each device includes at least one tissue culture chamber in which cells may be cultured to form three-dimensional tissues. Each chamber has an inlet and an outlet. Capillary tubing is connected to the inlet and outlet to provide a flow of culture medium or other fluids through the chamber. According to another embodiment, a microscope or other imaging device may be provided to obtain images ("imaging") of the chambers.

According to one embodiment, liquids are pumped through the devices at flow rates and volumes designed to represent the fraction of cardiac output (i.e., total medium flow rate) and residence time (i.e., volume/flow) present under normal homeostatic physiological conditions, including the integration of the cardiovascular and lymphatic systems in a physiologically correct manner. The desired flow rates may be provided by the use of microfluidic pumps.

According to one embodiment, 8 polydimethylsiloxane (PDMS) culture chambers are assembled onto a single glass slide by photolithography. PDMS and glass are used as primary construction materials with their proven biocompatibility and wide use in biomedical research. PDMS has also other numerous salient features including elastomeric properties, $O_2$ and $CO_2$ permeability desired for long-term cell culture inside a conventional incubator, high chemical inertness, and optical transparency with low-auto fluorescence. Glass is used as the bottom substrate for imaging access by an inverted microscope.

According to another embodiment, the described invention provides a microfluidic device comprising a surface into which microchannels are fabricated such as those disclosed by U.S. patent application Ser. No. 11/637,912 and U.S. Pat. No. 6,048,498, which are hereby incorporated by reference in their entireties. For example, the microfluidic device can be made of any material such as glass, a co-polymer or a polymer. Co-polymers and polymers include, but are not limited to, urethanes, rubber, molded plastic polymethylmethacrylate (PMMA), polycarbonate, polytetrafluoroethylene (TEFLON™), polyvinylchloride (PVC), polydimethylsiloxane (PDMS), polysulfone, and the like. The materials are selected for their ease of manufacture, low cost and disposability, and general inertness to most extreme reaction conditions. Such devices are readily manufactured, for example, from fabricated masters, using well known molding techniques, such as injection molding, embossing or stamping, or by polymerizing a polymeric precursor material within the mold or by soft lithography techniques known in the art. (See Love, et al., MRS Bulletin, pp. 523-527 (July 2001) "Fabrication of Three-Dimensional Microfluidic Systems by Soft Lithography," Delamarche et al, Journal of American Chemical Society, Vol. 120, pp. 500-508 (1998), Delamarche et al, Science, Vol. 276, pp. 779-781 (May 1997), Quake et al., Science, Vol. 290, pp. 1536-1540 (Nov. 24, 2000), U.S. Pat. No. 6,090,251, all of which are hereby incorporated by reference).

A microfluidic device may be fabricated by other known techniques, e.g., photolithography, wet chemical etching, laser ablation, air abrasion techniques, injection molding, or embossing. When a microfluidic device is mated to a test chamber, channels flow a test compound containing liquid by either capillary action, positive pressure or vacuum force. The diameter of the channels of a microfluidic device should be large enough to prevent clogging of the channel. Further, channels may be coated with various agents to prevent nonspecific absorption of a test compound or its metabolites.

According to one embodiment, the device is as disclosed by U.S. Pat. No. 7,374,906, which is hereby incorporated by reference in its entirety. For example, the device may include a housing comprising a support member and a top member mounted to the support member by being placed in substantially fluid-tight, conformal contact with the support member, where "conformal contact" means a substantially form-fitting, substantially fluid-tight contact. The support member and the top member are configured such that they together define a discrete chamber. The device may comprise, for example, a plurality of discrete chambers. The discrete chamber includes, but is not limited to, a first well region including at least one first well and second well region including at least one second well, the second well region further being horizontally offset with respect to the first well region in a test orientation of the device. The "test orientation" of the device is meant to refer to a spatial orientation of the device during testing. The device may further include a channel region including at least one channel connecting the first well region and the second well region with one another. Each well region may include a single well, and the channel region may include a single channel. Each well may be defined by a through-hole in top and by an upper surface U. The chamber's first well may be adapted to receive a test agent that is a soluble test substance and/or an immobilized test biomolecule. Biomolecules include, but are not limited to, DNA, RNA, proteins, peptides, carbohydrates, cells, chemicals, biochemicals, and small molecules. The chamber's second well may be adapted to receive a biological sample of cells. Non-limiting examples of the test agent include chemorepellants, chemotactic inhibitors, and chemoattractants, such as growth factors, cytokines, chemokines, nutrients, small molecules, and peptides. Alternatively, the chamber's first well may be adapted to receive a biological sample of cells and the chamber's second well may be adapted to receive a test agent.

According to one embodiment, the device is as disclosed by U.S. Pat. No. 8,389,294, which is hereby incorporated by reference in its entirety. For example, the microfluidic device may include a first body and a second body formed from any suitable material including, but not limited to, polydimethylsiloxane (PDMS). The first and second bodies may be identical in structure. The first body and the second body may have a first and a second side and a first and a second end. The first body and the second body may further include upper and lower surfaces. A channel may extend through the first body and the second body of the microfluidic device and may include a first vertical portion terminating at an input port that communicates with an upper surface of first body and the second body and a second vertical portion terminating at an output port communicating with lower surface of first body and the second body. First and second vertical portions of the channel are interconnected by and communicate with a horizontal portion of the channel. The dimension of the channel connecting input port and output port may be arbitrary. The shape of the input ports and output ports of the microfluidic device may be, for example, circular, slit-shaped and oval configurations.

Example 2

Formation of 3D Bone-Like Tissues Using Mouse Calvarial Preosteoblast Cells (MC3T3-E1)

The following experiment shows that the dynamic ex vivo BM niche provides real time monitoring of cell response, high throughput, robust long-term culture; and use of small sample amounts.

Primary mouse preosteoblasts (osteoblasts) were cultured in an 8-chamber microfluidic device fabricated from polydimethylsiloxane and glasslide. $1 \times 10^3$ osteoblast cells were seeded for each 10 µL chamber. Dulbecco's modified eagle medium (DMEM) supplemented with 10% fetal bovine serum (FBS) and 1% penicillin/streptomycin was used at the flow rate of 0.8 µL/min for dynamic culture. After 3 weeks, the medium in 4 chambers was replaced with a conditioned medium sample of mouse MM cancer cells (5T33) cultured in DMEM ("MM medium"). The other 4 chambers were continued with DMEM as control. Optical microscopy was used to monitor cell and tissue morphology in real time. Cells were fixed and stained with Sytox® after 5 weeks for confocal microscopy examination.

Figure 2A:
FIG. 2*a* shows microfluidic chambers on a glass slide with real-time imaging of microfluidic bone construct with long term dynamic culture
Figure 2B:
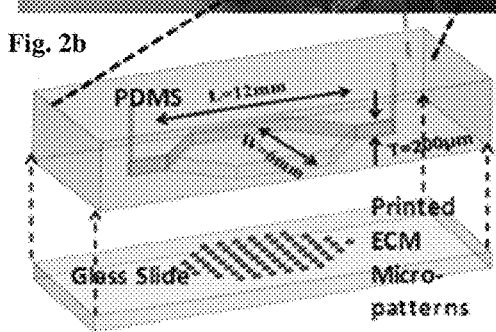
FIG. 2*b* shows a schematic representation of a microfluidic chamber.
Figure 2C:
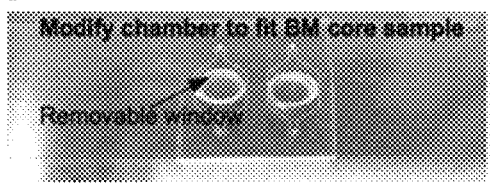
FIG. 2*c* shows a microfluidic chamber with removable window modified to fit a BM core sample.
Figure 2D:
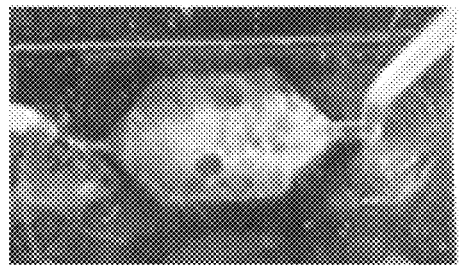
FIG. 2*d* shows a microfluidic chamber filled by a 3D tissue structure that has produced a perfusion environment.
Figure 2E:
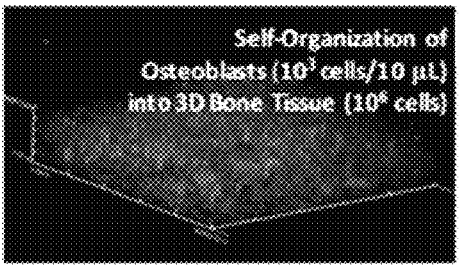
FIG. 2*e* shows self-organization of osteoblasts into 3D bone tissue.

Four channels of the first microfluidic device were (1) preconditioned with fibronectin; (2) seeded with osteoblasts, and (3) used for 12-day monoculture with the M-αMEM flow rate of 0.1 µL/min. After the cell seeding step, osteoblasts rapidly adhered and spread. Subsequently, the cells proliferated and formed a confluent layer on the bottom surface of the channels within 2 days (FIG. 2a). Upon reaching confluence, the cells gradually migrated to the side walls and top surface of the channels between day 3 and 4 (FIG. 2b). From this point on, the cells proliferated on both the top and bottom surfaces and formed multiple cell layers that grew into the channel volume (FIG. 2c). By day 7, the cells started to form 3D nodular structures throughout the entire length of the channels. The nodule in FIG. 2d appeared as a rope-like structure, connecting the cell layers grown from the bottom and top surfaces of the channels. Some nodular structures were more turbid and denser than others, and appeared to consist of more extracellular matrix deposited within the turbid and denser nodular structures. By day 8, these nodular structures were observed in most areas of the channels. The nodular structures underwent constant dynamic remodeling during the rest of the 12-day culture. When a nodule became sufficiently large and dense to block the medium flow through the channel, the nodule remodeled to allow channeling of the medium flow. The alizarin red staining at the end of the culture showed evidence of significant calcium deposition (FIG. 2e, day 12). The more turbid and denser nodules were stained darker.

FIG. 3 shows microscopic observations and schematic illustrations of the osteoblast developmental sequence under the microscale confines of the culture chambers shown in FIGS. 2a and 2b. FIG. 3a-d and left panel e show real-time imaging. Right panel e shows end-point imaging after alizarin red staining. The arrow depicted in e (right panel) indicates nodular structure with dense ECM.

The 3D tissue contracted to about one-tenth of its original size following removal from the culture chamber. Upon placing the contracted tissue in a Petri dish with the same culture medium, cells migrated out of the contracted structure within a few days.

These results indicate strong adhesion between 3D tissue and culture chamber surfaces as well as cohesion within the tissue. In contrast, when cells imbedded in collagen gels as reconstructed ECMs were cultured, significant contraction of the gels occurred within a week. It therefore was not possible to: 1) grow 3D tissues that uniformly fill up the chamber and 2) produce the perfusion microenvironment, an important biotransport feature of interstitial flow through tissues.

Advantages of this microfluidic Bone/BM culture approach include (1) long-term dynamic 3D cell expansion. with in-situ imaging and convenient endpoint for conventional cellular and biochemical characterization, without bubble formation or cross-contamination between chambers; (2) Easy-to-use, high-throughput, real-time imaging capabilities; (3) 200 μm chamber depth to emulate microvascular functions and interstitial flow space in which molecules (e.g., $O_2$, $CO_2$, nutrients, metabolic byproducts, drugs, etc.) are transported by perfusion. With at least one dimension in microscale, proliferating cells can migrate over short distances to form bone/BM 3D tissue structures while producing their own ECM by self-organization and perfusion conditions established throughout the chamber; and (4) the ability to vary the flow rate of the culture medium can allow mimicking of: (a) interstitial flow, (b) shear stresses exerted by the interstitial flow on cells, and (c) increased blood flow due to angiogenesis associated with tumor cell expansion.

Example 3

Reconstruction of BM Tumor Niche for the Survival and Proliferation of MM Tumor Cells Present in BM Biospecimens A 3D bone-like construct is made from OSB to recreate the tumor microenvironment and as the foundation for culturing BM biospecimens.

The microfluidic 3D tissue culture approach described in Example 2 will be optimize firstly using 5T33 myeloma cells (5T33MM) in the C57BL/KaLwRij mouse (Vanderkerken K, Asosingh K, Croucher P, Van Camp B., Immunol Rev 2003; 194:196-206; Vanderkerken K, Asosingh K, Willems A, et al., Methods Mol Med 2005; 113: 191-205; Menu E, Asosingh K, Van Riet I, Croucher P, Van Camp B, Vanderkerken K., Blood Cells Mol Dis 2004; 33:111-9). The 5T33MM tumor cell line originates from spontaneously developed MM in aged C57BL/KalwRij (B6Rij, H2b haplotype) mice and has since been propagated either in vitro or by intravenous injection into young naïve B6Rij recipients, which generates MM disease. The 5T33MM model has many of the characteristics associated with human MM, including homing and growth in the bone marrow compartment, hypercalcemia and elevated tumor-associated $IgG_2b_K$ in the circulation with diffuse osteolytic lesions (Vanderkerken K, Asosingh K, Croucher P, Van Camp B., Immunol Rev 2003; 194:196-206).

To further assess the advantages of this technology in comparison with standard cultures, a side by side comparison of this approach is run with a 3D-static culture according to Kirshner et al, Blood 112: 2935-45 (2008). In brief, mononuclear cells will be isolated from BM aspirates by Ficoll-Paque gradient centrifugation. Surface coating (rEnd) will be created by coating 48-well tissue culture plates (Corning, Corning, N.Y.) with fibronectin/collagen I (1:1) in phosphate-buffered saline (PBS) at a final concentration of 5 μg/l cm2 of each protein. Plates will be incubated for 30 minutes or more at room temperature; after removal of excess fluid, the rEnd will be overlaid with the rBM layer consisting of the BM mononuclear cells (BMCs) in an ECM mixture of Matrigel/fibronectin (2:1 vol/vol).

3.1 Preliminary Studies

Preliminary data show that the 3D bone construct provides a perfusion environment suitable for long-term dynamic culture of primary mouse BM explants.

BM specimens from 8-12 week old B6Rij mice were seeded into the 2-week old bone tissue grown from MC3T3-E1. Both adherent and non-adherent BM cells were retained within the perfusion environment of the 3D bone construct with some bone marrow cells differentiated into fat cells. In contrast, the BM cells were not retained in the empty culture chambers, even if 3D tissue constructs composed of hydroxyapatite nanoparticles, collagen gel, and/or poly(ε-caprolactone) nanofibers were introduced to the chambers. Also, in comparison to static 6-well plate culture, the proliferation and differentiation of the BM cells was more significant due to the 3D perfusion environment.

Methodology

Using Murine Samples

The running conditions of the microfluidic device will be optimized as summarized in Table 9 below. These conditions will be used as the starting point for the culture of patient BM biospecimens. To emulate angiogenesis and provide more cytokines and nutrients to the BM microenvironment, which may further sustain human MM cells, chamber flow rate and plasma concentration in the media will be adjusted. Different end points will also be assessed to determine how quickly the BM microenvironment can be reproduced.

TABLE 9

Microfluidic device running conditions

| Group | Variable | Setting |
|---|---|---|
| I | Duration | 7, 14 or 21 days after BM seeding |

TABLE 9-continued

Microfluidic device running conditions

| Group | Variable | Setting |
|---|---|---|
| II | Flow rate | 0.1, 0.5 and 1 µl per min |
| III | Plasma composition in the media | 10%, 20% or 30% |
| IV | Construct origin | OSB 3D matrix or patients derived BM cores (cores from patient samples are used in place of the OSB 3D tissue-like construct prior to seeking the patient's BM biospecimen |
| V | Biospecimen preservation | Frozen vs. fresh (collection of fresh BM samples will require IRB approval and patient consent) |
| VI | Control group | OSB cell line construct (no BM) & static 3D cultures per Kirsner, et al, Blood 112: 2935-45 (2008). Static 3D cultures are performed as described and used for side by side comparison with the microfluidic technology. |

Figure 4:
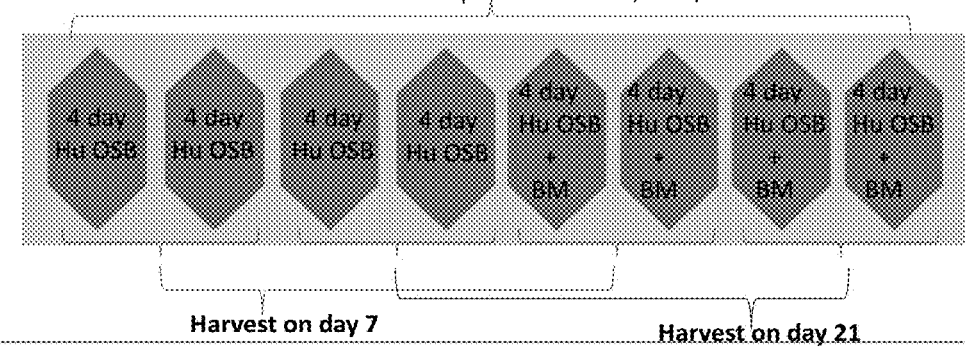
FIG. 4 shows a schematic representation of an experiment designed to study the effects of microenvironmental factors and to optimize culture conditions for ex vivo reconstruction of a BM microenvironment and the survival of the MM cancer cells.
Figure 5A:
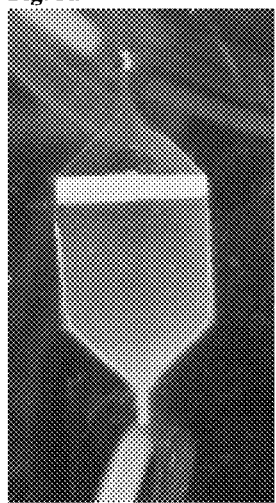
FIG. 5*a* shows patient bone marrow cells cultured in the 3D-bone like tissue for 21 days.
Figure 5B:
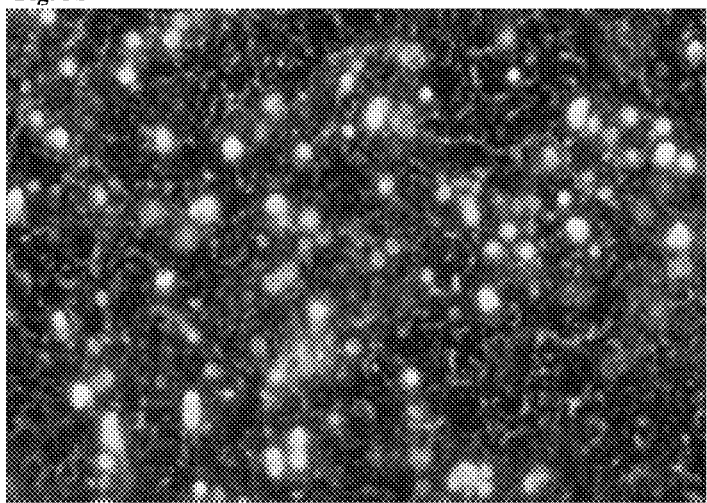
FIG. 5*b* shows a bright field and fluorescence merged image of CFSE labeled BM cells on the 3D-bone like tissue; cells in white are BM cells, cells in black are osteoblast cells.
Figure 5C:
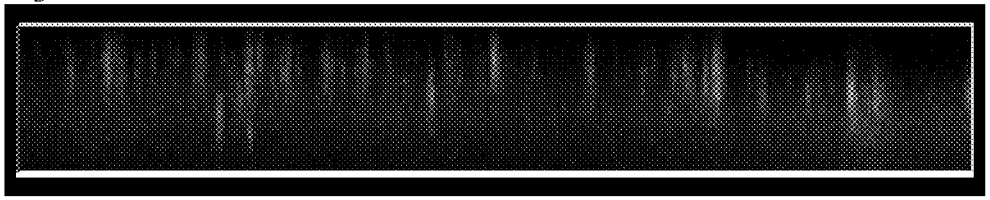
FIG. 5*c* shows a cross section of 21 day BM cells in the 3D-bone like tissue in rendered confocal image. The blurry white area represents ECM of the 3D tissue construct.

The following experimental setup will be followed to study the effects of these microenvironmental factors and to optimize the culture conditions for the ex vivo reconstruction of the BM microenvironment and the survival of the MM tumor. A device containing 8 microfluidic chambers comprised of the OSB 3D constructs or patient-derived BM cores will be plated with a patient's BM biospecimen(s) and perfused with the medium containing MM patient's plasma at a fluid flow rate of 0.1, 0.5 and 1 µl per min. An OSB cell line construct (no BM) and static 3D cultures are prepared as described as controls and used for side by side comparison with the microfluidic technology. At the termination of the experiments (e.g., 7, 14 or 21 days after BM seeding), 2 chambers will be used for in situ staining; two chambers will be used for immunohistochemistry, and the other four chambers will be harvested and pooled in twos, as depicted in FIG. 4, to get sufficient sample amounts for flow cytometric analysis. In a parallel setup, empty chambers (i.e., OSB construct alone) will be used as control.

Optimized conditions as determined using murine biospecimens will be used as the starting point for the human BM cultures. Sample collection (frozen vs. fresh or core biopsies) will be further compared to determine the best preservation method in order to ensure the survival of human MM cells.

Using Murine and Human Samples

Off-the-shelf OSB constructs for seeding BM biospecimens: The murine preosteoblast cell line MC3T3-E1 (ATCC#: CRL-2593) or the human OSB cell line hFOB1.19 will be cultured in the 8-chamber microfluidic device and used respectively to culture either murine or human BM. In brief, $1 \times 10^3$ cells will be seeded in each 10 µL chamber. DMEM supplemented with 10% fetal bovine serum (FBS), penicillin 100 U/mL and streptomycin 100 µg/mL will be used as a culture medium at a flow rate of 0.8 µL/min. Starting on Day 7, in order to create a mineralized structure, the cells will be subjected to an OSB differentiation medium which consists of growth medium plus 10 nM dexamethasone, 50 µg/mL ascorbic acid and 10 mM β-glycerophosphate.

In order to differentiate cell line OSB from those originated from murine or patient BM, the BM is labeled with carboxyfluorescein succinimidyl ester (CFSE) (Invitrogen (Life Technologies), Carlsbad, Calif., Catalog No. C34554 or equivalent) prior to plating. For example, cells at $5 \times 10^7$ cells/mL or less may be stained with 5-10 µmol CFSE in PBS/0.1% BSA for 10-15 minutes at 37° C. To quench the CFSE staining, an equal volume of culture media plus CFSE staining solution may be added to the cells and allowed to incubate for 5 minutes at 37° C. The CFSE-containing solution may be removed from the cells and the cells washed 3 times with an equal volume of culture media. Cells may be analyzed by microscopy or flow cytometry.

BM cell suspensions and core samples from 5T33MM tumor bearing B6Rij Mice: 8-12 week old recipient B6Rij mice will be injected with an intravenous (i.v.) dose of $0.5 \times 10^7$-$1 \times 10^7$ eGFP$^+$5 T33MM cells (kindly provided by Dr. Evren Alici, Karolinska Institute, HuddingeStockholm, Sweden). Expression of the enhanced Green Fluorescent Protein (eGFP) reporter will facilitate tracking and detection of these tumor cells. Upon manifestation of disease (development of paraplegia; i.e., hind limb paralysis) (Alici E, Konstantinidis K V, Aints A, Dilber M S, Abedi-Valugerdi M., Exp Hematol 2004; 32:1064-72), mice will be euthanized and BM cells will be isolated as described by Zilberberg J, Friedman T M, Dranoff G, Korngold R., Biol Blood Marrow Transplant 2010.

Based on preliminary experiments, i.v. inoculation of $0.5 \times 10^7$-$1 \times 10^7$ eGFP+5T33MM cells translates into at least 10% MM cells in the bone marrow of diseased mice, which recapitulates the percentage of tumor cells found in early stage human disease. For some experiments, BM cores will be used instead of the OSB constructs. Cores will be obtained by cutting up into small pieces the femurs of tumor bearing B6Rij mice. Cores will be placed in a modify microfluidic device that has a large removable window on the top PDMS section of the chamber, making it suitable for inserting macroscopic tissue pieces.

Using Human Samples

Patient BM and plasma biospecimens: Mononuclear cells from BM aspirates and plasma biospecimens from blood samples of newly diagnosed patients (13 in total, de-identified and with IRB approval) are isolated by Ficoll-Paque gradient centrifugation per the manufacturer's instructions. Cells are reconstituted in freezing media composed of 90% fetal bovine serum and 10% dimethyl sulfoxide (DMSO) at a concentration of $1 \times 10^7$-$1.5 \times 10^7$ cells/cryovial and stored in liquid nitrogen (usual collection=2-5 vials/patient). Plasma specimens are aliquoted (5-10 ml) and stored at −80° C. Since human MM cell viability can be adversely affected by BM cell preparation and storage conditions, for some of the proposed experiments fresh BM aspirates (and/or core biopsies, see below) and plasma samples from MM patients are collected. These studies will require further IRB approval and patient consent. When comparing biospecimen handling methods the impact of MM and stem cell (CD34$^+$) viability prior to microfluidic culture is assessed to ensure the most rapid MM expansion during culture while working with small quantities.

Patient BM core biopsy cultures: The ability of ex vivo cultured BM core biopsy explants to form a suitable environment for the preservation of MM cells will be compared to the OSB off-the-shelf matrix. For these experiments, further samples (fresh BM aspirates, plasma & BM core) from MM patients will be needed.

BM culture media: After seeding of the BM samples ($1 \times 10^4$-$1 \times 10^5$ cells/chamber) into the tissue-like OSB construct cultures or BM cores (kept at 37° C., in a 5% $CO_2$ incubator), the chambers will be perfused with BM growth medium (RPMI with L-glutamine, 10 to 30% MM patient plasma, $6.2\times10^{-4}$ M of $CaCl_2$, $1\times10^{-6}$ M sodium succinate, $1\times10^{-6}$ M hydrocortisone) 11 at a rate of 0.1 µL/min to ensure that BM biospecimens are able to make contact with the bone construct without getting flushed out of the chambers. Within 5-7 days post-seeding, flow rate can be varied (Table 9) to emulate the increased blood flow and mass transfer of the neovascularized BM. When using murine biospecimens fetal bovine serum (FBS) will be used in place of patient plasma.

Optimization of Microfluidic Device Running Conditions Using Murine Biospecimens FIG. 4 is a schematic representation of the experimental setup that will be followed to optimize the ex vivo reconstruction of the BM microenvironment. Microfluidic chambers will comprise the 3D constructs or BM cores, and will be plated with a BM biospecimen and perfused with the medium containing FBS or MM patient's plasma. At the termination of the experiments, to characterized the recreated BM microenvironment, 2 chambers will be used for in situ staining of adipocytes, OCL, and OSB as described in the analyses section, 2 chambers will be used for immunohistochemistry to identify cell populations and the other 4 chambers will be harvested and pooled in twos, as depicted in FIG. 4, to obtain sufficient sample amounts for flow cytometric analysis to quantify the percentage of reconstituted cells. In a parallel setup, empty chambers (i.e., OSB construct alone) will be used as control. Detailed explanations of these measurements can be found in the Analyses section below.

The optimized conditions, as determined using murine biospecimens, will be used as the starting point for the human BM cultures. Sample collection (frozen vs. fresh or core biopsies) will be further compared to determine the best preservation method in order to ensure the survival of human MM cells.

According to another embodiment, a 3D premade construct devised out of primary cells or a mix of osteoblasts/osteoclasts can be implemented, should co-cultures provide a more favorable foundation for the rapid reconstitution of the BM microenvironment. For example, multiple myeloma cells may be grown in RPMI 1640 medium (BioWhittaker) supplemented with 100 U/ml penicillin, 100 µg/ml streptomycin and 10% fetal bovine serum (FBS; GIBCO/BRL, Gaithersburg, Md.) and co-cultured with bone marrow stromal cells (e.g., HS-5 cells from ATCC, Manasas, Va., Catalog No. CRL-11882).

Criteria for Evaluation

For each condition, measurements of OCL, OSB, adipocytes, BM hematopoietic cells and tumor expansion as detailed in the Analyses section will be presented as mean (±standard deviation). Comparison between any two groups will be examined using t-test and comparison between more than two groups will be determine using analysis of variance (ANOVA) with Tukey multiple comparison procedure (MCP).

A test of normality such as the Shapiro-Wilk test will be conducted. If the data was found to be not normally distributed, measurements will be presented as median (interquartile range) and comparison of any two groups will be performed by Mann-Whitney test or Wilcoxon rank sum test and multiple comparisons comparison by Kruskal-Wallis test followed by pairwise-tests using Mann-Whitney test adjusted for multiple comparison. Statistical determination of sample sizes and significance between groups will be evaluated. Differences in the mean values with $P<0.05$ will be considered significant.

Definition of a Response

The following are quantitative milestones:

(1) that the described microfluidic technology can deliver an adequate means to sustain human MM cells using minimal amounts of BM biospecimens (anticipated to be $1\times10^4$ to $1\times10^5$ BM cell) and patient plasma (<2 mL/culture/week), for each chamber of the 8-chamber microfluidic device. This represents a potentially 10-100 fold reduction in the biospecimen amount required for personalized ex vivo culture from the state of the art. (ref. 11).

(2) that, upon optimization of the microfluidic culture approach, human MM cells can undergo from 2-fold to a 100 fold expansion in less than 21 days in culture. According to some embodiments the MM cells may undergo at least a 2-fold, at least a 4-fold, at least a 8-fold, at least a 16-fold, at least a 32-fold, at least a 64-fold, or at least a 100-fold expansion, i.e., from $1\times10^4$ cells to at least $2\times10^4$, at least $4\times10^4$, at least $8\times10^4$, at least $16\times10^4$, at least $32\times10^4$, at least $64\times10^4$, or at least $100\times10^4$ cells. Expansion to at least $1\times10^6$ MM cells will be required for biological characterization and drug efficacy testing.

Analyses

Characterization of the reconstructed BM microenvironment: To identify cells in the reconstructed BM, the cultures will be stained at different time points with tartrate-resistant acidic phosphatase [TRAP] (OCL), Oil Red (adipocytes), alkaline phosphatase or carboxyfluorescein succinimidyl ester (CFSE) (OSB) according to manufacturer's instructions and imaged using fluorescent microscopy. For example, for TRAP staining, medium may be removed from cells and cells washed with PBS. TRAP stain may be pre-warmed to 37° C. Cells may be fixed with 10% Glutaraldehyde for 15 minutes at 37° C. Next, cells may be washed with PBS pre-warmed to 37° C. Cells may be treated with 300 µl TRAP stain for 5-10 minutes at 37° C. TRAP stain may be removed and the cells washed with PBS. Finally, the cells may be observed under standard light microscopy. For example, for Oil Red staining, media may be removed from cells and the cells washed with PBS. Next, PBS may be removed and 10% formalin added to the cells for 30-60 minutes at room temperature. A stock solution of Oil Red may be prepared by weighing out 300 mg of Oil Red and adding to 100 ml of 99% isopropanol. Next, 3 parts Oil Red stock solution may be mixed with 2 parts DI water and incubated for 10 minutes at room temperature. Next, the 3:2 mixture may be filtered through a filter funnel. The formalin may be removed from the cells and the cells washed with DI water. 2 ml of 60% isopropanol may be added to the cells for 5 minutes at room temperature. Next, the isopropanol may be removed and the Oil Red mixture added to the cells for 5 minutes at room temperature. Oil red may be removed and the cells rinsed with tap water. 2 ml of hematoxylin stain may be added to the cells for 1 minute at room temperature. The hematoxylin may be removed and the cells rinsed with tap water. Cells may be may be observed under standard light microscopy. For example, for alkaline phosphatase staining, cell culture medium may be removed and the cells washed twice with 2 ml of PBST. The cells may be fixed in 10% formalin for 1-2 minutes at room temperature. Formalin may be removed and the cells washed with 2 ml of 1xPBST. PBST may be removed and alkaline phosphatase stain added the cells for 10-20 minutes at room temperature in the dark. Alkaline phosphatase may be removed and the cells washed twice with 2 ml of PBS.

To identify particular cell populations within the reconstructed bone/BM milieu, immunohistochemistry and flow cytometric analysis will be conducted as follows. For immunohistochemistry, paraffin blocks will be prepared by removing media from the culture and perfusing the matrix with 3% agar. Once solidified, the agar block will be removed and fixed in 10% neutral buffered formalin overnight before standard processing and staining. Murine samples will be examined for the presence of eGFP+ cells as the 5T33MM express this marker. Sections from human biospecimens will be stained for CD34 (hematopoietic stem cells), B220 or CD19 (murine and human B cells respectively), CD20 (activated B cells), CD138 (murine and human plasma cells/MM cells) (Bayer-Garner I B, Sanderson R D, Dhodapkar M V, Owens R B, Wilson C S., Mod Pathol 2001; 14:1052-8), and CD138+CD56+ (human MM cells) (Kirshner J, Thulien K J, Martin L D, et al., Blood 2008; 112:2935-45. expression using standard avidin-biotin-peroxidase methods). To determine the percentage change between the plated BM cells (Day 0) vs. cultured BM cells (7, 14 & 21 Days post-seeding), total cell counts and flow cytometric analysis will be conducted at each time point. At the conclusion of the experiments the cells will be harvested by trypsinization and stained and analyzed for the following markers using standard flow cytometric techniques: CD3 (murine and human T lymphocytes), CD34, CD19 or B220, CD20, CD138, and CD138CD56. Gating will be performed on the CD45$^{dim/-}$ cells (CD45 is expressed by differentiated hematopoietic cells).

Quantification of tumor proliferation: For analysis of proliferation and identification of non-proliferating cells, human BM cells will be labeled with 0.25 μM carboxyfluorescein diacetate, succinimidyl ester (CFSE; Invitrogen) as previously performed by Zilberberg, et al. (Zilberberg J F, S. L.; Friedman, T. M.; Korngold, R., ASBMT 2007; 13:106), prior to seeding in the microfluidic chambers. Proliferation will be measured by a decrease in CFSE fluorescence, 50% of which is lost with each cell division (Kirshner J, Thulien K J, Martin L D, et al. Blood 2008; 112:2935-45; Kirshner J, Thulien K J, Kriangkum J, Motz S, Belch A R, Pilarski L M. Leuk Lymphoma 2011; 52:285-9). After culturing, the percentage of harvested CFSE labeled cells (CFSE$^{high}$, CFSE$^{dim}$, CFSE$^{low}$) in each population (i.e., CD20$^+$, CD138$^+$, etc) will be compared to the percentage of labeled cells at the initiation of the culture. The CFSE$^{high}$ cells are most likely the cancer stem cells, because a defining property of stem cells is their proliferative quiescence. One of the diagnostic criteria for MM is to have at least 10% monoclonal plasma cells in the bone marrow (Durie B G, Kyle R A, Belch A, et al., Hematol J 2003; 4:379-98). Therefore, seeding of 10,000 BM cells will contain typically a minimum of 1,000 MM cells (per chamber or around $8 \times 10^3$ cells per device). The 3D perfused environment of our microfluidic device can allow for 1,000 fold expansion of cultured cells within 3 weeks of culture. Based on this observation and reported data on in vitro proliferation of MM cells (Kirshner J, Thulien K J, Martin L D, et al., Blood 2008; 112:2935-45, at least a 2-fold, at least a 4-fold, at least an 8-fold, at least 16-fold, at least 32-fold, at least 64-fold, or at least 100 fold increase in the tumor cell population (from $8 \times 10^3$ MM cells to at least $16 \times 10^3$, at least $3.2 \times 10^4$, at least $1.28 \times 10^5$, at least $5.12 \times 10^5$, or at least $8 \times 10^5$ MM cells by the end of the culture is anticipated.

Preliminary results are shown in Table 10; a direct comparison of 2D OSB+BM and 3D OSB+BM is summarized in Table 11 below.

TABLE 10

MM cell counting - viability and expansion

| Time | Culture medium | | 2D OSB | 2D OSB + BM | 3D OSB | 3D OSB + BM |
|---|---|---|---|---|---|---|
| Day -4 | 10% FBS | OSB number | $7.2 \times 10^4$ | $7.2 \times 10^4$ | $1.0 \times 10^4$ | $1.0 \times 10^4$ |
| Day 0 | 10% patient plasma | OSB number | $2.3 \times 10^5$ | $2.3 \times 10^5$ | $3.3 \times 10^4$ | $3.3 \times 10^4$ |
| Day 0 | 10% patient plasma | BM number | | $7.2 \times 10^4$ | | $1 \times 10^4$ |
| Day 0 | 10% patient plasma | MM number | | $2.9 \times 10^4$ | | $0.4 \times 10^4$ |
| Day 0 | 10% patient plasma | Total cell number | $2.3 \times 10^5$ | $3.2 \times 10^5$ | $3.3 \times 10^4$ | $4.3 \times 10^4$ |
| Day 7 | 10% patient plasma | Total cell number | $3.7 \times 10^4$ | $5.3 \times 10^4$ | $1.9 \times 10^4$ | $1.1 \times 10^5$ |
| Day 7 | 10% patient plasma | Corrected (CD138-CFSE) | 1.6% | 23.9% | 0% | 4.8% |
| Day 7 | 10% patient plasma | MM number | $1.2 \times 10^4$ | | | $0.41 \times 10^4$ |

As summarized in Table 11, below, the results show that when the results are compared at day 0 and day 7, the number of total cells in the three-dimensional tissue construct containing a dynamic ex vivo bone marrow (BM) niche is greater than in the 2D static culture. Moreover, the viability of MM cells in the three dimensional tissue construct containing a dynamic ex vivo bone marrow (BM) niche is superior to that in 2D static culture.

TABLE 11

| | 2D OSB + BM | 3D OSB + BM |
|---|---|---|
| Total cell number | 16.5% decrease | 256% increase |
| MM cell number | 41% viability | 102% viability |

Example 4

Patient MM Viability in 3D Microfluidic Bone Marrow Culture

Human osteoblasts (hFOB 1.19, ATCC CRL-11372) were cultured in the microfluidic device using Dulbecco's Modified Eagle Medium (DMEM), supplemented with 10% (v/v) fetal bovine serum, and 1% antibiotic solution at a flow rate of 0.8 μL/min. $4 \times 10^4$ osteoblasts/cm$^2$ (~$2 \times 10^4$ cells/chamber) were seeded and maintained at 37° C. in a humidified atmosphere of 5% CO$_2$ until a 3D ossified structure was formed.

BM specimens from three patients (Patients A, B and C) were seeded in two chambers each of the microfluidic device using RPMI culture medium supplemented with L-glutamine, 10% MM patient plasma, $6.2\times10^4$ M of $CaCl_2$, $1\times10^6$ M sodium succinate and $1\times10^6$ M hydrocortisone.

Flow cytometry was used to count MM cell number at day 7 and day 21. For analysis of proliferation and identification of non-proliferating cells, BM cells were labeled with 0.5 µM CFSE, prior to seeding in the microfluidic chambers. Proliferation was measured by a decrease in CFSE fluorescence, 50% of which is lost with each cell division. At the termination of the experiments (21 days post-BM seeding), cells were trypsinized and analyzed for CFSE expression in combination with other MM markers (i.e, CD138-PC5 and CD38-PC5/CD56-PE, CD138-PC5/CD38-PE) using standard flow cytometric techniques. Division peaks (as determined by CFSE-intensity) were labeled from 0 to n. For example, a single BM cell dividing n times will generate $2^n$ daughter cells. The total number of BM cells which have divided three times (n=3) is eight. Therefore, exactly one precursor BM cell had to divide three times to generate eight cells ($2^3$=8) (Wells A D et al., J. Clin. Invest., Vol. 100, No. 12, December 1997, pp. 3173-3183).

Figure 8A:
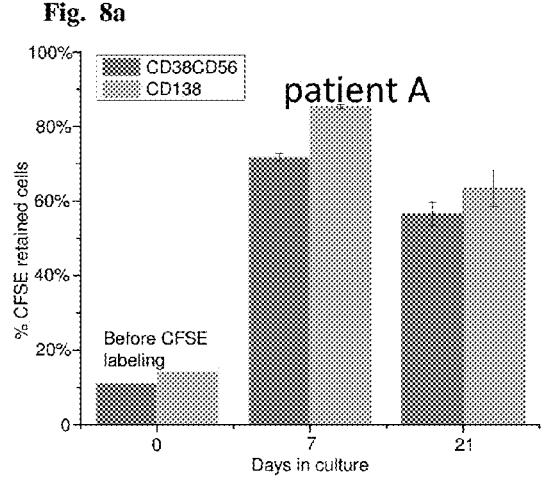
FIG. 8*a-c* show percent CFSE retained in BM cells from three patients (Patients A, B and C). MM percentage was tested on day 0, day 7 and day 21 respectively in CFSE labeled BM using markers CD138 and CD38/CD56.
Figure 8B:
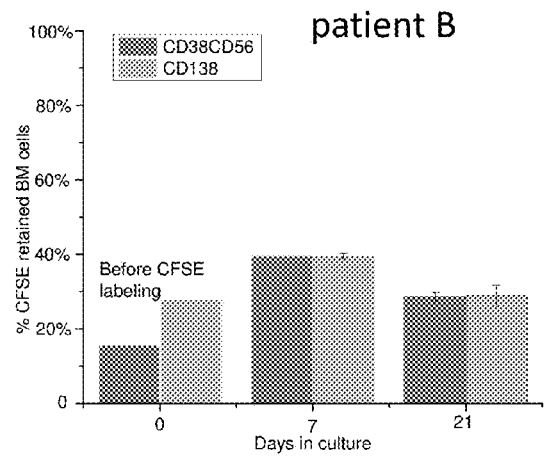
Figure 8C:
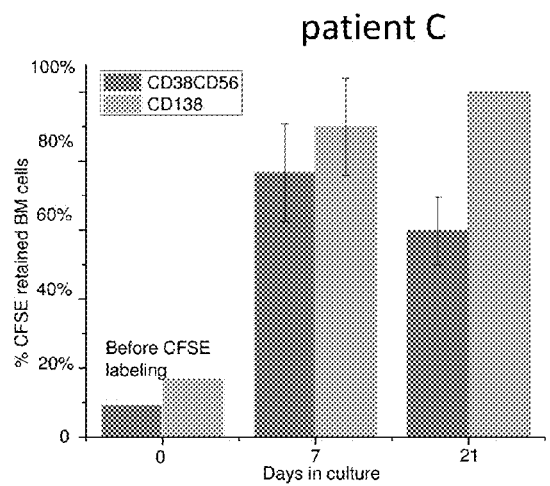

FIG. 8 shows the percent CFSE retained in patient BM cells. As expected, CD38+CD56+ and CD138+ (i.e., MM) cells on day 0 were not labeled by CFSE. For all three patients, both the CD38+CD56+ and the CD138+ cell populations showed an increased on day 7 as compared to day 0 due to non-adherent BM cells being washed away, which increases the percentage of MM cells in the BM. MM cells for all three patients were viable at 21 days. MM cells from patients A and C mostly retained CFSE on day 21. The percentage of MM cells from patient B was roughly 40% for CD38+CD56+CFSE+ and CD138+CFSE+ on day 7 and 30% for the corresponding staining on day 21. This may be due to rapid division of the MM cells so that the cells lost their CFSE staining.

Figure 9:
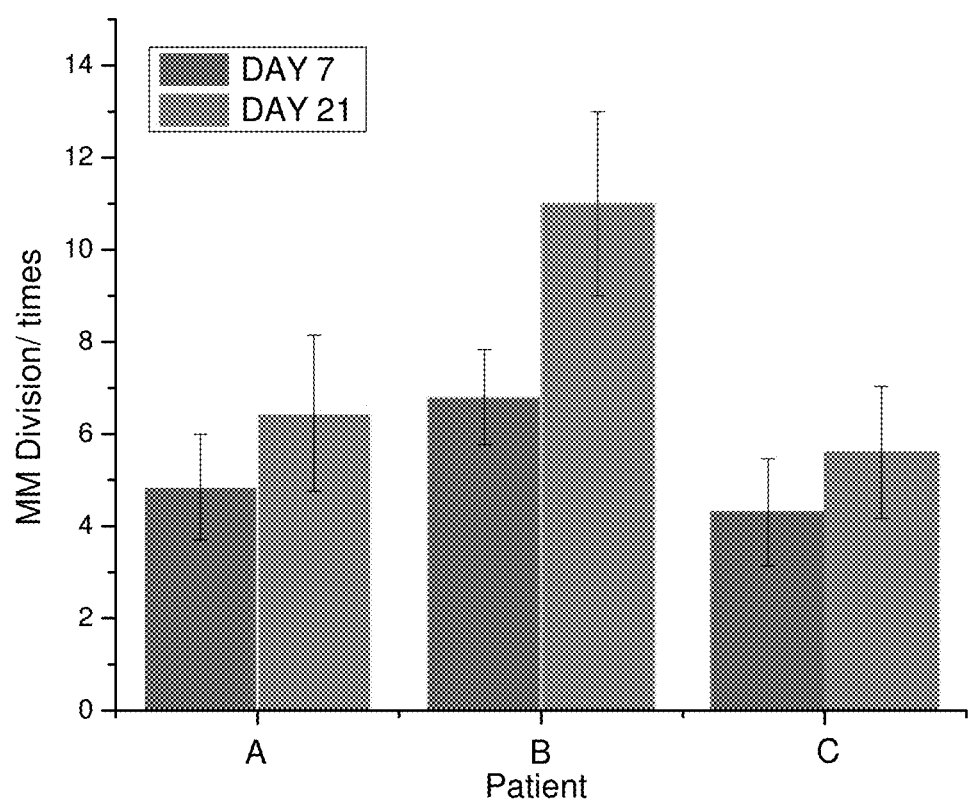
FIG. 9 shows the average BM expansion on day 7 and on day 21 for three patients (Patients A, B and C).

FIG. 9 shows MM division per times for all three patients on day 7 and day 21. BM cells for all patients were dividing. MM cells from patient B divided more than MM cells from patient A and MM cells from patient C.

* * *

Figure 10A:
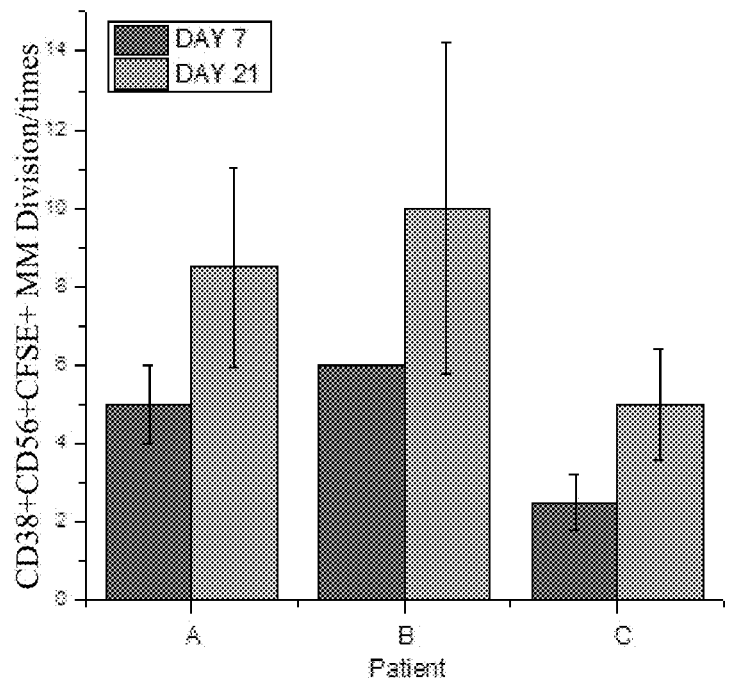
FIG. 10*a-b* show the average MM expansion on day 7 and day 21 respectively for three patients (Patients A, B and C). Each bar represents two different culture chambers for the same patient.
Figure 10B:
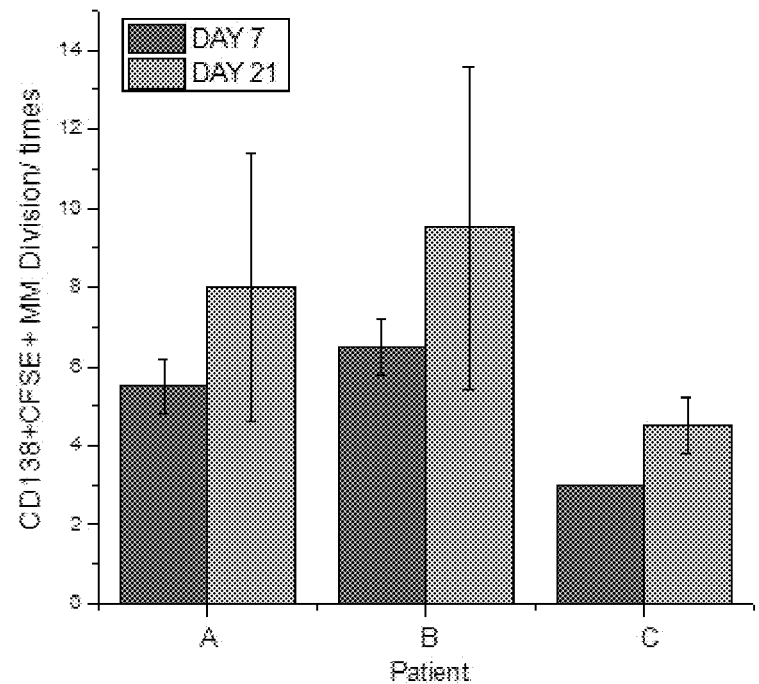

FIG. 10 shows CD138+CFSE+ and CD138+CFSE+ MM division for all three patients per times. MM cells from all three patients were dividing. MM cells from patient B divided more than MM cells from patient A and MM cells from patient C.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. An ex vivo multiple myeloma (MM) cancer niche contained in a device in which flow of minute amounts of liquids or dissolved gas molecules, is controlled by microfluidics (microfluidic device)comprising:
   (a) an ex vivo bone marrow microenvironment perfused by nutrients and dissolved gas molecules (bone marrow niche) comprising viable osteoblasts seeded on a surface of the microfluidic device and cultured to form 3D nodular structures that comprise a 3D bone-like tissue, the 3D bone-like tissue being characterized by an extracellular matrix secreted by the viable osteoblasts; and
   (b) a multiple myeloma tumor biospecimen comprising viable human multiple myeloma cells;
   the microfluidic device comprising
   (i) a culture chamber comprising a first well region including a first well and a second well region including a second well; each well defined by a through-hole in top and by an upper surface U; and
   (ii) a channel region comprising at least one channel originating at an input port and terminating at an output port comprising first and second vertical portions interconnected by and communicating with a horizontal portion of the channel, wherein the channel connects the first well region and the second well region with one another, wherein the first well is adapted to receive a test agent, the second well is adapted to receive a biological sample of cells, and liquids, nutrients and dissolved gas molecules flow through the channel;
   wherein the microfluidic device is effective to control flow of minute amounts of the liquids, nutrients and dissolved gas molecules in the MM cancer niche;
   wherein the ex vivo MM cancer niche is responsive to changing conditions of perfusion of the ex vivo MM cancer niche by the minute amounts of liquids, nutrients and dissolved gas molecules in the microfluidic device; and
   wherein formation of an ex vivo MM microenvironment in the microfluidic device is effective to recapitulate spatial and temporal characteristics of a multiple myeloma cancer niche in vivo and to maintain viability of the MM cells in the MM cancer niche in the microfluidic device ex vivo.

2. The ex vivo multiple myeloma (MM) cancer niche contained in a microfluidic device according to claim 1, wherein the biospecimen comprising human myeloma cells further comprises human plasma autologous to the human myeloma cells.

3. The ex vivo multiple myeloma (MM) cancer niche contained in a microfluidic device according to claim 1, wherein the microenvironment perfused by nutrients and dissolved gas molecules of the ex vivo bone marrow (BM) niche is effective for propagation of the human myeloma cells.

4. The ex vivo multiple myeloma (MM) cancer niche contained in a microfluidic device according to claim 1, wherein the MM niche further comprises osteoblast-secreted and MM cell-secreted soluble cytokines and growth factors.

5. The ex vivo multiple myeloma (MM) cancer niche according to claim 1, wherein the MM cells are adherent to osteoblasts of the BM niche.

6. The ex vivo multiple myeloma (MM) cancer niche according to claim 5, wherein the MM cells adhere to the osteoblasts of the BM niche by cell-cell interaction.

7. The ex vivo multiple myeloma (MM) cancer niche according to claim 1, wherein the human myeloma cells are cellular components of a bone marrow aspirate.

8. The ex vivo multiple myeloma (MM) cancer niche according to claim 1, wherein the human myeloma cells are cellular components of peripheral blood.

9. The ex vivo multiple myeloma (MM) cancer niche according to claim 1, wherein the human myeloma cells are cellular components of a core biopsy.

10. The ex vivo multiple myeloma (MM) cancer niche according to claim 1, wherein the ex vivo multiple myeloma (MM) cancer niche is effective for propagation of the human myeloma cells for at least 7 days.

11. The ex vivo multiple myeloma (MM) cancer niche according to claim 1, wherein the sample of human myeloma cells added to the BM niche constitutes $1\times10^4$ to $1\times10^5$ mononuclear cells.

12. The ex vivo MM cancer niche according to claim 1, wherein propagation of the MM cells is capable of producing deterioration of the 3D ossified tissue of the BM niche.

13. A method for preparing an ex vivo multiple myeloma (MM) cancer niche contained in a device in which flow of minute amounts of liquids or dissolved gas molecules is controlled by microfluidics (microfluidic device), the microfluidic device comprising
  (i) a culture chamber comprising a first well region including a first well and a second well region including a second well; each well defined by a through-hole in top and by an upper surface U; and
  (ii) a channel region comprising at least one channel originating at an input port and terminating at an output port comprising first and second vertical portions interconnected by and communicating with a horizontal portion of the channel, wherein the channel connects the first well region and the second well region with one another, wherein the first well is adapted to receive a test agent, the second well is adapted to receive a biological sample of cells, and liquids, nutrients and dissolved gas molecules flow through the channel;
the method comprising:
a. constructing an ex vivo bone marrow microenvironment perfused by nutrients and dissolved gas molecules (bone marrow niche) in the microfluidic device by:
  (i) seeding a surface of the microfluidic device with viable osteoblasts; and
  (ii) culturing the cells to form 3D nodular structures that comprise a 3D bone-like tissue:
  the 3D bone-like tissue being characterized by an extracellular matrix secreted by the viable adherent osteoblasts;
b. preparing a multiple myeloma tumor biospecimen composition comprising viable human multiple myeloma cells from a subject and plasma autologous to the subject; and
c. seeding the ex vivo bone marrow microenvironment perfused by nutrients and dissolved gas molecules with the MM tumor biospecimen, and forming an ex vivo microenvironment in the microfluidics device effective to recapitulate spatial and temporal characteristics of a multiple myeloma cancer niche in vivo and to maintain viability of the MM cells in the MM cancer niche in the microfluidics device ex vivo;
wherein the microfluidic device is effective to control flow of minute amounts of the liquids, nutrients and dissolved gas molecules in the MM cancer niche;
wherein the ex vivo MM cancer niche in the microfluidic device is responsive to changing conditions of perfusion of the ex vivo MM cancer niche by the minute amounts of liquids, nutrients and dissolved gas molecules in the microfluidics device.

14. The method for preparing an ex vivo multiple myeloma (MM) cancer niche according to claim 13, wherein the MM niche further comprises osteoblast-secreted and MM cell-secreted soluble cytokines and growth factors.

15. The method for preparing an ex vivo multiple myeloma (MM) cancer niche according to claim 13, wherein the MM cells are adherent to osteoblasts of the BM niche.

16. The method for preparing an ex vivo multiple myeloma (MM) cancer niche according to claim 15, wherein the MM cells adhere to the osteoblasts of the BM niche by cell-cell interaction.

17. The method for preparing an ex vivo multiple myeloma (MM) cancer niche according to claim 13, wherein the human myeloma cells are cellular components of a bone marrow aspirate.

18. The method for preparing an ex vivo multiple myeloma (MM) cancer niche according to claim 13, wherein the human myeloma cells are cellular components of peripheral blood.

19. The method for preparing an ex vivo multiple myeloma (MM) cancer niche according to claim 13, wherein the human myeloma cells are cellular components of a core biopsy.

20. The method for preparing an ex vivo multiple myeloma (MM) cancer niche according to claim 13, wherein the ex vivo multiple myeloma (MM) cancer niche is suitable for propagation of the human myeloma cells for at least 7 days.

21. The method for preparing an ex vivo multiple myeloma (MM) cancer niche according to claim 13, wherein the sample of human myeloma cells added to the BM niche constitutes $1\times10^4$ to $1\times10^5$ mononuclear cells.

22. The method for preparing an ex vivo multiple myeloma (MM) cancer niche according to claim 13, wherein propagation of the MM cells is capable of producing deterioration of the 3D ossified tissue of the BM niche.

* * * * *